(12) United States Patent
Zhang et al.

(10) Patent No.: US 9,340,574 B2
(45) Date of Patent: May 17, 2016

(54) INHIBITORS OF PROTEIN TYROSINE PHOSPHATASES

(71) Applicant: Indiana University Research and Technology Corporation, Indianapolis, IN (US)

(72) Inventors: Zhong-Yin Zhang, Carmel, IN (US); Sheng Zhang, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/432,511

(22) PCT Filed: Oct. 3, 2013

(86) PCT No.: PCT/US2013/063278
§ 371 (c)(1),
(2) Date: Mar. 31, 2015

(87) PCT Pub. No.: WO2014/055768
PCT Pub. Date: Apr. 10, 2014

(65) Prior Publication Data
US 2015/0239931 A1 Aug. 27, 2015

Related U.S. Application Data

(60) Provisional application No. 61/709,668, filed on Oct. 4, 2012.

(51) Int. Cl.
| | | |
|---|---|---|
| *A61K 38/06* | (2006.01) | |
| *A61K 38/07* | (2006.01) | |
| *C07K 5/087* | (2006.01) | |
| *C07F 9/655* | (2006.01) | |
| *C07F 9/6558* | (2006.01) | |
| *C07F 9/38* | (2006.01) | |
| *C07K 5/065* | (2006.01) | |
| *A61K 38/00* | (2006.01) | |

(52) U.S. Cl.
CPC ............ *C07K 5/0812* (2013.01); *C07F 9/3882* (2013.01); *C07F 9/65522* (2013.01); *C07F 9/65586* (2013.01); *C07K 5/06078* (2013.01); *A61K 38/00* (2013.01)

(58) Field of Classification Search
CPC ........ A61K 38/00; A61K 38/06; A61K 38/07
See application file for complete search history.

(56) References Cited

U.S. PATENT DOCUMENTS

2012/0088720 A1 4/2012 Zhang et al.

OTHER PUBLICATIONS

Zhang, S., et al., Acquisition of a potent and selective TC=PTP inhibitor via a stepwise flurophore-tagged combinatorial synthesis and screening strategy, J. Am. Chem. Coc., 2009, vol. 131, pp. 13072-13079.
Sun, J.P., et al., Crystal Structure of PTPIB complexed with a potent and selective bidentate inhibitor, J. Biol. Chem., 2003, vol. 278, pp. 12406-12414.
Stankovic, C.J., et al., The role of 4-phosphonodifluoromethyl-and-4-phosphono-phenylalanine in the selectivity and cellular uptake of SH2 domain ligands, Bioorg. Med. Chem. Lett., 1997, vol. 7(14), pp. 1909-1914.
Zhang, S., et al., PTPIB as a drug target: recent developments in PTPIB inhibitor discovery, Drug Discovery Today, May 2007, vol. 12, pp. 373-381.
Burke, Jr. T.R., et al., Phoshotyrosyl mimetics in the development of signal transduction inhibitors, Acc. Chem. Res., 2003, vol. 36, pp. 426-433.
Zhang, Zy., Protein tyrosine phosphatases: structure and function, substrate specificity, and inhibitor development, Rev. Pharmacol. Toxicol. 2002, 42, pp. 209-234.
Puius, et al., Identification of a second aryl phosphate-binding site in protein-tyrosine phosphatase 1B: A paradigm for inhibitor design, Proc. Natl. Acad. Sci. USA 1997, 94, pp. 13420-13245.
Burke, et al., Potent inhibition of insulin-receptor dephosphorylation by a hexamer peptide-containing the phosphotyrosyl mimetic F2Pmp Biochem. Biophys. Res. Commun. 1994, vol. 204, pp. 129-134.
Cho, C. Y., et al., Experimental diagnostics to determine the local composition of an aqueous copper sulfate solution, Cell Metab., 2006, 3, pp. 367-378.
Xu, et al., PTP-MEG2 is activated in polycythemia vera erythroid progenitor cells and is required for growth and expansion of erythroid cells, J. Blood, 2003, vol. 102, pp. 4354-4360.
Barr, et al., Large-scale structural analysis of the classical human protein tyrosine phosphatome., Cell 2009, vol. 136, pp. 352-363.
Gordeev, M.F. et al., N-α-Fmoc-4-phosphono(difluoromethyl)-L-phenylalanine: A new O-phosphotyrosine isosteric building block suitable for direct incorporation into peptides, Tetrahedron Letters, 1994, vol. 35, Issue 41, pp. 7585-7588.
Qui, W. et al., a facile and general preparation of a,a-difluoro benzylic phosphonates by the CuCI promoted coupling reaction of the (diethylphosphonyl)difluoromethylcadmium reagent with aryl Iodides Original, Tetrahedron Letters, 1996, vol. 37, Issue 16, pp. 2745-2748.
Navaza, AMoRe: an automated package for molecular replacement, Acta. Crystallogr. 1994, A50, pp. 157-163.
Brünger, et al., Crystallography & NMR System: A New Software Suite for Macromolecular Structure Determination, Acta. Crystallogr. D. Biol. Crystallogr. 1998, vol. 54, pp. 905-921.
Jones, et al., Improved methods for building protein models in electron density maps and the location of errors in these models, Acta. Crystallogr, 1991, vol. A47, pp. 110-119.
Minor, et al., HKL-3000: the integration of data reduction and structure solution—from diffraction images to an initial model in minutes, Acta. Crystallogr. 2006, D62, pp. 859-866.
Higuchi, et al., Pro-drugs as Novel Delivery Systems, vol. 14 of the A.C.S. Symposium Series.
Liu et al., Prolonged treatment of primary hepatocytes with oleate induces insulin resistance through p38 mitogen-activated protein kinase., J. Biol. Chem. 2007, vol. 282, pp. 14205-14212.
Hunter, Tyrosine phosphorylation: thirty years and counting, Curr. Opin. Cell Biol., 2009, vol. 21, pp. 140-146.

(Continued)

*Primary Examiner* — James H Alstrum Acevedo
*Assistant Examiner* — Kaipeen Yang
(74) *Attorney, Agent, or Firm* — Stinson Leonard Street LLP

(57) ABSTRACT

Novel protein tyrosine phosphatase (PTP) inhibitor compounds synthesized from phosphonodifluoromethyl phenylalanine (F2Pmp) are provided. Use of these compounds for inhibiting a PTP enzyme (such as PTP-MEG2), as well as treating a disease, disorder, or condition associated with inappropriate activity of a PTP (such as type 2 diabetes), is also provided.

18 Claims, 24 Drawing Sheets

(56) References Cited

OTHER PUBLICATIONS

Jänne, et al., Factors underlying sensitivity of cancers to small-molecule kinase inhibitors., J. Nat. Rev. Drug Discov. 2009, vol. 8, pp. 709-723.

Tonks, Protein tyrosine phosphatases: from genes, to function, to disease, Nat. Rev. Mol. Cell Biol. 2006, vol. 7, pp. 833-846.

Zhang, Protein tyrosine phosphatases: prospects for therapeutics. Protein tyrosine phosphatases: prospects for therapeutics, Curr. Opin. Chem. Biol., 2001, vol. 5, pp. 416-423.

Julien, et al., Inside the human cancer tyrosine phosphatome., Nat. Rev. Cancer 2011, vol. 11, pp. 35-49.

Gu, et al., Cloning and expression of a cytosolic megakaryocyte protein-tyrosine-phosphatase with sequence homology to retinaldehyde-binding protein and yeast SEC14p., Proc. Natl. Acad. Sci., 1992, vol. 89, pp. 2980-2984.

Huynh, et al., Homotypic secretory vesicle fusion induced by the protein tyrosine phosphatase MEG2 depends on polyphosphoinositides in T cells, Immunol. 2003, vol. 171, pp. 6661-6671.

Kruger, et al., Protein-tyrosine Phosphatase MEG2 Is Expressed by Human Neutrophils, J. Biol. Chem. 2002, vol. 277, pp. 2620-2628.

Zhao, et al., Specific Interaction of Protein Tyrosine Phosphatase-MEG2 with Phosphatidylserine*, J. Biol. Chem. 2003, vol. 278, pp. 22609-22614.

Wang, et al., Enlargement of Secretory Vesicles by Protein Tyrosine Phosphatase PTP-MEG2 in Rat Basophilic Leukemia Mast Cells and Jurkat T Cells, J. Immunol. 2002, vol. 168, pp. 4612-4619.

Chen, et al., Why is phosphonodifluoromethyl phenylalanine a more potent inhibitory moiety than phosphonomethyl phenylalanine toward protein-tyrosine phosphatases? Biochem. Biophys. Res. Commun. 1995, vol. pp. 216, 976-984.

Yuan, et al., Protein-tyrosine Phosphatase PTPN9 Negatively Regulates ErbB2 and Epidermal Growth Factor Receptor Signaling in Breast Cancer Cells*, J. Biol. Chem. 2010, vol. 285, pp. 14861-14870.

Wei, et al., Feedback regulation of hepatic gluconeogenesis through modulation of SHP/Nr0b2 gene expression by . Sirt1 and FoxO1. , Am. J. Physiol. Endocrinol. Metab. 2011, vol. 300, pp. E312-320.

Brünger, A., Free R value: a novel statistical quantity for assessing the accuracy of crystal structures, Nature 1992, vol. 355, pp. 472-475.

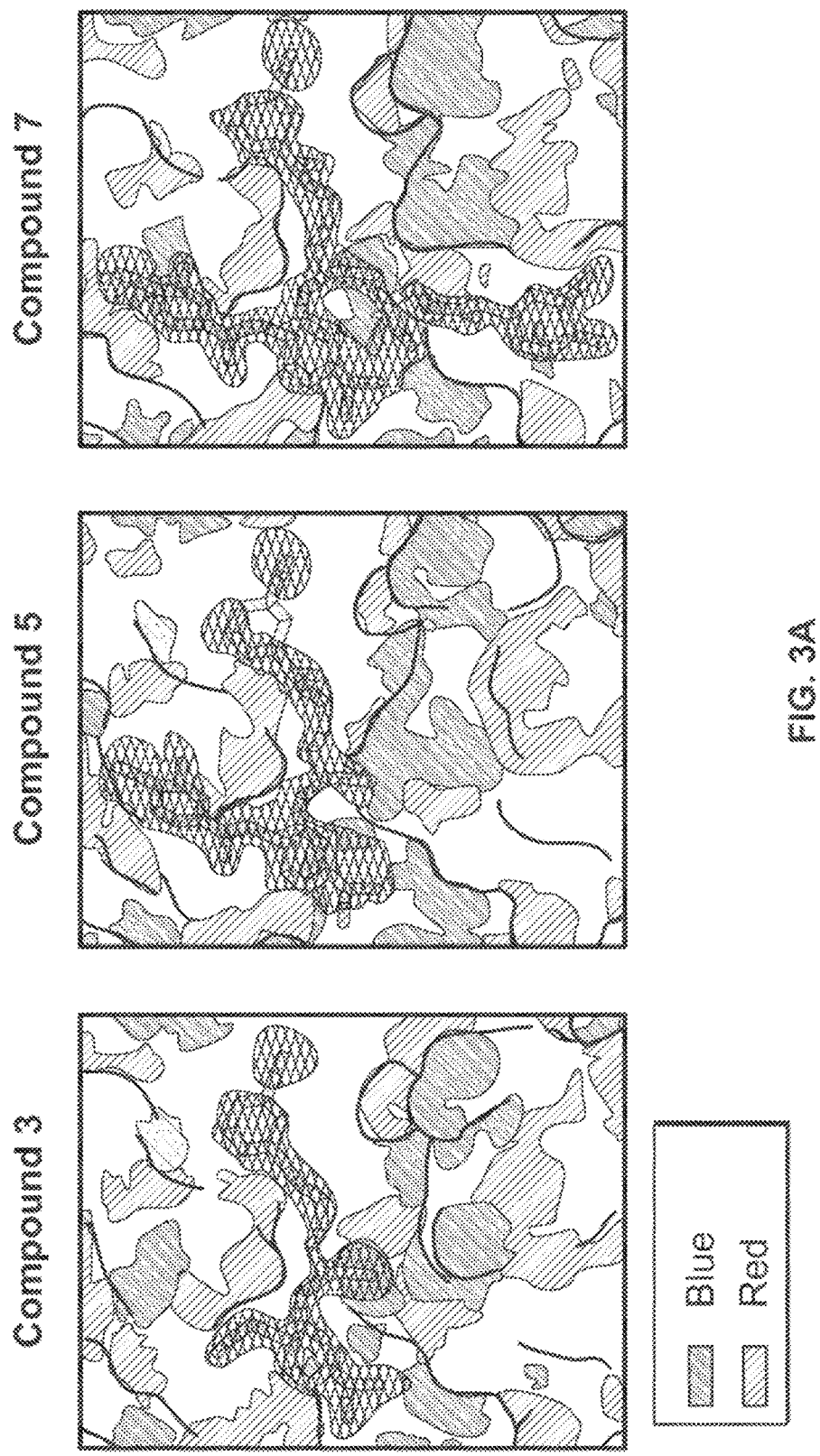

INHIBITORS OF PROTEIN TYROSINE PHOSPHATASES

CROSS-REFERENCE TO RELATED APPLICATIONS

This application claims priority to International Publication Number WO 2014/055768, filed on Oct. 3, 2013, which claims priority to U.S. Provisional Patent Application No. 61/709,668, filed on Oct. 4, 2012, each of which is incorporated by reference herein in its entirety.

STATEMENT OF GOVERNMENT SUPPORT

This invention was made with government support under CA152194 awarded by the National Institutes of Health. The government has certain rights in the invention.

BACKGROUND

The present disclosure relates generally to compounds that inhibit protein tyrosine phosphatases (PTPs). PTPs play an important role in the regulation of cellular growth and differentiation by serving as key regulatory components in the tyrosine phosphorylation-mediated signaling pathways. Defective or inappropriate regulation of PTPase activity leads to aberrant tyrosine phosphorylation, which contributes to the development of many human diseases including cancers and diabetes. For example, gene knockout studies in mice have identified PTP as a promising target for anti-diabetes/obesity drug discovery. Previous studies indicate that PTP-MEG2 (protein tyrosine phosphatase, non-receptor type 9, an intracellular PTP containing an N-terminal Sec14 homology domain) is an antagonist of hepatic insulin signaling (Cho, et al., *Cell Metab.* 2006, 3, 367-378). Ectopic expression of PTP-MEG2 in HepG2 cells reduces insulin-stimulated insulin receptor (IR) phosphorylation at Tyr1162/1163, which is required for its kinase activity, while RNAi-mediated PTP-MEG2 knockdown enhances insulin action. Additionally, increased PTP-MEG2 expression in liver suppresses insulin signaling, whereas hepatic silencing of PTP-MEG2 improves insulin sensitivity in db/db diabetic mice.

Thus, specific and potent PTP inhibitors are valuable for both biological studies and pharmacological development. However, the highly conserved PTP active site (i.e. the pTyr-binding cleft) makes it extremely difficult to develop selective active site-directed inhibitors. Remarkably, pTyr alone is not sufficient for high-affinity binding and residues flanking pTyr also contribute to PTP substrate recognition (Zhang, *Annu. Rev. Pharmacol. Toxicol.* 2002, 42, 209-234). These findings indicate that there are subpockets adjacent to the PTP active site that can be targeted for inhibitor design. A known strategy for obtaining potent and selective PTP inhibitors is by tethering appropriately functionalized moieties to a non-hydrolyzable pTyr mimetic in order to engage both the active site and nearby peripheral binding pockets (Puius, et al., *Proc. Natl. Acad. Sci. USA* 1997, 94, 13420-13245). Phosphonodifluoromethyl phenylalanine ($F_2$Pmp), a well-established non-hydrolyzable pTyr surrogate (Burke, et al., *Biochem. Biophys. Res. Commun.* 1994, 204, 129-134; and Chen, et al., *Biochem. Biophys. Res. Commun.* 1995, 216, 976-984), has been previously utilized to generate potent and selective PTP inhibitors (Shen, et al., *J. Biol. Chem.* 2001, 276, 47311-47319; Sun, et al., *J. Biol. Chem.* 2003, 278, 12406-12414; and Zhang, et al., *J. Am. Chem. Soc.* 2009, 131, 13072-13079).

Thus, there is a need for more potent and selective inhibitors for individual members of the PTP enzyme family. As provided herein, the present disclosure provides novel PTP inhibitor compounds synthesized from $F_2$Pmp.

BRIEF DESCRIPTION

The present disclosure relates to new compounds that inhibit protein tyrosine phosphatases (PTPs). In one aspect, selective inhibitors for individual members of the PTP enzyme family, such as PTP-MEG2, are provided. Also provided is the method of synthesizing PTP inhibitor compounds starting from phosphonodifluoromethyl phenylalanine ($F_2$Pmp) as a precursor.

Accordingly, in one aspect, the present disclosure is directed to a compound of Formula A:

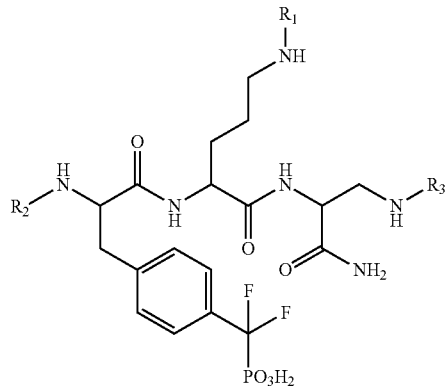

Formula A or a therapeutically suitable prodrug thereof or a therapeutically suitable salt thereof, wherein $R^1$, $R^2$, and $R^3$ are the same or different and each individually is an acyl group of a carboxylic acid, for use as inhibitors of PTP. In one particular embodiment, the compound has the structure of compound 7

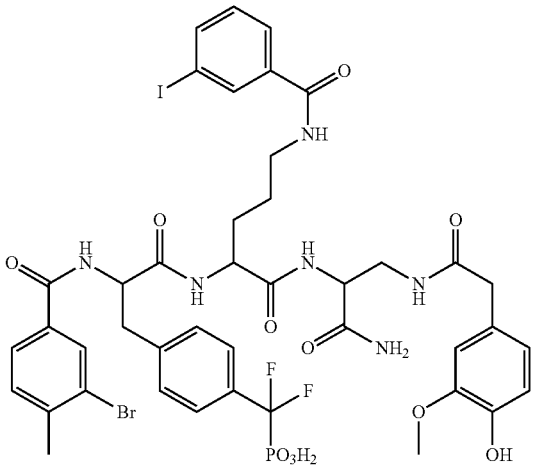

Compound 7 or a therapeutically suitable prodrug thereof or a therapeutically suitable salt thereof.

In another aspect, a use of the novel PTP inhibitor compounds for treating a disease, disorder, or condition associated with inappropriate activity of a PTP (e.g. type 2 diabetes) is provided.

Also provided is a use of the novel PTP inhibitor compounds in the manufacture of a medicament for the treatment of a disease, disorder, or condition associated with inappropriate activity of a protein phosphatase.

In another aspect, a use of the novel PTP inhibitor compounds for inhibiting a protein tyrosine phosphatase enzyme (e.g. a PTP enzyme located in a human or an animal cell) is provided.

In yet another aspect, the present disclosure also provides a pharmaceutical composition comprising the novel PTP inhibitor compounds and a pharmaceutically acceptable carrier.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 3A-D depict structures of PTP-MEG2 in complex with Compounds 3, 5 and 7. The Figures were created using PyMol (DeLano Scientific; http://www.pymol.org). FIG. 3A shows the unbiased $F_o-F_c$ omit map of Compounds 3, 5, and 7 contoured at 3σ level. FIG. 3B shows the overlay of the crystal structures of PTP-MEG2 in complex with Compound 3 (blue, 1.8 Å resolution), 5 (red, 2.0 Å resolution) and 7 (green, 1.4 Å resolution). The $F_2Pmp$ core occupies the active site; the 3-iodobenzoic amide moiety binds to the same hydrophobic patch formed by residues Pro315, Phe319, Pro337 and Phe556. The P-loop, pTyr recognition loop and Q-loop are colored by orange, yellow and red, respectively. FIG. 3C is a stereo diagram of the binding interactions between PTP-MEG2 and Compound 7. Color scheme for carbon atoms: residues of PTP-MEG2—yellow; $F_2Pmp$ core (including the ornithine linker)—red; the 3-iodobenzoic amide moiety connected to the Nγ of ornithine—orange; the 3-bromo-4-methylbenzoic amide group connected to the N-terminal of $F_2Pmp$—slate blue; the homovanillic amide group and the diaminopropionic acid linker—green. The P-loop, pTyr loop, and Q-loop in PTP-MEG2 are also shown. The interactions between PTP-MEG2 and the compound are shown in dash lines. The polar interactions are shown in the dash lines between the compound and the residues D335, C515, S516, R521, Q559, and P-LOOP; the hydrophobic interactions or Van der Waals contacts are shown in the dash lines between the compound and the residues E308, Y304, P315, Y333, V336, P337, A517, 1519, and F319. FIG. 3D depicts the surface representation of PTP-MEG2 in complex with Compound 7. Carbon atoms in Compound 7 are designated green, and PTP-MEG2 residues are designated yellow.

FIG. 4A shows the effects of Compound 7 on insulin signaling pathway. Mouse primary hepatocytes were cultured in 0.5% FBS DMEM medium overnight. Prior to insulin stimulation, the cells were pretreated with Compound 7 or 8 for 1 hour. Then the cells were stimulated with 5 nM insulin for 5 minutes. Insulin signaling was analyzed by Western Blots using phospho-specific antibodies. FIG. 4B shows the regulation of Foxo1 target genes by Compound 7. Mouse primary hepatocytes were cultured in DMEM medium plus 0.5% FBS for overnight in the presence or absence of insulin or Compound 7 or 8. Then the cells were harvested for mRNA isolation and gene expression analysis using real-time PCR. The mRNA levels of Foxo1 target genes were normalized with Ppia as an internal control. Data are presented as mean±SEM. *, P<0.05 for Compound 7 vs. DMSO; #, P<0.05 for INS+Compound 7 vs. INS alone.

FIG. 5A depicts insulin tolerance tests (ITT) performed on Day 7 by injecting intraperitoneally a bolus of 0.75 unit/kg of human regular insulin. FIG. 5B shows an analysis of area under the curve (AUC) for ITT performed using the data from Panel A (n=5). FIG. 5C depicts glucose tolerance tests (GTT) carried out on Day 9 after a bolus of 1 g/kg glucose was injected intraperitoneally. FIG. 5D shows an AUC analysis for the GTT data in Panel C. FIG. 5E depicts pyruvate tolerance tests (PTT) performed on Day 12 after an injection of 2 g/kg pyruvate solution. FIG. 5F shows an AUC representation of the PTT data in Panel E. *, P<0.05 for Compound 7 vs. vehicle. FIGS. 5G-I show that Compound 7 has an insulin-sensitizing effect in metabolic tissues. At the end of 2-week injections of Compound 7, animals were fasted overnight and stimulated with a bolus of 1 unit of human regular insulin or saline via vena cava. Three minutes later, liver, skeletal muscle, and white adipose tissue (WAT) were collected sequentially for insulin signaling analysis. FIG. 5G depicts the phosphorylation of Tyr1162/1163 in insulin receptor (IR) and Ser473 phosphorylation in Akt kinases and the corresponding proteins in the liver, skeletal muscle, and white adipose tissue (WAT) were analyzed by immunoblots. FIGS. 5H-I show immunoblot data quantified by normalizing signal intensities of phosphorylated to total proteins. *, P<0.05 for Compound 7 vs. vehicle.

FIG. 9A shows 3T3-L1 adipocytes (10-day differentiation) that were serum starved overnight and treated with Compound 7 or 8 (final DMSO 0.5%) for 1 hour before stimulation with insulin. Cell lysate (20 µg protein) was subjected to 10% SDS-PAGE and probed with phospho-Akt, phospho-IR (Y1162/1163) or Akt antibody, respectively. FIG. 9B shows HepG2 cells that were maintained in DMEM with 10% FBS, serum starved overnight, and treated with Compound 7 or 8 (final DMSO 0.5%) for 1 hour before stimulation with 10 nM insulin for 30 min. Cell lysate (20 µg protein) was subjected to 10% SDS-PAGE and probed with phospho-IR(Y1162/1163), phospho-Akt (pS473) or total Akt antibody, respectively. FIG. 9C shows C2C12 myotubes (7-day differentiation) that were serum starved overnight and treated with Compound 7 or 8 (final DMSO 0.5%) for 1 hour before stimulation with 100 nM insulin for 30 min. Cell lysate (20 µg protein) or insulin receptor immunoprecipitation beads were subjected to 10% SDS-PAGE and probed with phospho-Akt, Akt, insulin receptor beta or phospho-tyrosine antibody (4G10), respectively. The non-specific band from insulin receptor immunoprecipitates served as a loading control for insulin receptor and phospho-insulin receptor.

Figure 1:
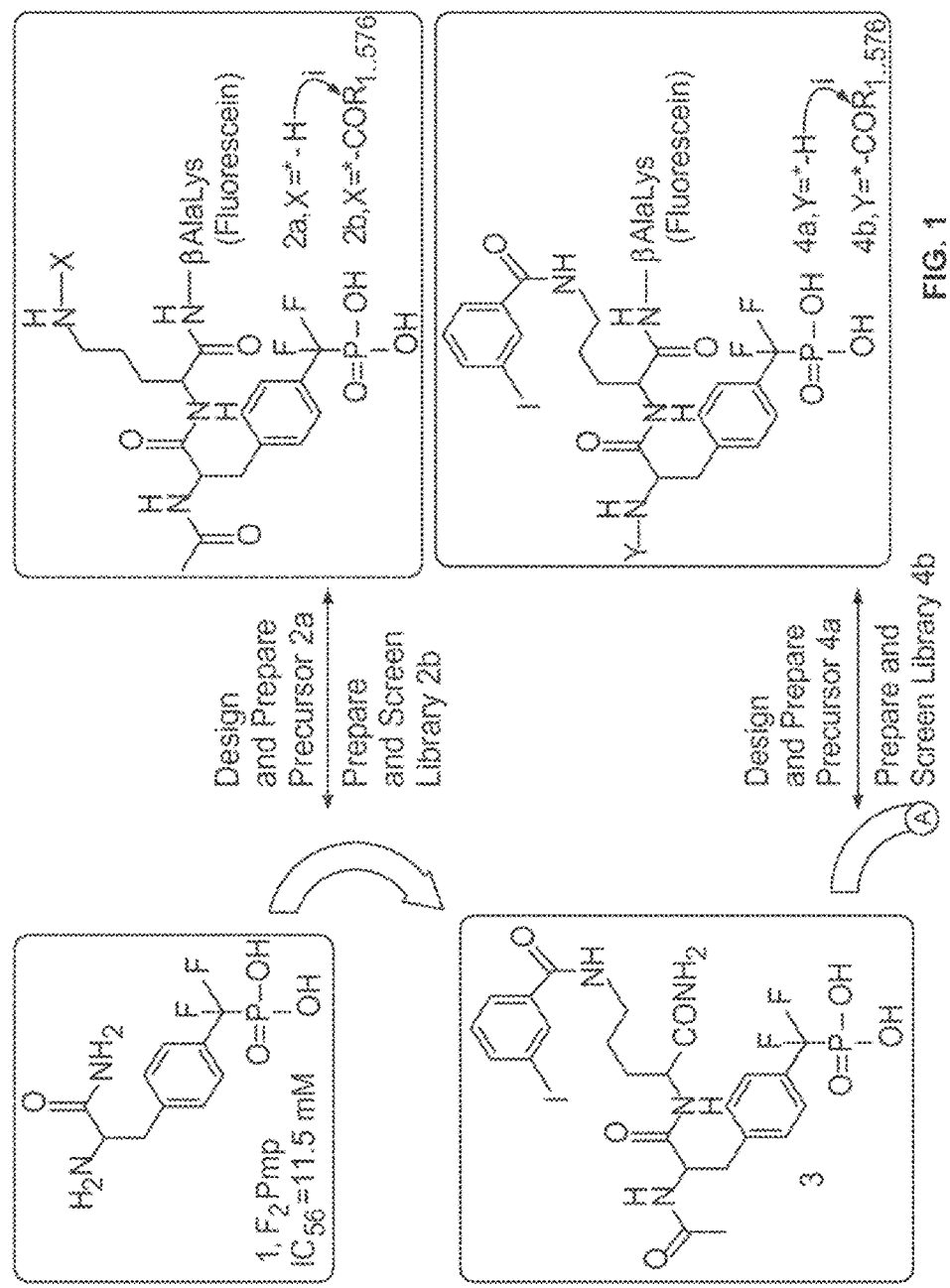
FIG. 1 depicts a stepwise library approach of PTP-MEG2 inhibitors. The —NH—X represents the free amine from ornithine and its derivatives (the first library). The 3-iodobenzoic amide moiety is the best hit from the first library. The —NH—Y represents the α-amino group from $F_2Pmp$ amine and its derivatives (the second library). The 3-bromo-4-methylbenzoic amide moiety is the best hit from the second library. The —NH—Z represents the free amine from the diaminopropionic acid linker and its derivatives (the third library). The homovanillic amide moiety is the best hit from the third library. The βAlaLys(Fluorescein) moiety represents a fluorescein tag linked through a β-Ala-Lys spacer. The library synthesis procedure, "step i" shown in FIG. 1, includes a library of 576 different carboxylic acids ($R_{1...576}$—COOH), to which HBTU, HOBt, and NMM are sequentially added for the activation of the carboxylic acids, and then condensed with the corresponding library core for the formation of the —$COR_{1...576}$ moieties.
Figure 1:
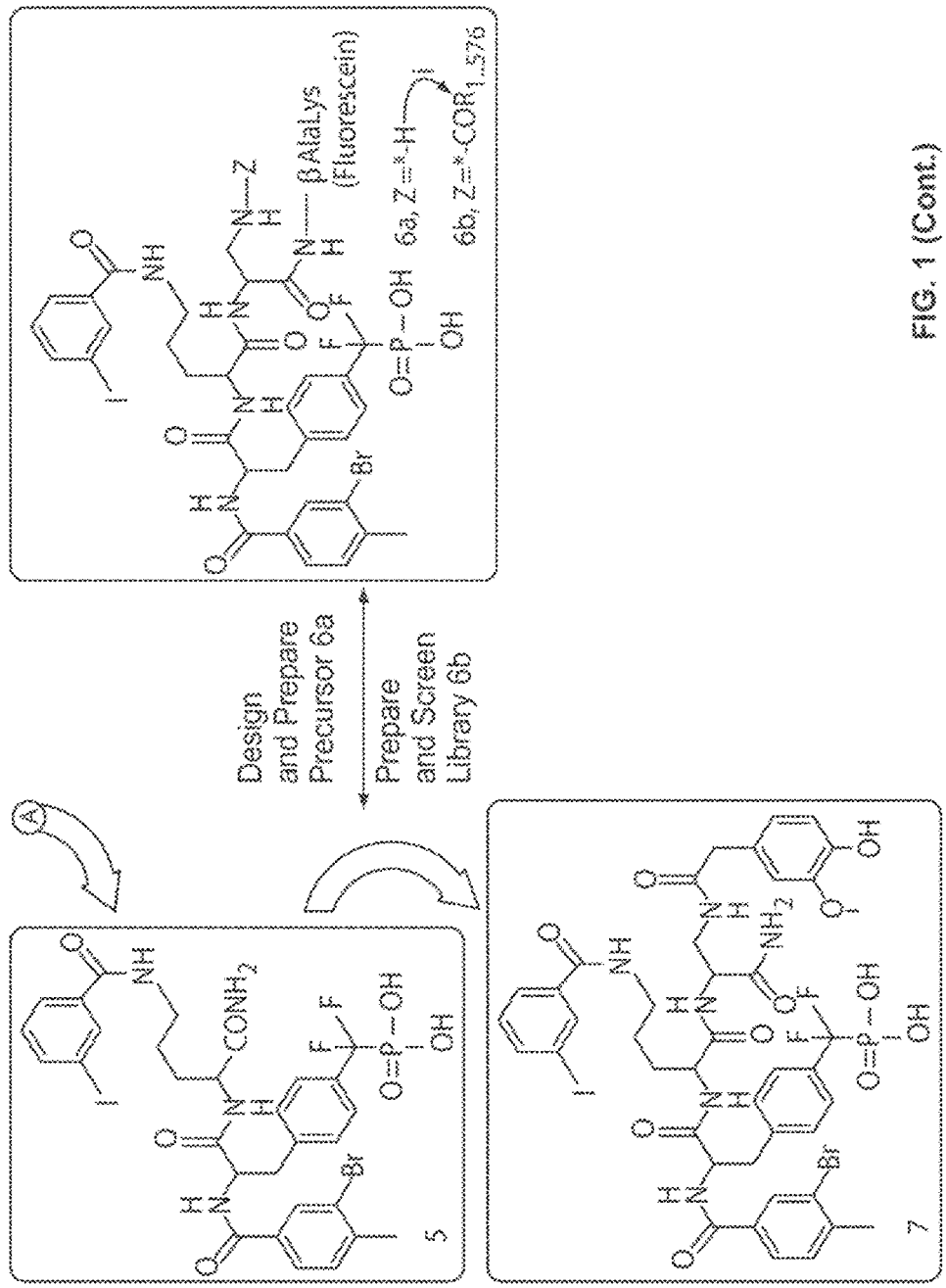

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

In accordance with the present disclosure, new compounds that inhibit protein tyrosine phosphatases (PTPs) are provided. In one aspect, selective inhibitors for PTP-MEG2 are provided. Also provided is a method of synthesizing the novel PTP inhibitor compounds starting from phosphonodifluoromethyl phenylalanine (F₂Pmp). Pharmaceutical compositions comprising the above PTP inhibitor compounds are also contemplated.

In another aspect, a method of inhibiting the activity of a phosphatase and/or treating a disease, disorder, or condition associated with inappropriate activity of a protein phosphatase is disclosed comprising the steps of identifying a patient in need of a compound that regulates the activity of at least one phosphatase and providing the patient with a therapeutically effective dosage of at least one compound that at least partially inhibits the activity of at least one phosphatase, for example PTP-MEG2. In one representative embodiment, the disease, disorder, or condition to be treated is type 1 diabetes, type 2 diabetes, obesity, metabolic syndrome, Crohn's disease, rheumatoid arthritis, Graves' disease, systemic lupus erythematosus, leukemia, or tuberculosis.

In a set of representative embodiments the phosphatase inhibitor is of Formula A:

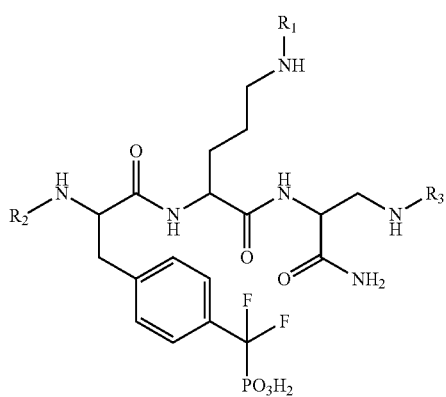

Formula A wherein moieties $R^1$, $R^2$, and $R^3$ are the same or different and each individually is an acyl group of a carboxylic acid.

In example compounds of Formula A, moieties $R^1$, $R^2$, and $R^3$ are the same or different and each individually is an acyl group of a carboxylic acid, wherein the carboxylic acid is selected from the group consisting of: 3-dimethylaminobenzoic acid, 2-(2-cyanophenylthio)benzoic acid, 2-(4-cyanophenylthio) benzoic acid, (−)-2-oxo-4-thiazolidine-carboxylic acid, (−)-N-acetylneuraminic acid, (+)-6-methoxy-a-methyl-2-naphthaleneacetic acid, (+)-carbobenzyloxy-D-proline, (+)-menthoxyacetic acid, (+)-2-(2-chlorophenoxy) propionic acid, (1)-1-methyl-2-cyclohexene-1-carboxylic acid, (1-naphthoxy)acetic acid, (1R)-(1a,2b,3a)-(+)-3-methyl-2nitromethyl-5-oxocyclopentaneacetic acid, (1R,4R)-7,7dimethyl-2-oxobicyclo[2.2.1]heptane-1-carboxylic acid, (1S)-(+)-camphanic acid, (1S,3R,4S,5R)-1,3,4,5-tetrahydroxycyclohexanecarboxylic acid, (2,4-di-tert-pentylphenoxyl)acetic acid, (2-naphthoxy)acetic acid, (2-pyrimidylthio)acetic acid, (4-carboxybutyl)triphenylphosphonium bromide, (4-chlorophenylthio)acetic acid, (4-methylphenoxy)acetic acid, (a,a,a-trifluoro-m-tolyl)acetic acid, (E)-2-((4-hydroxyphenyl)diazenyl)benzoic acid, (E)-2-methyl-3-(2,4,5-trimethoxyphenyl)acrylic acid, (methylthio)acetic acid, (R)-(−)-2-hydroxy-4-phenylbutyric acid, (R)-(−)-3-chloromandelic acid, (R)-(−)-hexahydromandelic acid, (R)-(+)-2-pyrrolidone-5-carboxylic acid, (R)(+)-citronellic acid, (R)-2-(1-phenylethylcarbamoyl)benzoic acid, (R)-2-hydroxy-2-phenylacetic acid, (R)-3,3,3-trifluoro2-methoxy-2-phenylpropanoic acid, (R)-6-hydroxy-2,5,7,8-tetramethyl-chroman-2-carboxylic acid, (S)-(−)-indoline-2carboxylic acid, (S)-(+)-2-oxo-4-phenyl-3-oxazolidineacetic acid, (S)-(+)-5-oxo-2-tetrahydro-furancarboxylic acid, (S)(+)-hexahydromandelic acid, (S)-(+)-N-[1-(1-naphthyl)ethyl]-phthalamic acid, (S)-(+)-[3-acetylmandelic acid, (S)-2(1-phenylethylcarbamoyl)benzoic acid, (S)-2-(4-isobutylphenyl)propanoic acid, (S)-2-(phenylcarbamoyloxy) propanoic acid, (S)-3-(benzyloxycarbonyl)-2oxoimidazolidine-4-carboxylic acid, (S)-3,3,3-trifluoro-2methoxy-2-phenylpropanoic acid, (S)-3,3,3-trifluoro-2methoxy-2-phenylpropanoic acid, (S)-6-methoxy-2,5,7,8-tetramethylchroman-2-carboxylic acid, (trimethylsilyl) acetic acid, (z)-2-cyano-3-(3-hydroxyphenyl)acrylic acid, 1-(4-chlorophenyl)-1-cyclopentanecarboxylic acid, 1-(tert-butyl)hydrocinnamic acid, 1,2-phenylenedioxydiacetic acid, 1,4-dihydro-2-methylbenzoic acid, 1,4-dihydroxy-2-naphthoic acid, 10-hydroxydecanoic acid, 10-undecynoic acid, 1-admantanecarboxylic acid, 1-cyano-1-cyclopropane-carboxylic acid, 1-hydroxy-2-naphthoic acid, 1-isoquinolinecarboxylic acid, 1-methyl-(1S,2R)-(+)-cis-1,2,3,6-tetrahydrophthalate, 1-methyl-1-cyclohexane-carboxylic acid, 1-methyl-1H-indole-2-carboxylic acid, 1-methyl-2-pyrrolecarboxylic acid, 1-methylcyclopropane-carboxylic acid, 1-naphthoic acid, 1-phenyl-1-cyclopentane-carboxylic acid, 1-phenyl-1-cyclopropane-carboxylic acid, 1-pyreneacetic acid, 1-pyrenebutyric acid, 1-pyrenecarboxylic acid, 2-((1R,2R,3R,4S)-3-hydroxy-4,7,7-trimethylbicyclo[2.2.1]heptan-2-yl)acetic acid, 2-((benzyloxycarbonyl)(methyl)amino)-2methylpropanoic acid, 2-(2,(trifluoromethyl)phenyl)acetic acid, 2-(2,4,5-trichlorophenoxy)-propionic acid, 2-(2,4dichlorophenoxy)-propionic acid, 2-(3,5-dinitrobenzamido)2-phenylacetic acid, 2-(3,5-dinitrobenzamido)-4-methylpentanoic acid, 2-(3-chlorophenoxy)propionic acid, 2-(4 (trifluoromethyl)phenyl)acetic acid, 2-(4-chloro-3 nitrobenzoyl)-benzoic acid, 2-(4-chlorophenoxy)-2-methylpropionic acid, 2-(4-chlorophenoxy)propionic acid, 2-(4fluorobenzoyl)benzoic acid, 2-(4-hydroxy-3-methoxyphenyl)acetic acid, 2-(4-hydroxyphenoxy)-propionic acid, 2-(4-isobutylphenyl)propanoic acid, 2-(4-nitrophenyl)propionic acid, 2-(benzyloxycarbonylamino)-3-(1H-indol-3-yl) propanoic acid, 2-(trifluoromethyl)acrylic acid, 2-(trifluoromethyl)benzoic acid, 2-(trifluoromethyl)cinnamic acid, 2,2,3,3-tetramethyl-cyclopropanecarboxylic acid, 2,2-bis (hydroxymethyl)-propionic acid, 2,3,4,5,6-pentafluoro-cinnamic acid, 2,3,4,5,6-pentafluorophenoxy acetic acid, 2,3,4,5,6-pentafluorophenyl-acetic acid, 2,3,4,5-tetrafluorobenzoic acid, 2,3,4-trifluorocinnamic acid, 2,3,4-trihydroxybenzoic acid, 2,3,4-trimethoxybenzoic acid, 2,3,5,6-tetrafluoro-4-hydro-oxy-benzoic acid hydrate, 2,3,5,6-tetrafluorobenzoic acid, 2,3,5,6-tetrafluoro-p-toluic acid, 2,3,5-triiodobenzoic acid, 2,3,6-trifluorobenzoic acid, 2,3-dichlorobenzoic acid, 2,3-difluorobenzoic acid, 2,3-dihydroxybenzoic acid, 2,3-dimethylbenzoic acid, 2,4,5trichlorophenoxyacetic acid, 2,4,5-trimethoxybenzoic acid, 2,4,6-trichlorobenzoic acid, 2,4,6-trifluorobenzoic acid, 2,4,6-trihydroxybenzoic acid monohydrate, 2,4,6-trimethylbenzoic acid, 2,4-bis(trifluoromethyl)-benzoic acid, 2,4-dichloro-5-fluorobenzoic acid, 2,4-dichloro-5-sulfamoylbenzoic acid, 2,4-dichlorobenzoic acid, 2,4-dichlorophenylacetic acid, 2,4-difluorobenzoic acid, 2,4-difluorophenylacetic acid, 2,4-dihydroxybenzoic acid, 2,4-dimethylbenzoic acid, 2,4-dinitrobenzoic acid, 2,4-dinitrophenylacetic acid, 2,4-hexadienoic acid, 2,5-bis (trifluoromethyl)-benzoic acid, 2,5-dichlorobenzoic acid, 2,5-difluorobenzoic acid, 2,5-difluorophenylacetic acid, 2,5-dihydroxybenzoic acid, 2,5-dihydroxyphenylacetic acid, 2,5-dimethoxybenzoic acid, 2,5-dimethoxycinnamic acid, 2,6-dichloro-3-nitrobenzoic acid, 2,6-difluorobenzoic acid, 2,6-difluorophenylacetic acid, 2,6-dihydroxybenzoic acid, 2,6-dimethoxynicotinic acid, 2,6-dimethylbenzoic acid, 2,6-heptadienoic acid, 2-[4-(dibutylamino)-2-hydroxy-benzoyl] benzoic acid, 2-bibenzylcarboxylic acid, 2-biphenylcarboxylic acid, 2-bromo-3-nitrobenzoic acid, 2-bromo-4,5-dimethoxybenzoic acid, 2-bromo-5-methoxybenzoic acid, 2-bromo-5-nitrobenzoic acid, 2-bromoacrylic acid, 2-bromophenylacetic acid, 2-chloro-3-nitrobenzoic acid, 2-chloro-4,5-difluorobenzoic acid, 2-chloro-4-fluorobenzoic acid, 2-chloro-5-(methylthio)-benzoic acid, 2-chloro-5-(trifluoromethyl)benzoic acid, 2-chloro-5-nitrobenzoic acid, 2-chloro-5-nitrocinnamic acid, 2-chloro-6-fluorobenzoic acid, 2-chloro-6-fluorophenylacetic acid, 2-chloro-6-methylnicotinic acid, 2-chlorobenzoic acid, 2-chloronicotinic acid, 2-chlorophenylacetic acid, 2-chloropropionic acid, 2-ethoxy-1-naphthoic acid, 2-ethoxybenzoic acid, 2-ethyl-2-hydroxybutyric acid, 2-ethylbutyric acid, 2-ethylhexanoic acid, 2-ethylthio-2,2-diphenyl-acetic acid, 2-fluoro-3-(trifluoromethyl)-benzoic acid, 2-fluoro-4-(trifluoromethyl)-benzoic acid, 2-fluoro-5-methylbenzoic acid, 2-fluoro-5-nitrobenzoic acid, 2-fluoro-6-(trifluoromethyl) benzoic acid, 2-fluorobenzoic acid, 2-fluorocinnamic acid, 2-fluorophenylacetic acid, 2-hydroxy-3-isopropyl-6-methylbenzoic acid, 2-hydroxy-3-isopropylbenzoic acid, 2-hydroxy-3-methylbutyric acid, 2-hydroxy-6-isopropyl-3-methylbenzoic acid, 2-hydroxycaproic acid, 2-hydroxyhippuric acid, 2-hydroxyisobutyric acid, 2-hydroxyisobutyric acid, 2-hydroxynicotinic acid, 2-hydroxyphenylacetic acid, 2-iodobenzoic acid, 2-mercaptonicotinic acid, 2-methoxy-2-phenylacetic acid, 2-methoxy-4-(methylthio)-benzoic acid, 2-methoxy-4-nitrobenzoic acid, 2-methoxyphenylacetic acid, 2-methyl-1-cyclohexane-carboxylic acid (cis and trans), 2-methyl-3-nitrobenzoic acid, 2-methyl-3-phenylpropanoic acid, 2-methyl-4-oxo-4-phenylbutyric acid, 2-methyl-6-nitrobenzoic acid, 2-methylbutyric acid, 2-methylcinnamic acid, 2-methylcyclopropane-carboxylic acid (cis and trans), 2-methylhexanoic acid, 2-methylhippuric acid, 2-methyhydrocinnamic acid, 2-methylvaleric acid, 2-naphthoic acid, 2-naphthylacetic acid, 2-nitro-4-(trifluoromethyl)benzoic acid, 2-nitrobenzoic acid, 2-norbornaneacetic acid, 2-oxo-6pentyl-2H-pyran-3-carboxylic acid, 2-phenoxybenzoic acid, 2-phenoxybutyric acid, 2-phenoxypropionic acid, 2-propylpentanoic acid, 2-quinoxalinecarboxylic acid, 2-thiopheneacetic acid, 2-thiopheneacetic acid, 2-thiopheneglyoxylic acid, 3-(2-hydroxyphenyl)propionic acid, 3-(2-thienyl)acrylic acid, 3-(3,4,5-trimethoxyphenyl)-propionic acid, 3-(3,4-dimethoxyphenyl)-propionic acid, 3-(3-hydroxy-2,4,6-triiodophenyl)pentanoic acid, 3-(3-hydroxyphenyl)-propionic acid, 3-(3-methoxyphenyl)propionic acid, 3-(4-chlorobenzoyl)propionic acid, 3-(4-chlorobenzoyl)propionic acid, 3-(4-chlorobenzoyl)propionic acid, 3-(4-fluorobenzoyl)propionic acid, 3-(4-hydroxyphenyl)propionic acid, 3-(phenylsulfonyl)propionic acid, 3-(trifluoromethyl)cinnamic acid, 3-(trimethylsilyl)propynoic acid, 3,3,3-triphenylpropionic acid, 3,4-(methylenedioxy)cinnamic acid, 3,4-(methylenedioxy)phenyl-acetic acid, 3,4-dichlorobenzoic acid, 3,4-dichlorophenoxyacetic acid, 3,4-diethoxybenzoic acid, 3,4-difluorobenzoic acid, 3,4-dihydroxybenzoic acid, 3,4-dihydroxyhydrocinnamic acid, 3,4-dihydroxyphenylacetic acid, 3,5,6-trichlorosalicylic acid, 3,5-bis(trifluoromethyl)-phenyl acetic acid, 3,5-dibromobenzoic acid, 3,5-dichlorosalicyclic acid, 3,5-difluorocinnamic acid, 3,5-dihydroxy-2-naphthoic acid, 3,5-dinitrobenzoic acid, 3,5-dinitro-o-tuluic acid, 3,5-dinitro-p-toluic acid, 3,5-dinitrosalicyclic acid, 3,5-di-tert-butyl-4-hydroxy-benzoic acid, 3,5-di-tert-butylbenzoic acid, 3,7-dihydroxy-2-naphthoic acid, 3-thiopheneacetic acid, 3-benzoyl-2-pyridine-carboxylic acid, 3-benzoylbenzoic acid, 3-bromo-4-fluorobenzoic acid, 3-bromo-4-methylbenzoic acid, 3-bromo-5iodobenzoic acid, 3-bromobenzoic acid, 3-bromocinnamic acid, 3-carboxy-proxyl, 3-chloro-2-nitrobenzoic acid, 3-chloro-4-fluorobenzoic acid, 3-chloro-4-hydroxyphenylacetic acid, 3-chlorosalicyclic acid, 3-cyanobenzoic acid, 3-fluoro-2-methylbenzoic acid, 3-fluoro-4-hydroxy-phenylacetic acid, 3-fluoro-4-methoxybenzoic acid, 3-fluorophenylacetic acid, 3-furoic acid, 3-hydroxy-2-naphthoic acid, 3-hydroxy-2-quinoxaline-carboxylic acid, 3-hydroxy-4methoxybenxoic acid, 3-hydroxy-4-methoxy-cinnamic acid, 3-hydroxy-4-nitrobenzoic acid, 3-hydroxybenzoic acid, 3-hydroxybutyric acid, 3-hydroxyphenylacetic acid, 3-indolebutyric acid, 3-indoleglyoxylic acid, 3-indolepropionic acid, 3-iodo-4-methylbenzoic acid, 3-iodobenzoic acid, 3-isoquinolinecarboxylic acid hydrate, 3-methoxy-4-nitrobenzoic acid, 3-methoxycyclohexane-carboxylic acid (cis and trans), 3-methyl-2-phenylvaleric acid, 3-methylhippuric acid, 3-methylindene-2-carboxylic acid, 3-methylsalicylic acid, 3-methylvaleric acid, 3-nitreobenzoic acid, 3-nitrophenylacetic acid, 3-nitropropionic acid, 3-noradamantanecarboxylic acid, 3-oxo-1-indancarboxylic acid, 3-phenoxybenzoic acid, 3-phenylbutyric acid, 3-p-tolylpropanoic acid, 3-thiophenecarboxylic acid, 4-(1,3-dioxoisoindolin-2-yl)-2-hydroxybutanoic acid, 4-(2,4,5-trichlorophenoxy)-butyric acid, 4-(2,4-dichlorophenoxy)-butyric acid, 4-(2,4-di-tert-pentylphenoxy)butyric acid, 4-(2-phenoxyethoxy)benzoic acid, 4-(3,4-dimethoxyphenyl)-butyric acid, 4-(4-methoxyphenyl)butyric acid, 4-(4-nitrophenyl)butyric acid, 4-(diethylamino)benzoic acid, 4-(dimethylamino)cinnamic acid, 4-(dimethylamino)phenyl-acetic acid, 4-(ethylthio)benzoic acid, 4-(hydroxymethyl)benzoic acid, 4-(methylsulfonyl)benzoic acid, 4-(methylthio)benzoic acid, 4-(methylthio)phenylacetic acid, 4-(trifluoromethoxy)benzoic acid, 4'-(trifluoromethyl)biphenyl-2-carboxylic acid, 4-(trifluoromethyl)mandelic acid, 4,4,4-trifluoro-3-methyl-2-butenoic acid, 4,4-bis-(4-hydroxyphenyl)-valeric acid, 4,5-dimethoxy-2-nitrobenzoic acid, 4,6-dioxoheptanoic acid, 4-[4-(2carboxybenzoyl)-phenyl]butyric acid, 4-acetamidobenzoic acid, 4-acetylbenzoic acid, 4-acetylphenoxyacetic acid, 4-benzyloxy-3-methoxyphenyl-acetic acid, 4-biphenylacetic acid, 4-bromo-3,5-dihydroxy-benzoic acid, 4-bromobenzoic acid, 4-bromocinnamic acid, 4-bromophenylacetic acid, 4-butoxybenzoic acid, 4-butoxyphenylacetic acid, 4-butylbenzoic acid, 4-chloro-2,5-difluorobenzic acid, 4-chloro-3sulfamoylbenzoic acid, 4-chlorobenzoic acid, 4-chlorootolyloxyacetic acid, 4-chlorophenylacetic acid, 4-chlorosalicylic acid, 4-ethoxycarbonyloxy-3,5-dimethoxybenzoic acid, 4-ethoxyphenylacetic acid, 4-ethylbenzoic acid, 4'-ethylbiphenyl-4-carboxylic acid, 4-fluorenecarboxylic acid, 4-fluoro-1-naphthoic acid, 4-fluoro-2-(trifluoromethyl)-benzoic acid, 4-fluoro-3-nitrobenzoic acid, 4-fluorobenzoic acid, 4-fluorobenzoic acid, 4-fluorocinnamic acid, 4-fluorophenoxyacetic acid, 4-heptyloxybenzoic acid, 4-hexylbenzoic acid, 4-hexyloxybenzoic acid, 4-hydroxy-3 (morpholino-methyl)benzoic acid hydrate, 4-hydroxy-3,5-dinitrobenzoic acid, 4-hydroxy-3-methoxy-benzoic acid, 4-hydroxy-3-methoxy-mandelic acid, 4-hydroxy-3-nitrobenzoic acid, 4-hydroxy-3-nitrophenylacetic acid, 4-hydroxybenzoic acid, 4'-hydroxybiphenyl-4-carboxylic acid, 4-hydroxyphenylacetic acid, 4-hydroxyphenylacetic acid, 4-hydroxyphenylpyruvic acid, 4-iodobenzoic acid, 4-isopropoxybenzoic acid, 4-methoxy-3-nitrobenzoic acid, 4-methoxycyclohexane-carboxylic acid, 4-methoxysalilcyclic acid, 4-methyl-1-cyclohexane-carboxylic acid (cis and trans), 4-methyl-3-nitrobenzoic acid, 4-methylhippuric acid, 4-methylsalicyclic acid, 4-methylvaleric acid, 4-nitro-3-pyrazolecarboxylic acid, 4-nitrohippuric acid, 4-nonyloxybenzoic acid, 4-octylbenoic acid, 4-oxo-4H-1-benzopyran-2-carboxylic acid, 4-oxo-6-phenyl-5-hexenoic acid, 4-pentenoic acid, 4-pentylbenzoic acid, 4-pentylbicyclo[2.2.2]octane-1-carboxylic acid, 4-pentyloxybenzoic acid, 4-pentynoic acid, 4-phenylbutyric acid, 4-Propoxybenzoic acid, 4-propylbenzoic acid, 4-pyrazolecarboxylic acid, 4-tert-butylbenzoic acid, 4-tert-butylcyclohexanecarboxylic acid, 4-vinylbenzoic acid, 5-(4-chlorophenyl)-2-luroic acid, 5,6-dichloronicotinic acid, 5-bromo-2,4-dihydroxybenzoic acid, 5-fluoro2-methylbenzoic acid, 5-fluoroindole-2-carboxylic acid, 5-fluorosalicylic acid, 5-hydantoinacetic acid, 5-hydroxy-2indole-carboxylic acid, 5-methoxy-1-indanone-3-acetic acid, 5-methoxy-2-methyl-3-indoleacetic acid, 5-methoxy-2-nitrobenzoic acid, 5-methoxysalicylic acid, 5-methyl-2-nitrobenzoic acid, 5-methyl-2-pyrazine-carboxylic acid, 5-nitro-2-furoic acid, 5-nitro-3-pyrazolecarboxylic acid, 5-phenylvaleric acid, 6-(carbobenzyloxyamino)-caproic acid, 6-acetamidohexnoic acid, 6-bromohexanoic acid, 6-chloronicotinic acid, 6-hydroxy-2,5,7,8-tetramethylchroman-2-carboxylic acid, 6-methylchromone-2-carboxylic acid, 6-methylnicotinic acid, 6-nitrocaproic acid, 6-oxoheptaoic acid, 6-phenylhexanoic acid, 7-(carboxymethyoxy)-4methylcoumarin, 7-hydroxycoumarin-4-acetic acid, 7-methoxy-2-benzofuran-carboxylic acid, 7-methoxycoumarin-4-acetic acid, 7-oxoctanoic acid, 9-anthracenecarboxylic acid, 9-fluoreneacetic acid, 9-fluorenone-1-carboxylic acid, a,a,a-trifluoro-m-toluic acid, a-acetamidocinnamic acid, abietic acid, acetic acid, acetic acid, acetic acid, acetyl-L-asparagine, acetylsalicyclic acid, acetylsalicylic acid, a-cyano-4-hydroxycinnamic acid, adipic acid monoethyl ester, a-hydroxyhippuric acid, anthranilic acid, anti-3-oxotricyclo [2.2.1.02,6]heptane-7-carboxylic acid, a-phenylcyclopentaneacetic acid, a-phenyl-o-toluic acid, atrolactic acid, benzilic acid, benzotriazole-5-carboxylic acid, benzoylformic acid, bis(4-chlorophenyl)acetic acid, carbobenzyloxy-DL-alanine, carbobenzyloxy-L-alanine, carbobenzyloxy-L-glutamine, carbobenzyloxy-L-valine, cis-2-methoxycinnamic acid, crotonic acid, cyclohexanebutyric acid, cyclohexanecarboxylic acid, cyclohexanepentanoic acid, cyclohexanepropionic acid, cyclopentylacetic acid, D,L-3,4-dihydroxymandelic acid, D-3-phenyllacetic acid, decanoic acid, dicyclohexylacetic acid, diethylphosphonoacetic acid, dikegulac hydrate, diphenylacetic acid, fumaric acid monoethyl ester, fusaric acid, gallic acid, geranic acid, glycolic acid, heptadecafluorononanoic acid, heptanoic acid, hexanoic acid, hippuric acid, hydrocinnamic acid, indole-3-carboxylic acid, indole-4-carboxylic acid, isovaleric acid, L-3-phenyllacetic acid, lauric acid, L-lactic acid, maleamic acid, methoxyacetic acid, mono-(1R)-(−)-menthyl phthalate, mono-(1S)(+)-menthyl phthalate, mono-methyl cis-5-norbomeneendo-2,3-dicarboxylate, mono-methyl phthalate, monomethylterephthalate, N-(2-furoyl)glycine, n-(3,5dinitrobenzoyl)-DL-a-phenylglycine, N-(3-indolylacetyl) N-alanine, N-(3-indolylacetyl)-L-isoleucine, N-(3-indolylacetyl)-L-leucine, N-(3-indolylacetyl)-L-phenylalanine, N-(3-indolylacetyl)-L-valine, N-(carbobenzyloxy)-L-phenyl-alanine, N,N-diethyl-3,6-difluoro-phthalamic acid, Ni[(R)-1-(1-naphthyl)ethyl]-phthalamic acid, N-[5-(trifluoromethyl)-2-pyridyl]-L-valine, n-acetyl-4-fluoro-DL-phenylalanine, N-acetyl-DL-tryptophan, n-acetyl-L-leucine, N-acetyl-L-methionine, N-acetyl-L-phenylalanine, N-acetyl-L-phenylalanine, N-acetyl-L-tyrosine, N-benzoyl-(2R,3S)-3-phenyl-isoserine, N-benzoylL-threonine, N-carbobenzyloxy-2-methyl-alanine, N-carbobenzyloxy-L-glutamic acid-1-methyl ester, N-carbobenzyloxy-L-isoleucine, N-carbobenzyloxy-L-Leucine, N-carbobenzyloxy-1-threonine, N-ethoxycarbonyl-1-phenylalanine, nonanoic acid, N-p-tosylglycine, N-p-tosyl-L-phenylalanine, o-anisic acid, p-anisic acid, pentafluorobenzoic acid, phenoxyacetic acid, phenylacetic acid, podocarpic acid, pyruvic acid, rhodanine-3-acetic acid, S-(thiobenzoyl)thioglycolic acid, S-benzyl-N-carbobenzyloxy-1-cysteine, sebacic acid monomethyl ester, succinamic acid, succinic 2,2-dimethyl-hydrazide, tetrahydro-2-furoic acid, trans-1-acetyl-4-hydroxy-L-proline, trans-2,3-dimethoxycinnamic acid, trans-2,4-dichlorocinnamic acid, trans-2,4-difluorocinnamic acid, trans-2,5-difluorocinnamic acid, trans-2,6-difluorocinnamic acid, trans-2-chloro-6-fluoro-cinnamic acid, trans-2-hexenoic acid, trans-3-(2,3,5,6-tetramethyl-benzoyl)acrylic acid, trans-3-(2,5-dimethyl-benzo-yl)-acrylic acid, trans-3-(4-ethoxy-benzoyl)acrylic acid, trans-3-(4-methoxybenzoyl)-acrylic acid, trans-3-(4-methylbenzoyl)-acrylic acid, trans-3,4-difluorocinnamic acid, trans-3-fluorocinnamic acid, trans-3-furanacrylic acid, trans-3-hexenoic acid, trans-4-chloro-3-nitrocinnamic acid, trans-4-hydroxy-3-methoxy-cinnamic acid, trans-4-hydroxy-3-methoxy-cinnamic acid, trans-4-methyl-1-cyclohexane carboxylic acid, trans-4-pentylcyclohexane carboxylic acid, trans-5-bromo-2-methoxy cinnamic acid, trans-styrylacetic acid, tridecafluoroheptanoic acid, trimethylacetic acid, triphenylacetic acid, valeric acid and yohimbinic acid.

In some embodiments, moieties $R^1$ and $R^2$ are the same or different and each individually is an acyl group of a benzoic acid, wherein the benzoic acid may be substituted with one or more moieties selected from the group consisting of halogen, $C_1$-$C_5$ alkyl, and $C_1$-$C_5$ alkoxy, and moiety $R^3$ is an acyl group of a phenylacetic acid, wherein the phenylacetic acid may be substituted with one or more moieties selected from the group consisting of halogen, hydroxyl, $C_1$-$C_5$ alkyl, and $C_1$-$C_5$ alkoxy.

In another aspect, there are provided methods of treating an individual with a physiological disease, disorder, or condition associated with inappropriate activity of a protein tyrosine phosphatase comprising the step of administering to the individual a therapeutically effective amount of a pharmaceutical compound of Formula A. In some embodiment the disease, disorder, or condition is selected from the group consisting of type 1 diabetes, type 2 diabetes, obesity, metabolic syndrome, Crohn's disease, rheumatoid arthritis, Graves' disease, systemic lupus erythematosus, leukemia, and tuberculosis. In some embodiments the pharmaceutical compound is a PTP inhibitor, such as a selective PTP-MEG2 inhibitor.

Also provided are methods for altering the activity of at least one PTP enzyme by contacting a cell with at least one of the compounds of Formula A. In some embodiments the cell is either a human or an animal cell. In some embodiments the cell is a CD4+ T-cells derived from a human. In some embodiments the compound preferentially reduces the activity of the tyrosine phosphatase PTP-MEG2. In representative embodiments, moieties $R^1$, $R^2$, and $R^3$ of the compound of Formula A are the same or different and each individually is an acyl group of a benzoic acid, wherein the benzoic acid may be substituted with one or more moieties selected from the group consisting of halogen, hydroxyl, $C_1$-$C_5$ alkyl, and $C_1$-$C_5$ alkoxy.

Other embodiments include methods of treating a patient, comprising the steps of: identifying a patient having type 2 diabetes; providing a compound having the structure of Compound 7:

Compound 7

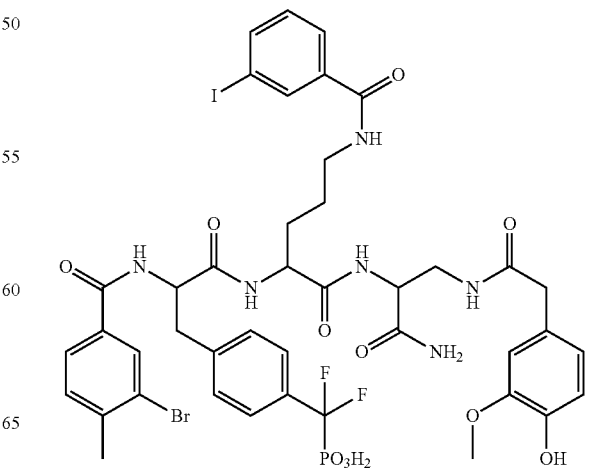

and administering a therapeutically effective amount of the compound to the patient. In some embodiments, the patient may be a human.

In another aspect, use of a compound of Formula A, a therapeutically suitable prodrug thereof, or a therapeutically suitable salt thereof for treating a disease, disorder, or condition associated with inappropriate activity of a protein tyrosine phosphatase is provided. In some embodiment the disease, disorder, or condition is selected from the group consisting of type 1 diabetes, type 2 diabetes, obesity, metabolic syndrome, Crohn's disease, rheumatoid arthritis, Graves' disease, systemic lupus erythematosus, leukemia, and tuberculosis. In some embodiments, the compound can be Compound 7, a therapeutically suitable prodrug thereof, or a therapeutically suitable salt thereof. In particular, the compound of Formula A (e.g. Compound 7) can be used for treating type 2 diabetes.

In another aspect, use of a compound of Formula A, a therapeutically suitable prodrug thereof, or a therapeutically suitable salt thereof in the manufacture of a medicament for the treatment of a disease, disorder, or condition associated with inappropriate activity of a protein phosphatase is provided. In some embodiment the disease, disorder, or condition is selected from the group consisting of type 1 diabetes, type 2 diabetes, obesity, metabolic syndrome, Crohn's disease, rheumatoid arthritis, Graves' disease, systemic lupus erythematosus, leukemia, and tuberculosis. In some embodiments, the compound can be Compound 7, a therapeutically suitable prodrug thereof, or a therapeutically suitable salt thereof. In particular, the compound of Formula A (e.g. Compound 7) can be used in the manufacture of a medicament for the treatment of type 2 diabetes.

In another aspect, use of a compound of Formula A, a therapeutically suitable prodrug thereof, or a therapeutically suitable salt thereof for inhibiting a protein tyrosine phosphatase enzyme is provided. In some embodiments, the protein phosphatase enzyme is located in a human cell or an animal cell. In some embodiments the compound preferentially reduces the activity of the tyrosine phosphatase PTP-MEG2. In representative embodiments, moieties $R^1$, $R^2$, and $R^3$ of the compound of Formula A are the same or different and each individually is an acyl group of a benzoic acid, wherein the benzoic acid may be substituted with one or more moieties selected from the group consisting of halogen, hydroxyl, $C_1$-$C_5$ alkyl, and $C_1$-$C_5$ alkoxy. In particular, the compound of Formula A (e.g. Compound 7) can be used for inhibiting a protein tyrosine phosphatase enzyme (e.g. PTP-MEG2) in either a human or an animal cell.

In another aspect, a pharmaceutical composition of comprising a compound of formula A, a therapeutically suitable prodrug thereof, or a therapeutically suitable salt thereof and a pharmaceutically acceptable carrier is provided. In some embodiments, a compound of Formula A, e.g. Compound 7, may be provided as a pharmaceutical compound in a pharmaceutical formulation for medicinal applications, comprising the compound and a pharmaceutically acceptable carrier therefor. Representative pharmaceutical formulations include those suitable for oral, parenteral (including subcutaneous, intradermal, intramuscular and intravenous) and rectal administration. The formulations may be presented in unit dosage form and may be prepared by any of the methods well known in the art of pharmacy. Usually, the formulations are prepared by uniformly and intimately bringing into association the active ingredient with a liquid carrier, or a finely divided solid carrier, or both, and then, if necessary, forming the associated mixture into the desired formulation.

Pharmaceutical formulations suitable for oral administration may be presented as discrete units, such as a capsule, cachet, tablet, or lozenge, each containing a predetermined amount of the active ingredient; as a powder or granules; as a solution or a suspension in an aqueous liquid or a non-aqueous liquid such as a syrup, elixir or a draught, or as an oil-in-water liquid emulsion or a water-in-oil liquid emulsion. The formulation may also be a bolus, electuary or paste.

A tablet may be made by compressing or molding a pharmaceutical compound with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating agent and/or a surface active agent. Molded tablets may be prepared by molding in a suitable machine a mixture of the powdered active ingredient moistened with an inert liquid diluent. The tablets may optionally be coated or scored and may be formulated so as to provide slow or controlled release of the active ingredient.

Formulations suitable for parenteral administration include aqueous and non-aqueous sterile injection solutions, and may also include an antioxidant, buffer, a bacteriostat and a solution which renders the composition isotonic with the blood of the recipient, and aqueous and non-aqueous sterile suspensions which may contain, for example, a suspending agent and a thickening agent. The formulations may be presented in single unit-dose or multi-dose containers, and may be stored in a lyophilized condition requiring the addition of a sterile liquid carrier prior to use.

As intended herein, the terms "a" and "an" include singular as well as plural references unless the context clearly dictates otherwise. For example, the term "a PTP inhibitor" can include one or more such inhibitors.

"Treatment" as used herein includes the alleviation, prevention, reversal, amelioration or control of a pathology, disease, disorder, process, condition or event, such as diabetes. In this context, the term "treatment" is further to be understood as embracing the use of a drug to inhibit, block, reverse, restrict or control progression of a disease, disorder, or condition associated with inappropriate activity of a protein phosphatase.

As used herein, the terms "pharmaceutical compound," or "drug" refers to a free compound, its therapeutically suitable salts, solvates such as hydrates, specific crystal forms of the compound or its salts, or therapeutically suitable prodrugs of the compound. More generally, the term "compound," when used in the context of pharmaceutical treatment, is meant to refer to the free compound, its therapeutically suitable salts, solvates such as hydrates, specific crystal forms of the compound or its salts, or therapeutically suitable prodrugs of the compound.

As used herein, the terms "pharmaceutical composition" and "pharmaceutical formulation" refer to compositions of matter comprising at least one pharmaceutical compound.

The term "therapeutically suitable salt," refers to salts or zwitterions of pharmaceutical compounds which are water or oil-soluble or dispersible, suitable for treatment of disorders and effective for their intended use. The salts may be prepared, for instance, during the final isolation and purification of the compounds or separately by reacting an amino group of the compounds with a suitable acid. For example, a compound may be dissolved in a suitable solvent, such as but not limited to methanol and water, and treated with at least one equivalent of an acid, for instance hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of a compound may also be quaternized with alkyl chlorides, bromides, and iodides such as methyl, ethyl, propyl, isopropyl, butyl, lauryl, myristyl, stearyl, and the like.

Basic addition salts may be prepared, for instance, during the final isolation and purification of pharmaceutical compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine Quaternary amine salts may derived, for example, from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like.

The term "therapeutically suitable prodrug," refers to those prodrugs or zwitterions which are suitable for use in contact with the tissues of subjects and are effective for their intended use. The term "prodrug" refers to compounds that are transformed in vivo to a pharmaceutical compound, for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The expression "pharmaceutically acceptable carrier" as used herein in relation to the carrier is used in the sense of being compatible with a pharmaceutical compound in a pharmaceutical formulation and with any other therapeutic agent that may be present, and not being detrimental to the recipient thereof. The carrier itself may constitute one or more excipients conventionally used in the art of pharmacy that enable the pharmaceutical compound and any other therapeutic agent that may be present, to be formulated as a pharmaceutical formulation.

The terms "pharmaceutically effective amount" and "effective amount", as used herein, refer to an amount of a pharmaceutical formulation that will elicit the desired therapeutic effect or response when administered in accordance with the desired treatment regimen.

As used herein, "inhibition" or "inhibitory activity" each encompass whole or partial reduction of activity or effect of an enzyme.

As used herein, the term "acyl group of a carboxylic acid" refers to a moiety of formula R—C(O)— which, for naming purposes, is referred to as the "acyl group of R—C(O)—OH," the structure of moiety R being dependent on the given carboxylic acid of formula R—C(O)—OH. One should bear in mind, however, that, within the context of a molecule featuring such an acyl group, the R—C(O)— need not necessarily have originally been part of a carboxylic acid. For example, the R—C(O)— may have been added by reacting a precursor of the molecule with another type of R—C(O)— precursor, such as R—C(O)—Cl.

A "selective" PTP inhibitor is one that has at least 2, 5, 10, 20, 50, 100, or 200 fold greater inhibitory activity (for example, as determined by calculation of IC50, or other measure of affinity or effect) for a particular isozyme of PTP compared to other members of the PTP enzyme family. For example, a selective PTP-MEG2 inhibitor is a compound that has at least 2, 5, 10, 20, 50, or 100 fold greater activity (determined by calculation of $K_i$) at PTP-MEG2 compared to PTP1B. The term "associated with inappropriate activity of a protein tyrosine phosphatase" encompasses all diseases, disorders, or conditions in which symptoms are in part related to excessive activity of a protein tyrosine phosphatase or deficient activity of a protein tyrosine kinase, as compared to the activity of the protein tyrosine phosphatase of a subject without such diseases, disorders, or conditions.

The disclosure will be more fully understood upon consideration of the following non-limiting Examples.

EXAMPLES

Acquisition of a potent and selective PTP-MEG2 inhibitor. FIG. 1 depicts a stepwise fluorophore-tagged focused library synthesis and competitive fluorescence polarization screening approach for the acquisition of PTP-MEG2 inhibitory agents that are capable of binding both the active site and adjacent peripheral sites. The library precursor 2a contains the following features: (1) the $F_2Pmp$ active site-targeting moiety; (2) a free amine from ornithine (i.e. the —NH—X moiety) positioned on the C-terminal side of $F_2Pmp$ that can be modified to incorporate molecular diversity, and (3) a fluorescein tag linked through a β-Ala-Lys spacer (i.e. the -βAlaLys(Fluorescein) moiety). The fluorophore, an integral part of the library, enables in situ homogeneous, high-throughput fluorescence polarization displacement assays to identify high affinity active site binders (Zhang, et al., *J. Am. Chem. Soc.* 2009, 131, 13072-13079).

Precursor 2a was prepared using solid phase peptide synthesis with Fmoc chemistry (FIG. 12) and purified by HPLC. Library 2b was constructed by condensing the free amine from ornithine in 2a with 576 different carboxylic acids listed hereinabove (see U.S. Published Patent Appl. No. 2012/0088720) (FIG. 1). These carboxylic acids vary in size, functionality, charge, polarity, and hydrophobicity and therefore provide structural diversity to increase the number and strength of noncovalent interactions believed to be formed with the P+1 pocket immediately C-terminal to the active site in PTP-MEG2. The 576 structurally diverse carboxylic acids were introduced, in equal quantities, into individual wells of six 96-well plates, along with appropriate reagents to activate the acid functionality. Compound 2a was then added to each well to commence condensation. The reaction was quenched with cyclohexylamine, and the resulting library (2b) diluted and dispensed into 384-well plates for FP-based screening.

Figure 6:
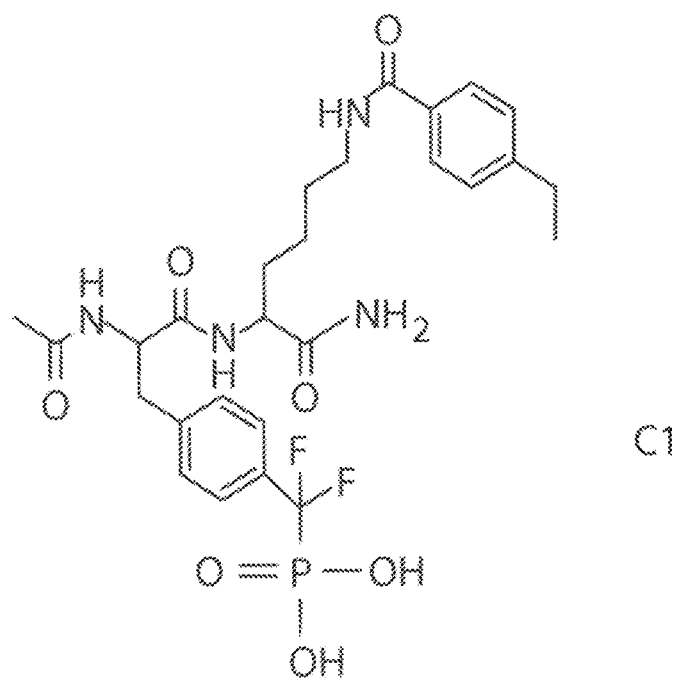
FIG. 6 depicts the structure of compound C1.

To identify PTP-MEG2 inhibitors, the fluorescein tagged library 2b (~3 nM) was mixed with 2 µM PTP-MEG2, and the anisotropy values (measures of binding affinity) were determined with a microplate reader both in the absence and presence of 20 µM Compound C1 (FIG. 6), a competitive inhibitor of PTP-MEG2 with an $IC_{50}$ of 9.0 µM. The fluorescein-labeled compounds most resistant to displacement by Compound C1 are expected to possess the highest affinity for PTP-MEG2. The top ten binders are listed in Table S1.

TABLE S1

Hits from the Library 2b

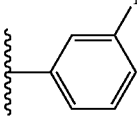

| R Group | Affinity rank |
|---|---|
| 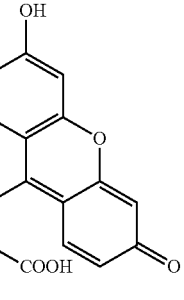 | 1 |
| 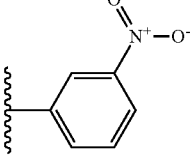 | 2 |
| 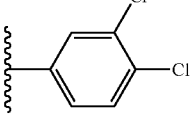 | 3 |
| 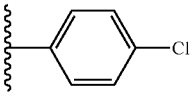 | 4 |
| 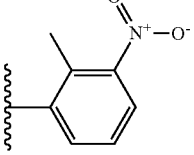 | 5 |

TABLE S1-continued
Hits from the Library 2b
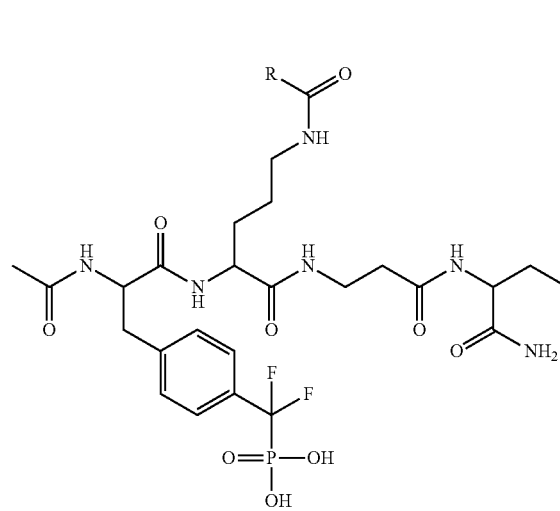
| R Group | Affinity rank |
|---|---|
| 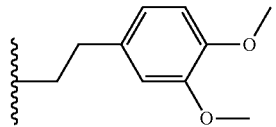 [SMILES: *CCc1ccc(OC)c(OC)c1] | 6 |
| 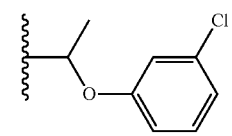 [SMILES: *C(C)Oc1cccc(Cl)c1] | 7 |
| 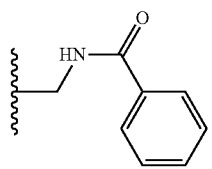 [SMILES: *CNC(=O)c1ccccc1] | 8 |
| 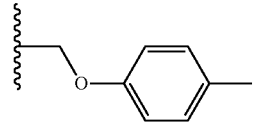 [SMILES: *COc1ccc(C)cc1] | 9 |
| 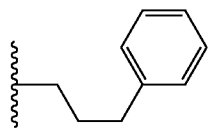 [SMILES: *CCCc1ccccc1] | 10 |

The top five compounds are all benzoic acid derivatives with substitution at the meta and/or para positions. The lead Compound 3 was re-synthesized without the fluorescein tag and evaluated for its ability to inhibit the PTP-MEG2 catalyzed p-nitrophenyl phosphate (pNPP) hydrolysis. The $IC_{50}$ of 3 for PTP-MEG2 is 0.90±0.02 μM, which is 8.7-fold lower than that for PTP1B (7.8±0.1 μM). These results are impressive since $F_2$Pmp binds PTP1B ($IC_{50}$=0.5 mM) 23-fold tighter than it does to PTP-MEG2 ($IC_{50}$=11.5 mM). Apparently, the additional interactions between Compound 3 and PTP-MEG2's P+1 pocket are sufficient to overcome the inherently weaker interactions afforded by the pTyr surrogate $F_2$Pmp toward the active site.

Next, the α-amino group from $F_2$Pmp in Compound 4a (FIG. 1, Y=H) was condensed with the same set of 576 carboxylic acids to furnish the second-generation library (4b). Introduction of diversity at the D-amino position of $F_2$Pmp maximizes interactions of library components with the P−1 sub-pocket immediately N-terminal to the pTyr-binding site in PTP-MEG2. The library was screened as described above using Compound 3 as the displacement agent. A number of hits were identified based on PTP-MEG2 binding affinity (Table S2) and the one with the highest affinity (Compound 5) was re-synthesized. Compound 5 displayed an $IC_{50}$ of 0.27±0.07 μM for PTP-MEG2, a 3.3-fold improvement over Compound 3 in potency and 12.6-fold selectivity against PTP1B ($IC_{50}$=3.4±0.08 μM).

TABLE S2

Hits from the Library 4b

| R Group | Affinity rank |
| --- | --- |
| 3-bromophenyl | 1 |
| 3-iodo-4-methylphenyl | 2 |
| 3-iodo-5-bromophenyl | 3 |

TABLE S2-continued
Hits from the Library 4b
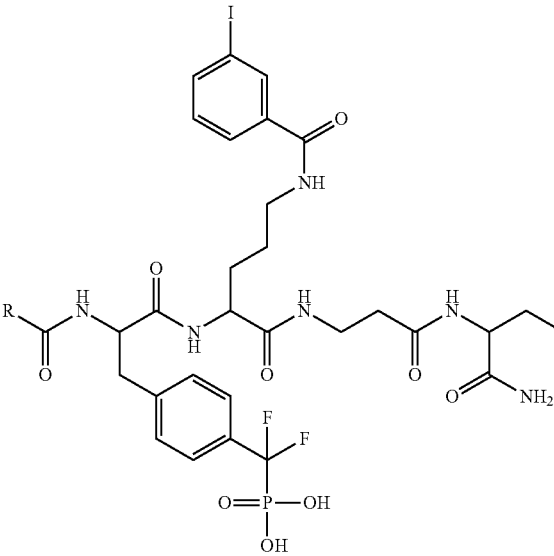
| R Group | Affinity rank |
|---|---|
| 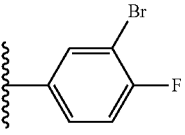 | 4 |
| 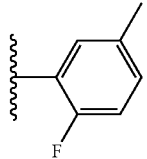 [SMILES: *c1cc(C)ccc1F] | 5 |
| 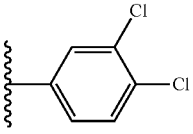 | 6 |
| 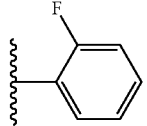 | 7 |

TABLE S2-continued

Hits from the Library 4b

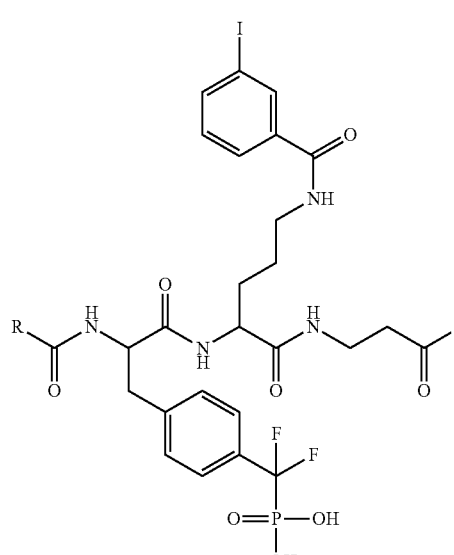

| R Group | Affinity rank |
|---|---|
| 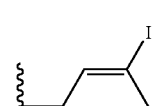 | 8 |
| 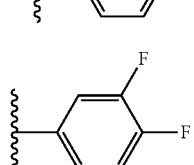 | 9 |
| 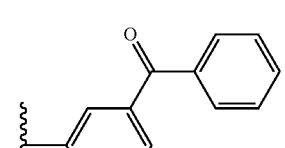 | 10 |

Figure 2:
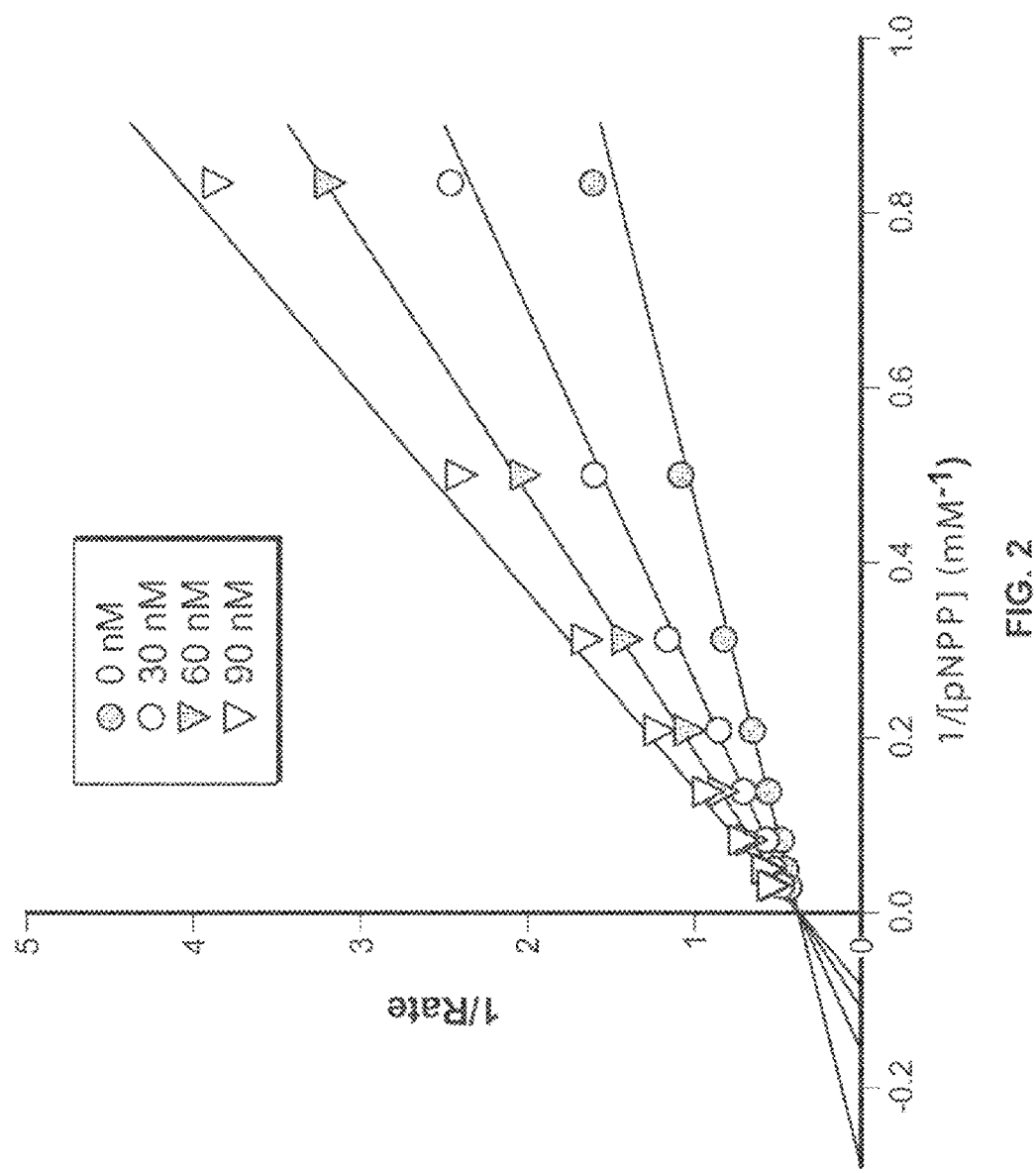
FIG. 2 depicts a Lineweaver-Burk plot for Compound 7-mediated PTP-MEG2 inhibition. Compound 7 concentrations at 0, 30, 60, and 90 nM were studied.

To further improve potency and selectivity, Compound 6a (FIG. 1, Z=H) was prepared by attaching a diaminopropionic acid (Dap) to 5 at the P+2 position thus enabling the capture of additional interactions with PTP-MEG2. The free amine on the Dap moiety was condensed with the same set of 576 carboxylic acids to furnish the third generation library 6b (FIG. 1), which was screened using Compound 5 as displacement agent. The top hits are listed in Table S3, most of which are derivatives of 4-hydroxyphenylacetic acid. The best hit (Compound 7) inhibited the PTP-MEG2 reaction with an $IC_{50}$ of 75±10 nM. Kinetic analysis revealed that Compound 7 is a reversible and competitive inhibitor for PTP-MEG2 with a $K_i$ of 34±2 nM (FIG. 2). It displays more than 10-fold selectivity over PTP1B ($IC_{50}$=0.86 µM) and TC-PTP ($IC_{50}$=0.83 µM), and shows no inhibition at 10 µM against a panel of mammalian PTPs, including cytosolic PTPs, PTP-MEG1, SHP1, SHP2, Lyp, FAP-1, PTP-PEST, PTPH1, Laforin, and HePTP, the receptor-like PTPs, CD45, LAR, DEP1, PTPµ, PTPγ, PTPβ, and PTPε, and the dual specificity phosphatases VHR and VHX (Table 1).

TABLE S3
Hits from the Library 6b
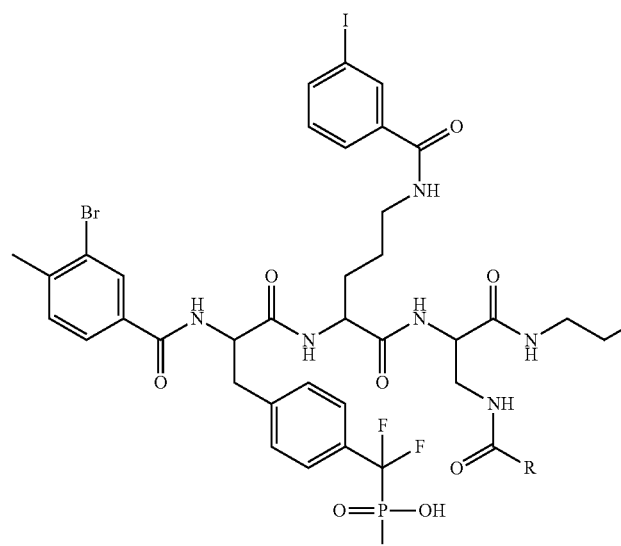
| R Group | Affinity rank |
|---|---|
| 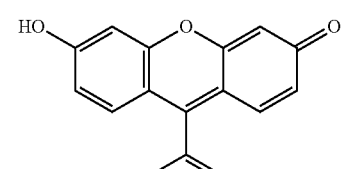 | 1 |
| 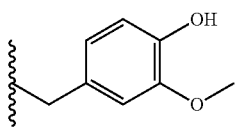 [SMILES: *Cc1ccc(O)c(OC)c1] | 2 |
| 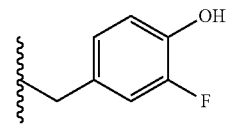 [SMILES: *Cc1ccc(O)c(F)c1] | 3 |
| 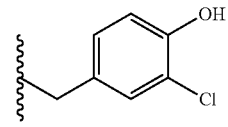 [SMILES: *Cc1ccc(O)c(Cl)c1] | 4 |
| 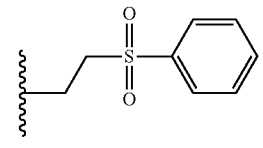 [SMILES: *CCS(=O)(=O)c1ccccc1] | 5 |
| 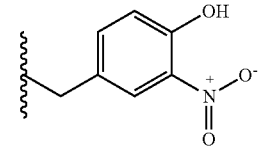 | 6 |

TABLE S3-continued
Hits from the Library 6b
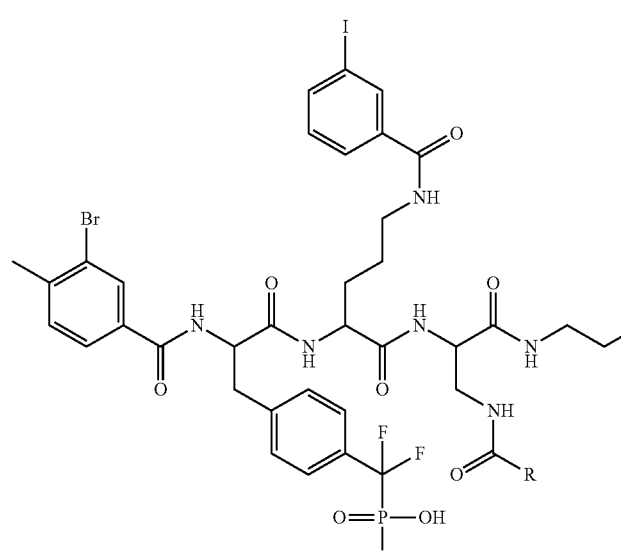
| R Group | Affinity rank |
|---|---|
| 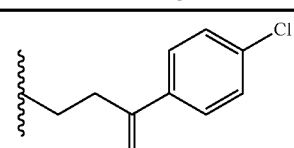 | 7 |
| 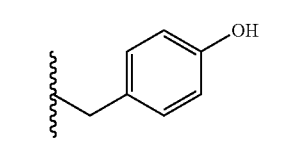 [SMILES: *Cc1ccc(O)cc1] | 8 |
| 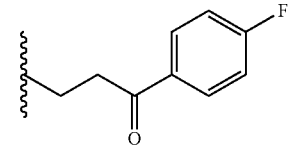 [SMILES: *CCC(=O)c1ccc(F)cc1] | 9 |
| 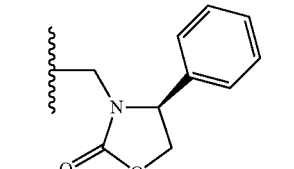 | 10 |
TABLE 1
Selectivity of Compound 7 against a Panel of PTPs
| PTP | $IC_{50}$ (nM) |
|---|---|
| PTP-MEG2 | 75, ($K_i$ = 34 nM) |
| TC-PTP | 830 |
| PTP1B | 860 |
| PTP-MEG1 | >10,000 |
| FAP1 | >10,000 |
| CD45 | >10,000 |
| LAR | >10,000 |
| SHP2 | >10,000 |
| HePTP | >10,000 |
| LYP | >10,000 |
| VHR | >10,000 |
| VHX | >10,000 |
| DEP1 | >10,000 |
| Laforin | >10,000 |
| PTPμ | >10,000 |
| PTP-PEST | >10,000 |
| PTPγ | >10,000 |

TABLE 1-continued

Selectivity of Compound 7 against a Panel of PTPs

| | |
|---|---|
| SHP1 | >10,000 |
| PTPH1 | >10,000 |
| PTPβ | >10,000 |
| PTPε | >10,000 |

Structural basis of PTP-MEG2 inhibition. To elucidate the structural basis of PTP-MEG2 inhibition and to aid the design of more potent and specific PTP-MEG2 probes, we determined the crystal structures of PTP-MEG2 catalytic domain (residues 277-582) in complex with Compounds 3, 5, and 7 by molecular replacement, using the apo-form of PTP-MEG2 catalytic domain (PDB #2PA5) (Barr, et al., Cell 2009, 136, 352-363) as the search model. The statistics of data collection and refinement are summarized in Table 2.

TABLE 2

Data collection and refinement statistics

| | PTP-MEG2•3 | PTP-MEG2•5 | PTP-MEG2•7 |
|---|---|---|---|
| Crystal Parameters space group | P1 | P1 | P1 |
| Cell Dimensions | | | |
| a (Å) | 39.98 | 40.26 | 40.14 |
| b (Å) | 57.75 | 57.17 | 57.77 |
| c (Å) | 66.54 | 66.42 | 66.70 |
| α (°) | 77.33 | 77.55 | 77.22 |
| β (°) | 78.28 | 78.23 | 78.03 |
| γ (°) | 80.27 | 79.97 | 80.01 |
| Data Collection | | | |
| resolution range (Å) | 50.0-1.24 | 50.0-1.76 | 50.0-1.24 |
| no. of unique reflections | 105301 | 52574 | 134008 |
| completeness (%) | 68.6 | 95.6 | 87.2 |
| redundancy | 1.8 | 2.4 | 2.1 |
| $R_{merge}$ $^a$ | 0.147 | 0.083 | 0.096 |
| Refinement | | | |
| resolution range (Å) | 50.0-1.8 | 50.0-2.0 | 50.0-1.4 |
| no. of reflections used | 44040 | 34622 | 100617 |
| completeness (%) | 84.3 | 91.3 | 90.1 |
| no. or protein atoms | 4816 | 4820 | 4902 |
| no. of inhibitors | 1 | 1 | 1 |
| no. of waters | 407 | 356 | 201 |
| $R_{work}$ $^b$/$R_{free}$ $^c$ | 18.9/22.5 | 18.7/22.3 | 19.8/21.5 |
| RMSD from Ideal Geometry | | | |
| bond length (Å) | 0.005 | 0.006 | 0.005 |
| bond angle (°) | 1.15 | 1.18 | 1.20 |
| Average B-factors (Å$^2$) | | | |
| overall | 22.73 | 27.89 | 22.40 |
| protein | 22.61 | 27.04 | 22.01 |
| inhibitor | 21.63 | 44.46 | 24.90 |
| waters | 24.26 | 37.18 | 31.23 |

$^a$ $R_{merg} = \Sigma_h\Sigma_i|I(h)I - <I(h)>|/\Sigma_h\Sigma_iI(h)_i$.
$^b$ $R_{work} = \Sigma_h|F(h)_{calcd} - F(h)_{obsd}|/\Sigma_hF(h)_{obsd}$, where $F(h)_{calcd}$ and $F(h)_{obsd}$ were the refined calculated and observed structure factors, respectively.
$^c$ $R_{free}$ was calculated for a randomly selected 3.4% (PTP-MEG2•3), 3.6% (PTP-MEG2•5) and 3.6% (PTP-MEG2•7) of the reflections that were omitted from refinement.

The final models for the PTP-MEG2 inhibitor complexes include all residues in PTP-MEG2 and all atoms of the inhibitors. Unambiguous electron densities are observed for Compounds 3, 5, and 7 as shown by the unbiased $F_o$–$F_c$ difference Fourier maps contoured at 3.0σ (FIG. 3A). The overall structure of PTP-MEG2•3 is similar to the unliganded PTP-MEG2 structure used for molecular replacement, with root mean square derivation (rmsd) for all Cα positions between the two being 0.456 Å. Moreover, the overall structures of PTP-MEG2•inhibitor complexes are also similar and the rmsd for all Cα positions is 0.411 Å between PTP-MEG2•3 and PTP-MEG2•5 and 0.367 Å between PTP-MEG2•3 and PTP-MEG2•7.

Figure 3B:
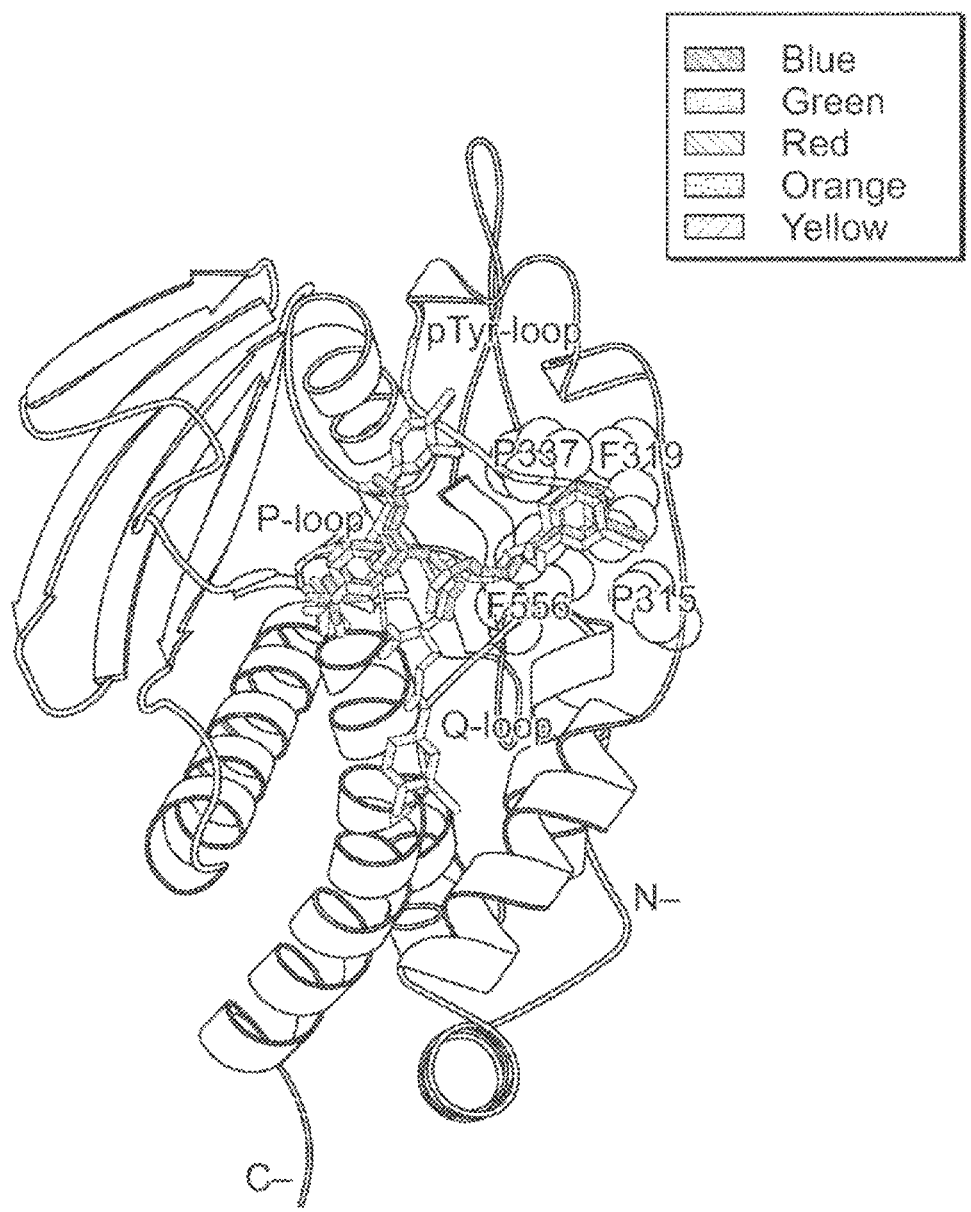
Figure 3C:
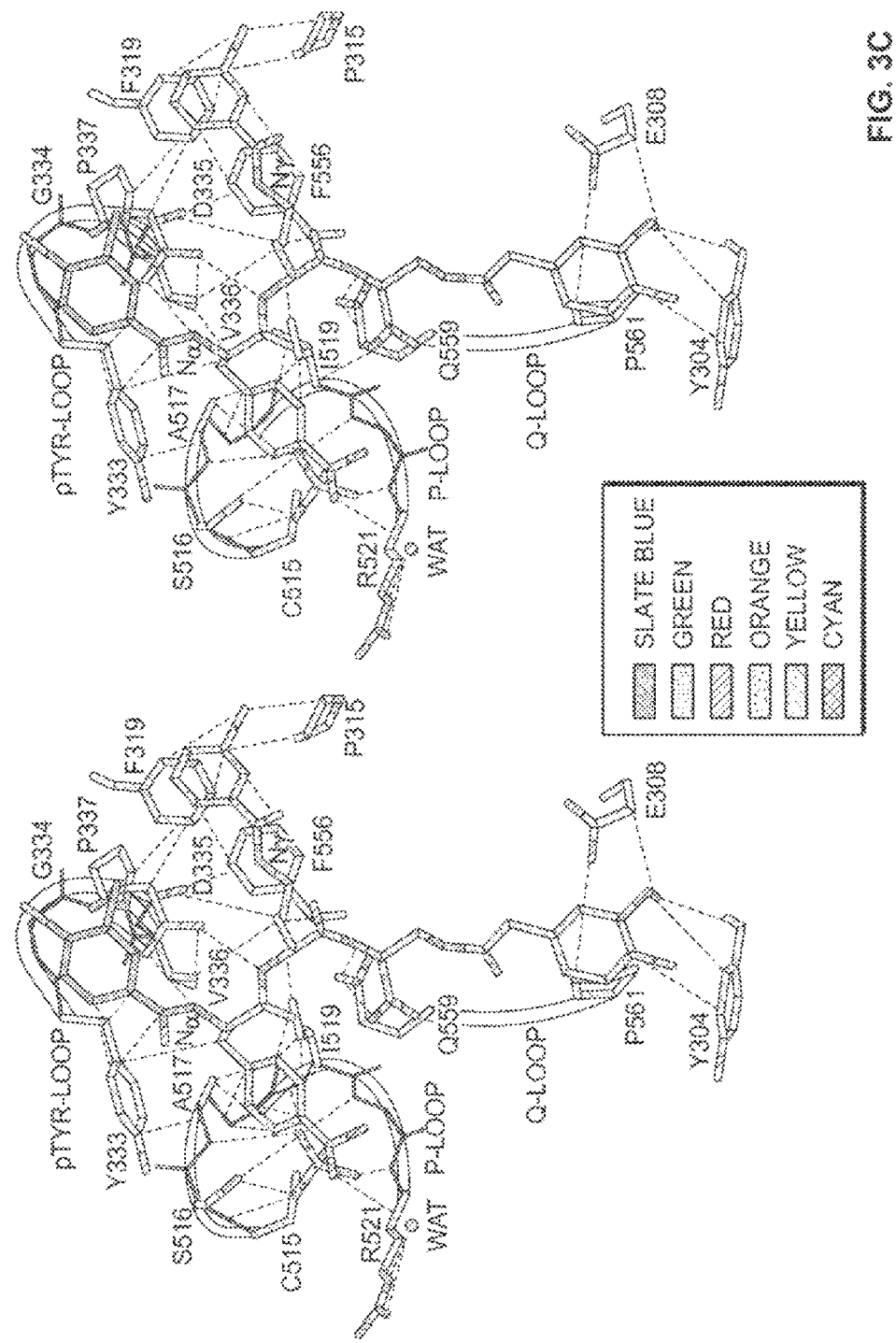

An overlay of the three crystal structures revealed that Compounds 3, 5, and 7 bind PTP-MEG2 with the same binding mode (FIG. 3B). Given the conservation of binding interactions between PTP-MEG2 and the shared components in Compounds 3, 5, and 7, the structure of PTP-MEG2•7 complex was refined to 1.4 Å resolution. As expected, F$_2$Pmp is found in the PTP-MEG2 active-site pocket and forms extensive interactions with residues in the P-loop (residues 514-521), the pTyr recognition loop (residues 331-338), and the Q-loop (residues 558-564) (FIG. 3C). Specifically, the phosphonate group appears to make six hydrogen bonds with the main chain amides of the P-loop and two polar interactions with the side chain of Ser516; one of the two fluorine atoms appears to form a polar interaction with the side-chain of Arg521 through a water molecule; and the Nα appears to provide 2H-bonds with Asp335. In addition to the polar interactions, the phenyl ring (including C$_\alpha$ and C$_\beta$) appears to participate in hydrophobic interactions with Tyr333 and Val336 in the pTyr loop and Van der Waals contacts with the aliphatic side chains of Gln559 in the Q-loop, and Ala517 and Ile519 in the P-loop.

Figure 3D:
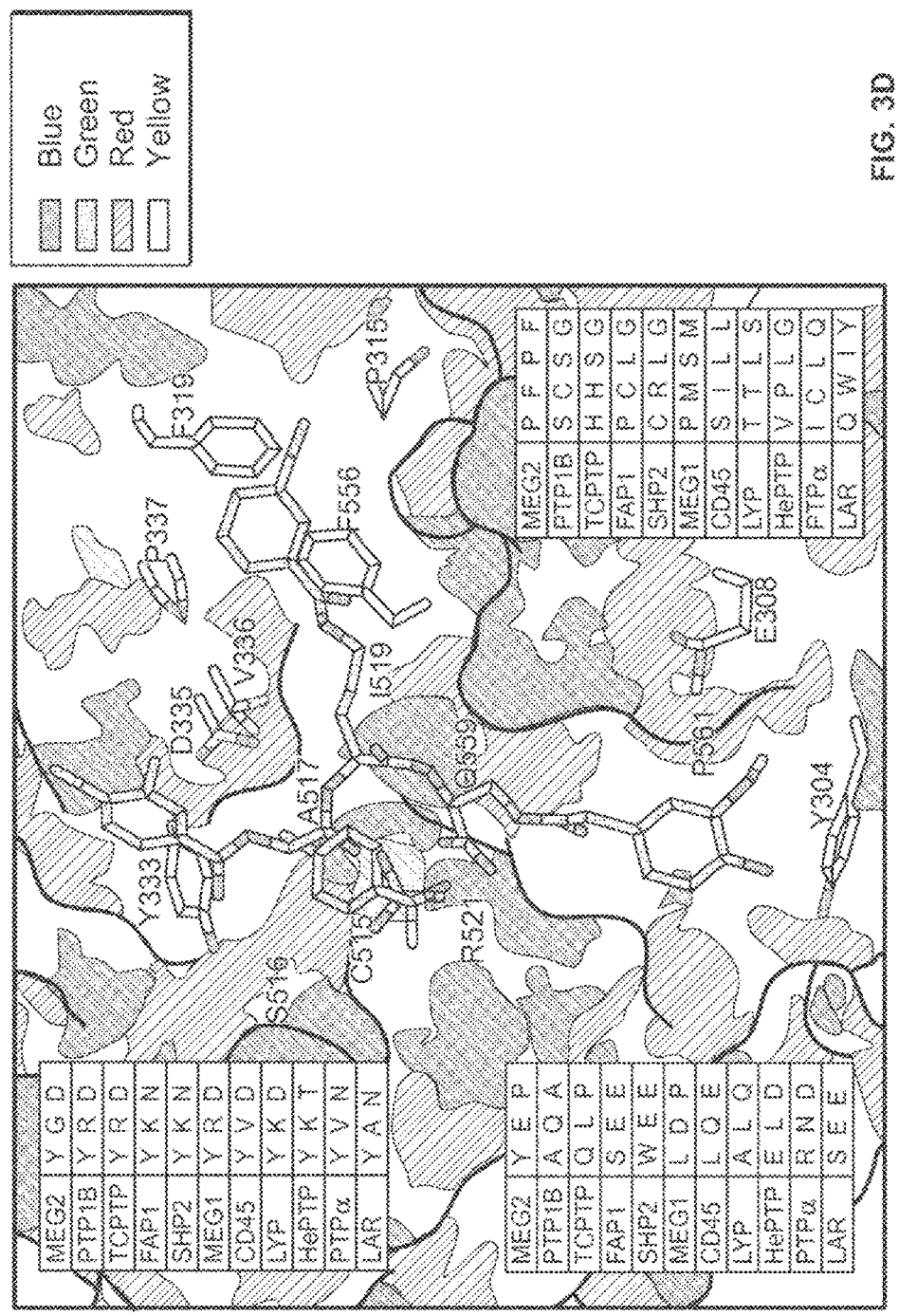
Figure 7:
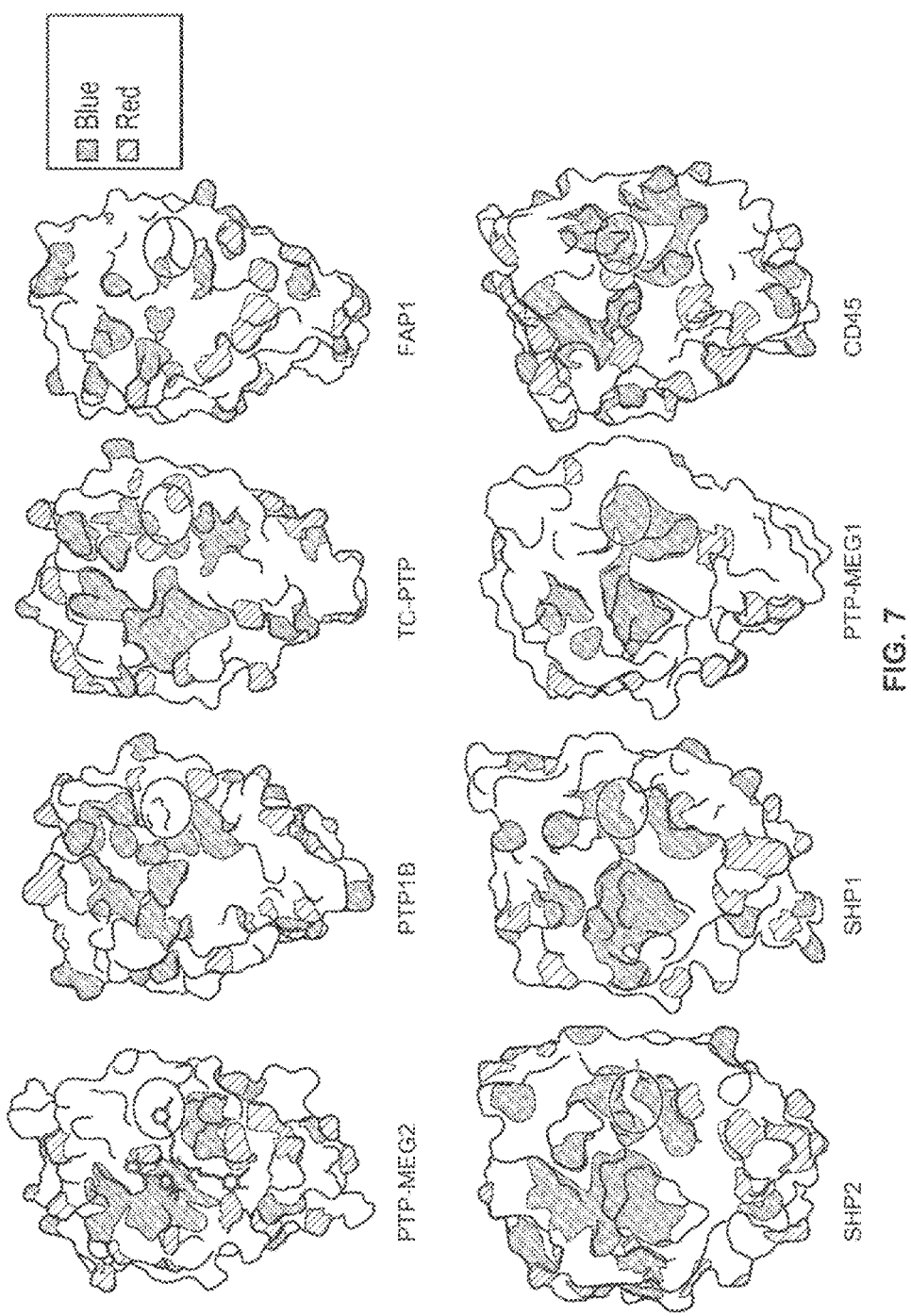
FIG. 7 shows that PTP-MEG2 has a unique binding site for the P+1 3-iodobenzoic amide moiety. Surface representations show the calculated electrostatic potential of PTP family members from their crystal structures. The molecule of compound 7 is also shown in the PTP-MEG2 structure, the binding site for the P+1 3-iodobenzoic amide moiety is marked by a circle; the corresponding area in other PTP members are also marked by a circle. The Figure was prepared by PyMol.

At the P+1 position, the ornithine linker appears to be involved in three polar interactions with Asp335 and Gln559 and several Van der Waals contacts with the side-chains of Val336, Asp335, Ile519, and Phe556. The 3-iodobenzoic amide moiety, attached to the Nγ of ornithine, sits above a hydrophobic patch formed by residues Pro315, Phe319, Pro337 and Phe556. The phenyl ring appears to be engaged in strong stacking interactions with the side chains of Pro315, Phe319, Pro337, Asp335, and Phe556, and the iodine makes additional nonpolar interactions with residues Pro315 and Phe319. Interestingly, the P+1 binding site (Pro315, Phe319, Pro337 and Phe556) for 3-iodobenzoic amide appears to be unique to PTP-MEG2 (FIG. 3D and FIG. 7) and is situated in close proximity to the second aryl phosphate-binding site originally identified in PTP1B (Puius, et al., Proc. Natl. Acad. Sci. USA 1997, 94, 13420-13245). Sequence alignment reveals that no other PTPs have the same four amino acids at the corresponding positions (FIG. 3D). Without being bound to any particular theory, it is likely that the stacking interactions between the 3-iodobenzoic amide group and the unique hydrophobic patch are responsible for Compound 3's impressive potency and selectivity for PTP-MEG2 (IC$_{50}$=0.90 μM) over PTP1B (IC$_{50}$=7.8 μM), despite F$_2$Pmp's preference for PTP1B (IC$_{50}$=0.5 mM) over PTP-MEG2 (IC$_{50}$=11.5 mM).

At the P−1 position, the 3-bromo-4-methylbenzoic amide group directly attached to the α-amino group of F$_2$Pmp is located near the pTyr recognition loop (FIG. 3C). Its phenyl ring appears to make contacts with residues Tyr333 and Asp335; the 4-methyl group appears to have nonpolar interactions with Asp335; and the bromine atom appears to form Van der Waals contacts with Gly334. These interactions are believed to increase the binding affinity of Compound 5 for PTP-MEG2 by 3.3-fold. Although Tyr333 and Asp335 in the pTyr-loop are well conserved among the PTPs (FIG. 3D), Gly334 is unique for PTP-MEG2, which may account for the increase in Compound 5's selectivity for PTP-MEG2 relative to PTP1B. At the P+2 position, the diaminopropionic acid linker is believed to make two polar interactions with the side-chain of Gln559, and the homovanillic amide group appears to be engaged in nonpolar interactions with residues Tyr304, Glu308 and Pro561. Interestingly, although these residues are fairly divergent among the PTPs (FIG. 3D), the interactions between the homovanillic amide group and residues Tyr304, Glu308 and Pro561 appear to contribute to a 3.6-fold increase in the affinity of Compound 7 but have little influence on inhibitor selectivity. Collectively, there is excellent agreement between the observed binding interactions and inhibition data for Compound 7. In addition, the structural observations provide direct evidence that Compound 7 achieves its potency and specificity for PTP-MEG2 by targeting unique nearby peripheral binding pockets in addition to the active site.

Figure 4A:
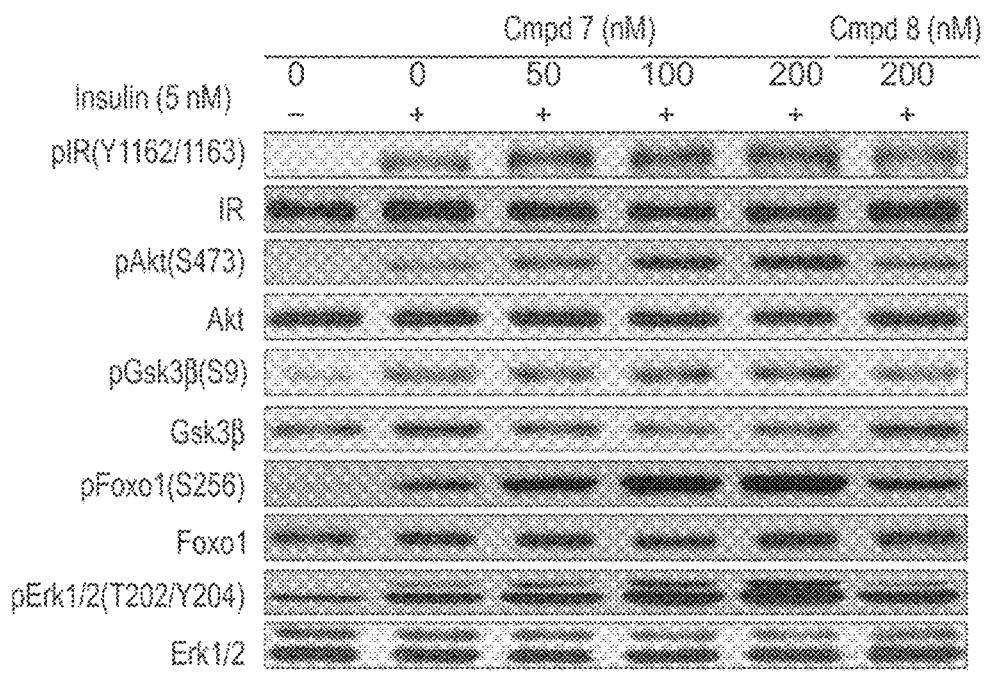
FIGS. 4A-B depict the ability of PTP-MEG2 inhibitor Compound 7 to sensitize insulin signaling in primary hepatocytes.
Figure 8:
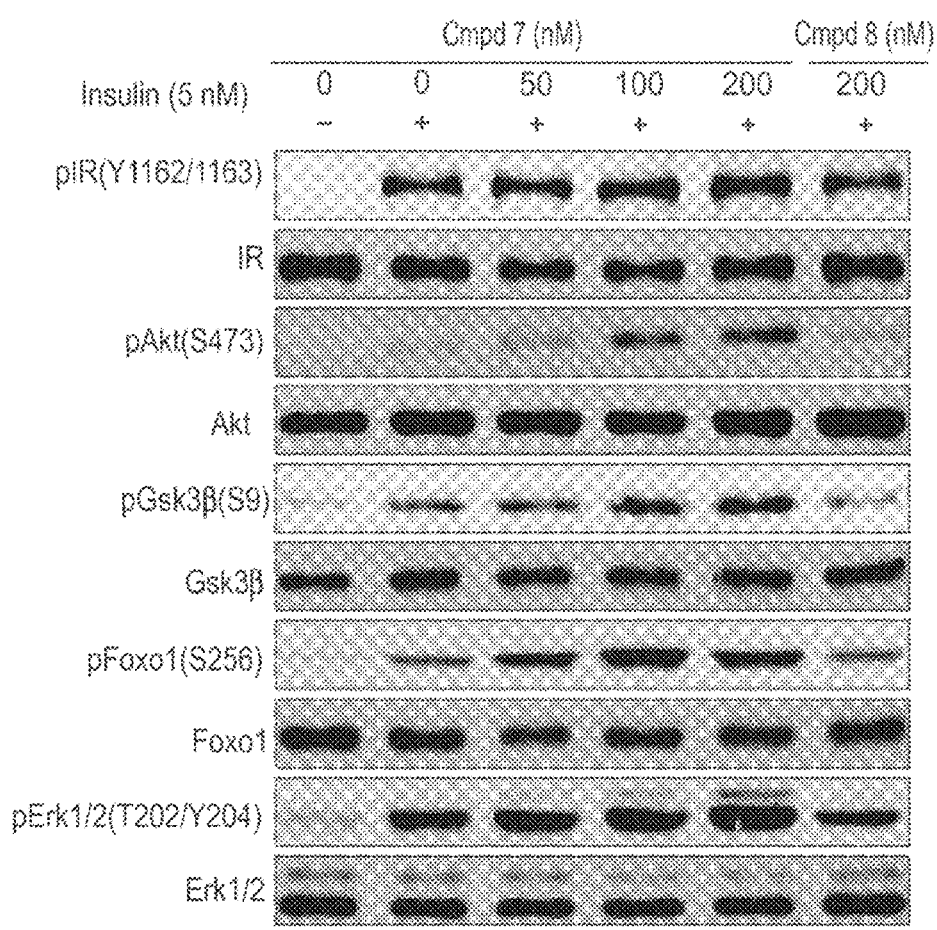
FIG. 8 shows the prolonged insulin sensitization by Compound 7. Mouse primary hepatocytes were cultured in DMEM medium plus 0.5% FBS overnight. Prior to insulin stimulation, the cells were preincubated with either vehicle DMSO, Compound 7, or Compound 8 for 1 hour. After 30 minutes of stimulation by 5 nM insulin, the hepatocytes were harvested for signaling analysis using phosphor-specific or total protein antibodies.
Figure 9:
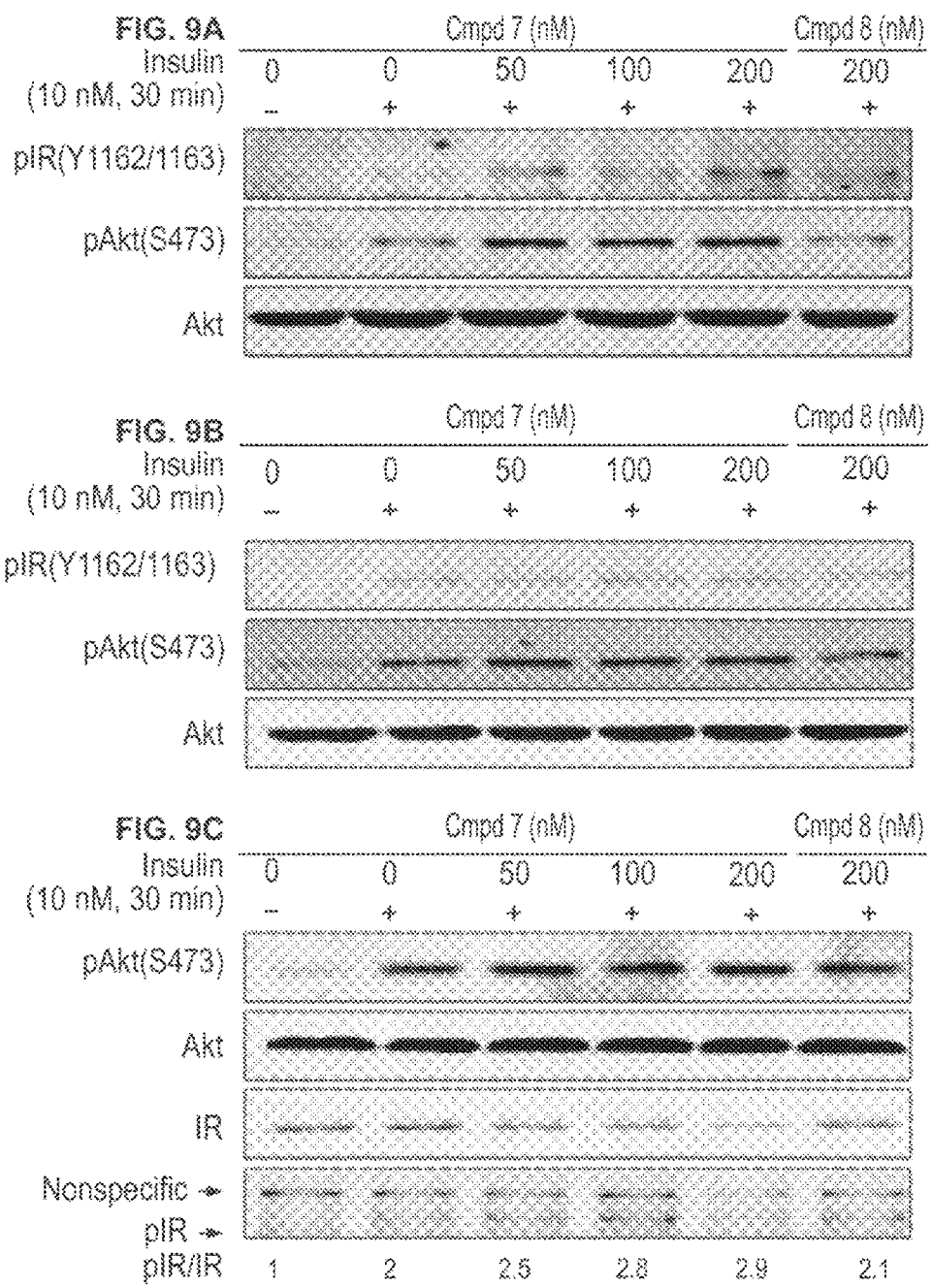
FIGS. 9A-C. show that Compound 7, but not Compound 8, augmented insulin signaling in three insulin sensitive cell lines: 3T3-L1 differentiated adipocytes, HepG2 hepatocytes, and C2C12 myotubes.

PTP-MEG2 inhibitor Compound 7 augments insulin signaling in cells. Given the excellent potency and selectivity of Compound 7 toward PTP-MEG2, we proceeded to evaluate its effect on PTP-MEG2-dependent signaling inside the cell. To assess the effects of Compound 7 on insulin signaling, we pretreated mouse primary hepatocytes with Compound 7 for 1 hour and then stimulated the cells with 5 nM insulin for 5 minutes. As shown in FIG. 4A, Compound 7 enhanced IR Tyr1162/1163 phosphorylation in a dose-dependent fashion relative to the vehicle DMSO. Remarkably, the phosphorylated form of IR was increased 50% and 100% at concentrations of 50 nM ($1.5 \times K_i$) and 100 nM of Compound 7, respectively (FIG. 4A and FIG. 8). Consistent with IR activation, the phosphorylation of several downstream molecules was also increased. Phosphorylation of Akt (Ser473) was increased by 3.1 and 4.5 fold; phosphorylation of GSK-3β (Ser9) was increased by 1.5 and 2.0 fold; and phosphorylation of Foxo1 (Ser253) was increased by 2.1 and 2.9 fold at 100 and 200 nM concentrations of Compound 7, respectively. Similarly, Erk1/2 activation was strongly enhanced by Compound 7 as well. As a control, a structurally related but inactive analog of 7 (Compound 8; see Supporting Information, below) lacking the difluoromethylenephosphonate moiety ($IC_{50} > 1$ μM) had no effect on insulin-mediated phosphorylation, even at 200 nM concentration (FIG. 4A and FIG. 8). Moreover, Compound 7, but not Compound 8, also augmented insulin signaling in three insulin sensitive cell lines: 3T3-L1 differentiated adipocytes, HepG2 hepatocytes, and C2C12 myotubes (FIG. 9A-C). The results suggest that Compound 7 has a broad insulin-sensitizing effect in various cell types and that the cellular activity displayed by Compound 7 is unlikely due to nonspecific effects.

Figure 4B:
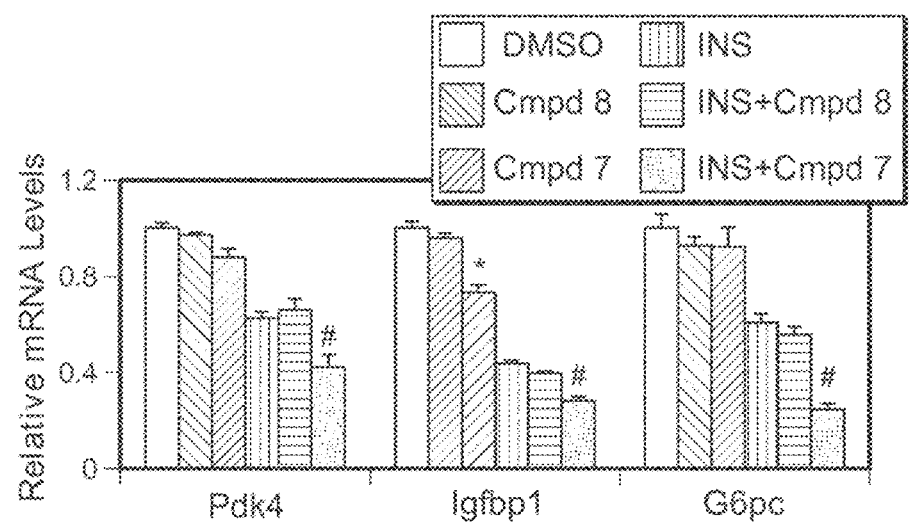
Figure 10:
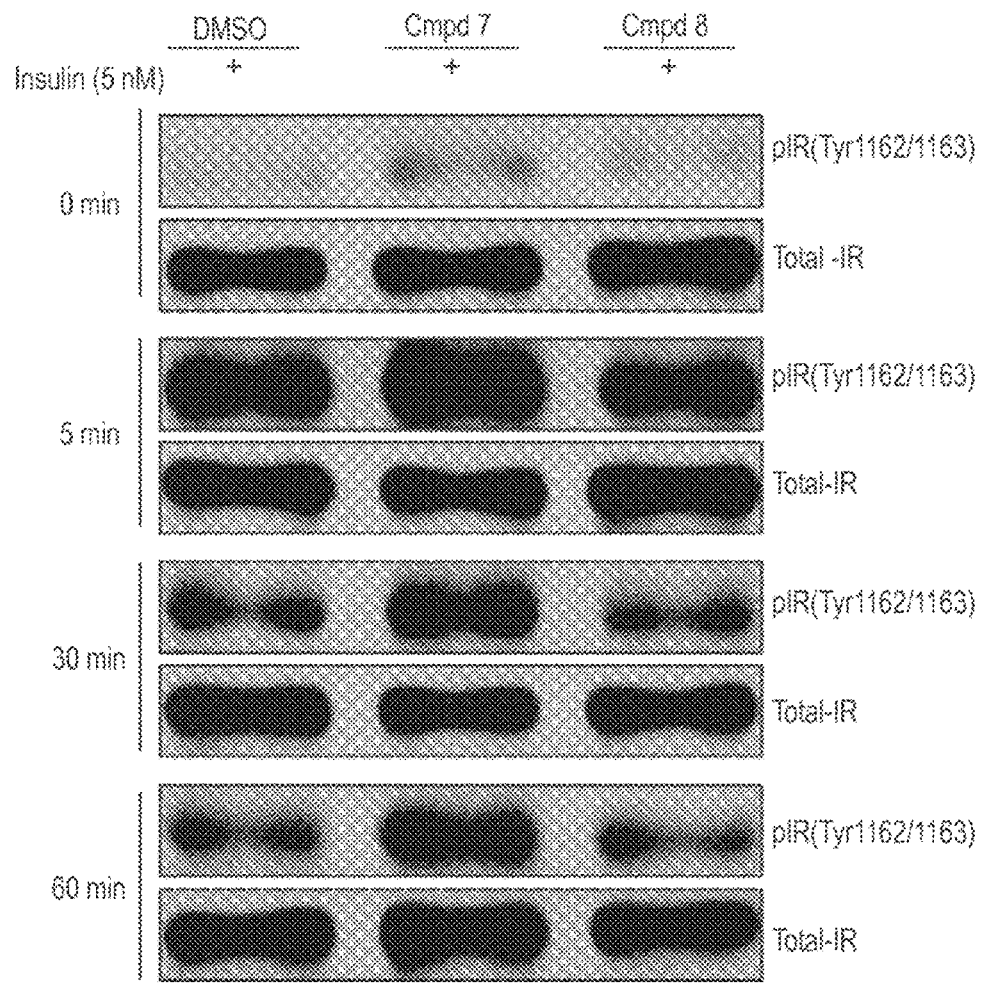
FIG. 10 depicts the time course of pIR (Tyr 1162/63) level. Primary hepatocyte cells were starved overnight. Prior to insulin stimulation, the cells were preincubated with either vehicle DMSO, Compound 7, or Compound 8 for 1 hour. Then the cells were stimulated with 5 nM Insulin for 0, 5, 30, 60 min. Cell lysates were harvested for Western Blot, using anti-pIR (Tyr 1162/63) antibodies.
Figure 11:
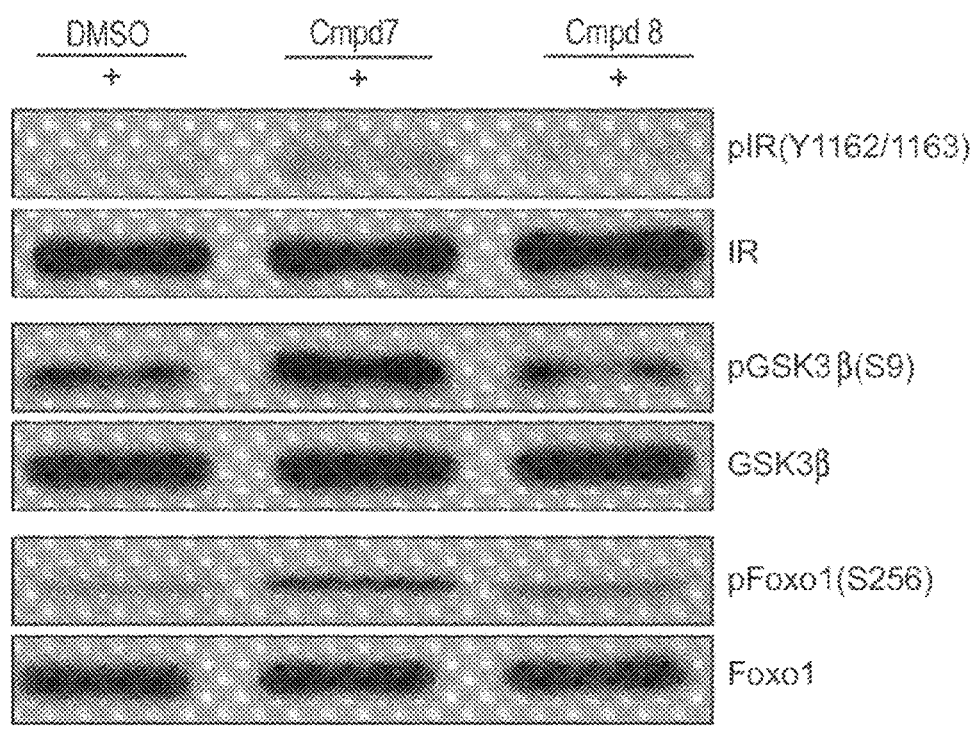
FIG. 11 shows that the insulin signaling pathway is enhanced by Compound 7 even under basal conditions. Mouse primary hepatocytes were isolated and cultured in DMEM medium with 0.5% FBS for 12 hours, and then were incubated with either vehicle DMSO, Compound 7 (100 nM), or Compound 8 (100 nM) for one hour. Phosphorylated IR, Gsk3β, and Foxo1 and the corresponding total proteins were analyzed by Western blots.

To determine the duration of insulin sensitization by Compound 7, we also performed a time-course analysis of insulin stimulated IR phosphorylation in the presence or absence of Compound 7. The data indicated that IR phosphorylation was potentiated for at least 1 hour by Compound 7 (FIG. 10). To test whether Compound 7 could increase the basal activity of IR-mediated signaling, we treated hepatocytes with vehicle alone, Compound 7, and the negative control Compound 8 for 1 hour and analyzed the signaling events. Indeed, Compound 7 could increase the basal phosphorylation of IR, GSK-3β, and Foxo1 by 2.1, 2.0 and 2.2 fold, respectively (FIG. 11). To determine the physiological consequences of PTP-MEG2 inhibition by Compound 7 in hepatocytes, we monitored several Foxo1 target genes by real-time PCR. Consistent with the elevated Foxo1 phosphorylation, Compound 7 significantly enhanced insulin's ability to suppress the transcriptional activity of Foxo1 as indicated by a synergistic reduction of Pdk4, Igfbp1, and G6pc gene expression (FIG. 4B). Collectively, the results described above indicate that Compound 7 is highly efficacious in cell-based systems. The observation that 7 inhibits PTP-MEG2 inside cells with similar potency as that toward isolated enzyme is remarkable. The intracellular bioavailability of Compound 7 is contrary to the general belief that phosphonate-based PTP inhibitors are incapable of penetrating cell membrane.

Figure 5A:
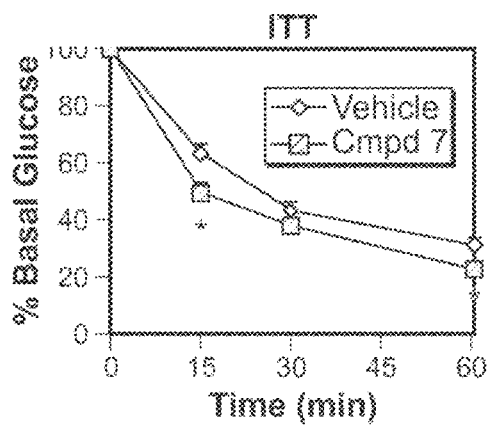
FIGS. 5A-I show the ability of Compound 7 to improve insulin resistance and glucose homeostasis in diet-induced obese mice. C57BL/6J mice were fed a high-fat diet for 10 weeks before Compound 7 or vehicle was injected intraperitoneally twice a day at a dose of 5 mg/kg body weight.
Figure 5B:
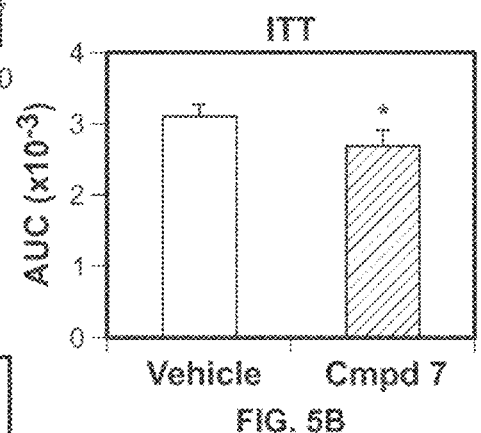
Figure 5C:
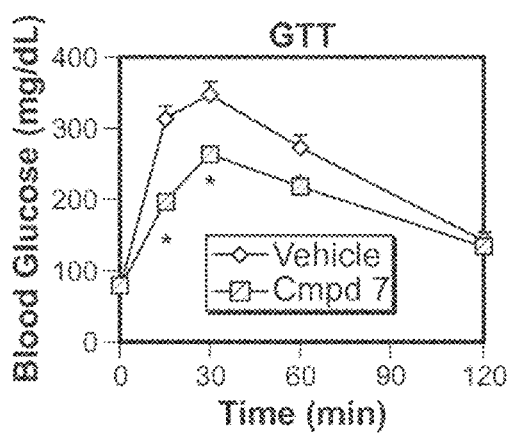
Figure 5D:
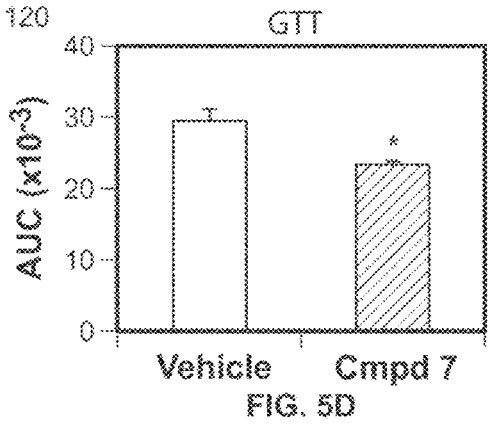
Figure 5E:
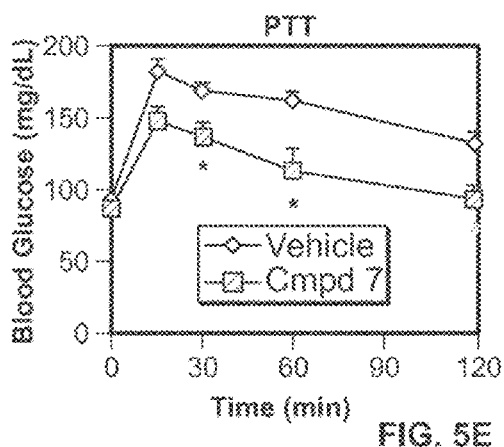
Figure 5F:
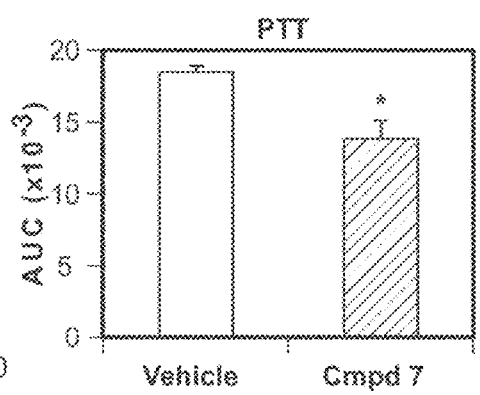

Compound 7 improves insulin sensitivity and glucose tolerance in diet-induced obese mice. Given the excellent cellular efficacy of Compound 7, we sought to evaluate the effect of PTP-MEG2 inhibition on insulin signaling in vivo. To this end, we intraperitoneally injected Compound 7 into diet-induced obese C57BL/6 mice at a dose of 5 mg/kg twice a day. Compound 7 displayed a good pharmacokinetic profile in mouse with a plasma drug exposure $C_{max}$ 4.5 μM and a half-life $t_{1/2}$=1.8 hour at a 20 mg/kg dosage. After 7 days of injections, we performed insulin tolerance tests to measure insulin sensitivity in vehicle and Compound 7 treated mice. Compound 7 significantly improved insulin sensitivity at 15 and 60 minutes after a bolus of 0.75 unit of human insulin (FIG. 5A), and the area under the curve (AUC) analysis also showed a 14% improvement in insulin tolerance (FIG. 5B). On Day 9, we performed glucose tolerance tests, and the results showed that inhibition of PTP-MEG2 by Compound 7 significantly enhanced glucose clearance at 15, 30, and 60 minutes time points and an overall 21% improvement in glucose disposal by AUC analysis (FIGS. 5C & D). Given the decreased Foxo1 activity upon PTP-MEG2 inhibition, we also examined whether Compound 7 attenuates hepatic glucose production in vivo. Indeed, the results of pyruvate tolerance tests showed significant suppression of hepatic gluconeogenesis by Compound 7 after a bolus of pyruvate injection on Day 12 (FIG. 5E), and the AUC analysis indicated a 25% better pyruvate tolerance (FIG. 5F). These results reveal remarkable improvement on systemic insulin sensitivity and glucose homeostasis upon Compound 7 treatment.

Figure 5G:
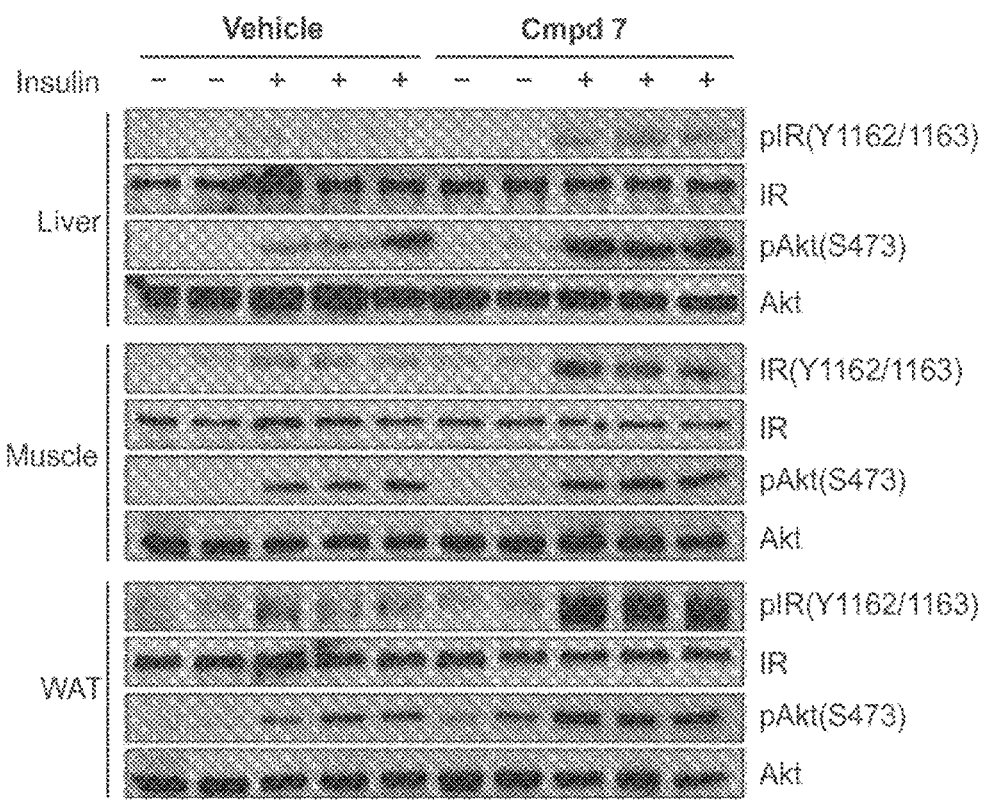
Figure 5H:
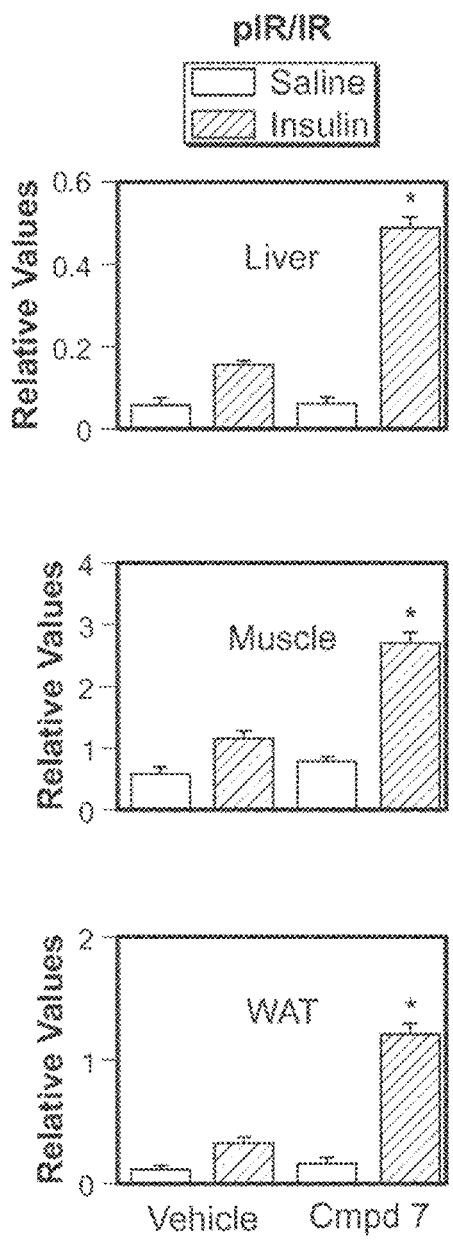
Figure 5I:
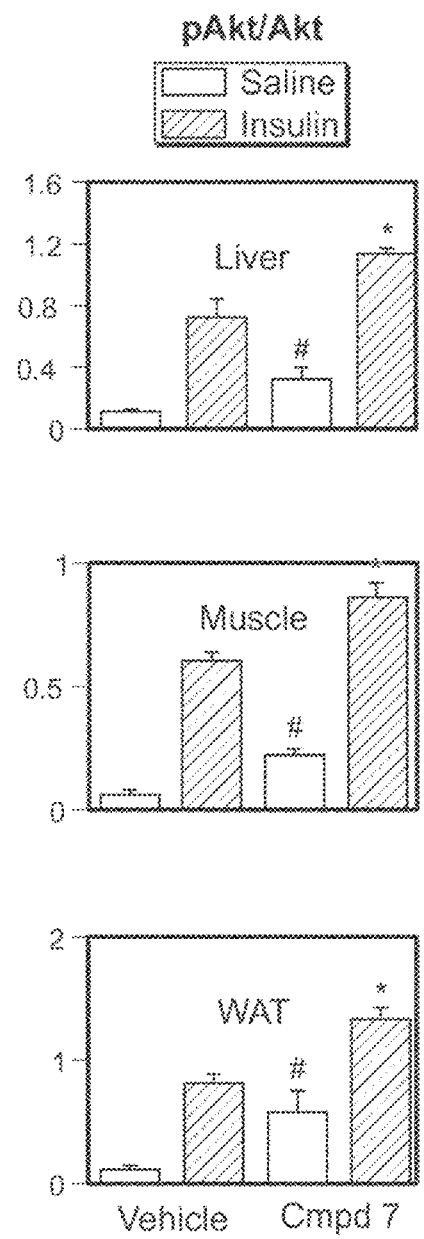

To investigate the underlying mechanisms responsible for the improved insulin sensitivity in Compound 7 treated diet-induced obese mice, we analyzed key insulin signaling events in metabolically active tissues. Phosphorylation of Tyr1162/1163 residues in IR was stimulated 2-3 fold higher in the liver, skeletal muscle, and white adipose tissue in Compound 7 treated mice than that in control mice (FIGS. 5G & H). The downstream Akt kinase was also more active, indicated by an increase of 40-60% phosphorylation of Ser473 (FIGS. 5G and I). These biochemical data are consistent with the animal phenotype that Compound 7 can effectively improve insulin sensitivity in diet-induced obese mice. Our finding that chemical inhibition of PTP-MEG2 augments insulin signaling, insulin sensitivity and glucose homeostasis in insulin resistant mice is consistent with the observation that silencing of PTP-MEG2 in the livers of db/db mice results in a reversal of insulin resistance and hyperglycemia (Cho, et al., *Cell Metab.* 2006, 3, 367-378). Moreover, our in vivo data also serve as proof-of-concept and support the notion that specific inhibitors of PTP-MEG2 may be effective anti-diabetes agents.

Supporting Information

Materials. Dimethylformamide (DMF), isopropanol, dichloromethane (DCM), N-methyl morpholine (NMM), and acetic acid (AcOH), disposable syringes (with a frit) were from Fisher Scientific. Diethyl ether, piperidine, trifluoroacetic acid (TFA), triisopropylsilane (TIS), tetrakis(triphenylphosphine)-palladium(0), 3-iodobenzoic acid (mIBA), and 3-bromo-4-methylbenzoic acid (BMBA), homovanillic acid (HMVA) were from Aldrich. The Rink amide resin, O-benzotriazole-N,N,N',N'-tetramethyluroniumhexafluorophosphate (HBTU), N-hydroxybenzotriazole (HOBt), Fmoc-Phe-OH, Fmoc-Lys(Alloc)-OH, Fmoc-Orn(Boc)-OH, Fmoc-β-Ala-OH, Fmoc-Orn(Alloc)-OH, Fmoc-Lys(Mtt)-OH, Fmoc-Phe(4-I)-OH, Fmoc-Dpr(Boc)-OH were from Advanced ChemTech. 5-Carboxyfluorescein (5-FAM) was from Anaspec. Fmoc-F$_2$Pmp-OH was prepared following the literature procedures (Gordeev, M. F. et al., Tetrahedron Lett.

1994, 35, 7585-7588; Qui, W. et al., Tetrahedron Lett. 1996, 37, 2745-2748). Compound C1 (FIG. 6) was prepared as previously reported (Zhang, *J. Am. Chem. Soc.* 2009, 131, 13072-13079).

Instrumentation. HPLC purification was carried out on a Waters Breeze HPLC system equipped with a Waters Atlantis dC18 column (10 µm, 19 mm×100 mm) $^1$H and $^{13}$C NMR spectra were recorded on a Bruker Avance II 500-MHz NMR spectrometer. Analytical HPLC analysis was carried out on a Waters Breeze HPLC system equipped with an Agilent Eclipse XDB-C18 column (5 µm, 4.6 mm×150 mm).

General Procedure A for Rink Amide Resin Activation. Rink amide resin (Advanced ChemTech) was mixed with DCM (1 mL per 100 mg resin) and then shaken for 30 minutes. After activation, resin was washed three times with DMF (1 mL per 100 mg resin).

General Procedure B for the Removal of the Fmoc Group from the Rink Amide Resin. Rink amide resin was mixed with 20% piperidine in DMF (1 mL per 100 mg resin) and shaken for 30 minutes, and then washed with DMF (1 mL per 100 mg resin, 3 times), isopropanol (1 mL per 100 mg resin, 3 times), and DCM (1 mL per 100 mg resin, 3 times) sequentially. The removal of the Fmoc group was confirmed by the ninhydrin test.

General Procedure C for the Removal the Alloc Group from the Rink Amide Resin. The resin (200 mg) was washed with DCM (2 mL, 5 times) and shaken under $N_2$ overnight with a solution of tetrakis(triphenylphosphine)palladium(0) (10 mg), AcOH (0.5 mL), and NMM (0.2 mL) in DCM (10 mL). The resin was then washed with DMF (2 mL, 3 times), isopropanol (2 mL, 3 times), and DCM (2 mL, 3 times). The removal of the Alloc group was confirmed by the ninhydrin test.

General Procedure D for the Removal the Mtt Group from the Rink Amide Resin. The resin was washed with DCM (1 mL per 100 mg resin, 10 times). The resin was shaken with TFA (1% in DCM, 1 mL per 100 mg resin) for 1 minute (repeat 10 times). The resin was then washed with DCM (1 mL per 100 mg resin, 3 times), DMF (1 mL per 100 mg resin, 3 times), isopropanol (1 mL per 100 mg resin, 3 times), and DCM (1 mL per 100 mg resin, 3 times). The removal of the Mtt group was confirmed by the ninhydrin test.

General Procedure E for the Coupling of Carboxylic Acids to the Rink Amide Resin. Carboxylic acids (5 equiv, 0.5 M in DMF) were first mixed with HBTU (5 equiv, 0.5 M in DMF), HOBt (5 equiv, 0.5 M in DMF), and NMM (15 equiv, 1.5 M in DMF). The mixed solution was then added to the resin and shaken for 2 hours. The resin was then washed with DMF (1 mL per 100 mg resin, 3 times), isopropanol (1 mL per 100 mg resin, 3 times), and DCM (1 mL per 100 mg resin, 3 times). The completion of the coupling reaction was confirmed by the ninhydrin test.

General Procedure F for Peptide Cleavage from the Rink Amide Resin. The resin was washed with DCM (1 mL per 100 mg resin, 5 times) and subsequently shaken with a solution of 95% TFA, 2.5% TIS, and 2.5% $H_2O$ (1 mL per 100 mg resin) for 2 hours. The resin was removed by filtration, and the TFA was evaporated under vacuum. The crude peptide was obtained after trituration with diethyl ether (5 mL per 100 mg resin, 2 times).

Figure 12:
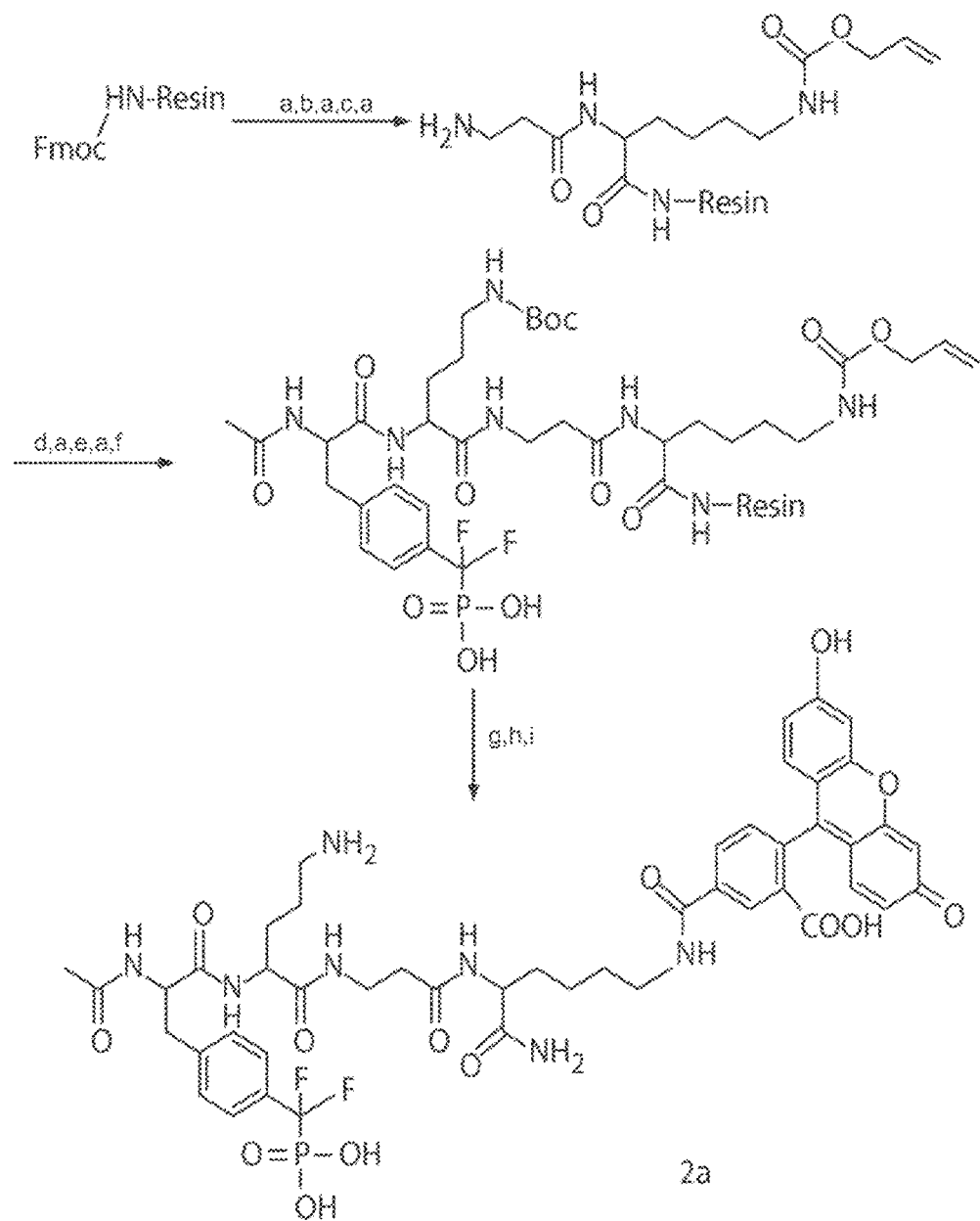
FIG. 12 depicts the synthesis of Compound 2a: (a) 30% piperidine/DMF; (b) Fmoc-Lys(Alloc)-OH/HBTU/HOBt/NMM; (c) Fmoc-β-Ala-OH/HBTU/HOBt/NMM; (d) Fmoc-Orn(Boc)-OH/HBTU/HOBt/NMM; (e) Fmoc-F2Pmp-OH/HBTU/HOBt/NMM; (f) AcOH/HBTU/HOBt/NMM; (g) Pd(0)/NMM/AcOH; (h) 5-Carboxy-fluorescein/HBTU/HOBt/NMM; (i) 95% TFA/H20/TIS.

Synthesis of Compound 2a. Compound 2a was synthesized using standard Fmoc chemistry on the Rink amide resin in a disposable syringe with a frit (FIG. 12). Rink amide resin (200 mg, 0.7 mmol/g loading, 0.14 mmol) was first activated with DCM (2 mL, general procedure A). Fmoc group was removed by 20% piperidine (general procedure B). The resin was the coupled with Fmoc-Lys(Alloc)-OH (general procedure E). After the deprotection of Fmoc group (general procedure B), the resin was couple with Fmoc-β-Ala-OH (general procedure E). The resin was treated with piperidine (general procedure B) and coupled with Fmoc-Orn(Boc)-OH (general procedure E). The Fmoc group was removed (general procedure B), and the resin was coupled with Fmoc-$F_2$Pmp-OH (general procedure E). The Fmoc group was removed (general procedure B), and resin was coupled with AcOH (general procedure E). Then, the resin was tread with Pd(0) for the removal of Alloc group (general procedure C) and coupled with 5-FAM (general procedure E). Compound 2a was cleaved from beads (general procedure F). Crude peptide was purified by HPLC to afford 2a (12.1 mg, 9% yield). MS (ESI): calculated for [M] 1007, found [M+H]$^+$ 1008.

Synthesis of the Library 2b. The library was prepared on a Freedom EVO workstation (Tecan) with a 96 channel MCA tip block using disposable tips (Rainin). The detailed procedure is as follows: the 576 different carboxylic acids (40 mM, 10 µL) in DMF were placed in six 96-well microplates. HBTU (35 mM in DMF, 10 µL), HOBt (50 mM in DMF, 10 µL), and NMM (200 mM in DMF, 10 µL) were sequentially added to each well of the six plates and mixed for 5 min for the activation of carboxylic acids. The precursor 2a (2 mM in DMF, 10 µL) was then added to each well. The reaction was quenched with cylcohexylamine (87 mM in DMF, 10 µL) after 1 hour. Finally, 190 µL of DMSO were added to each well to create the ready-for-screening format. The library was stored in a −20° C. freezer before screening.

Figure 13:
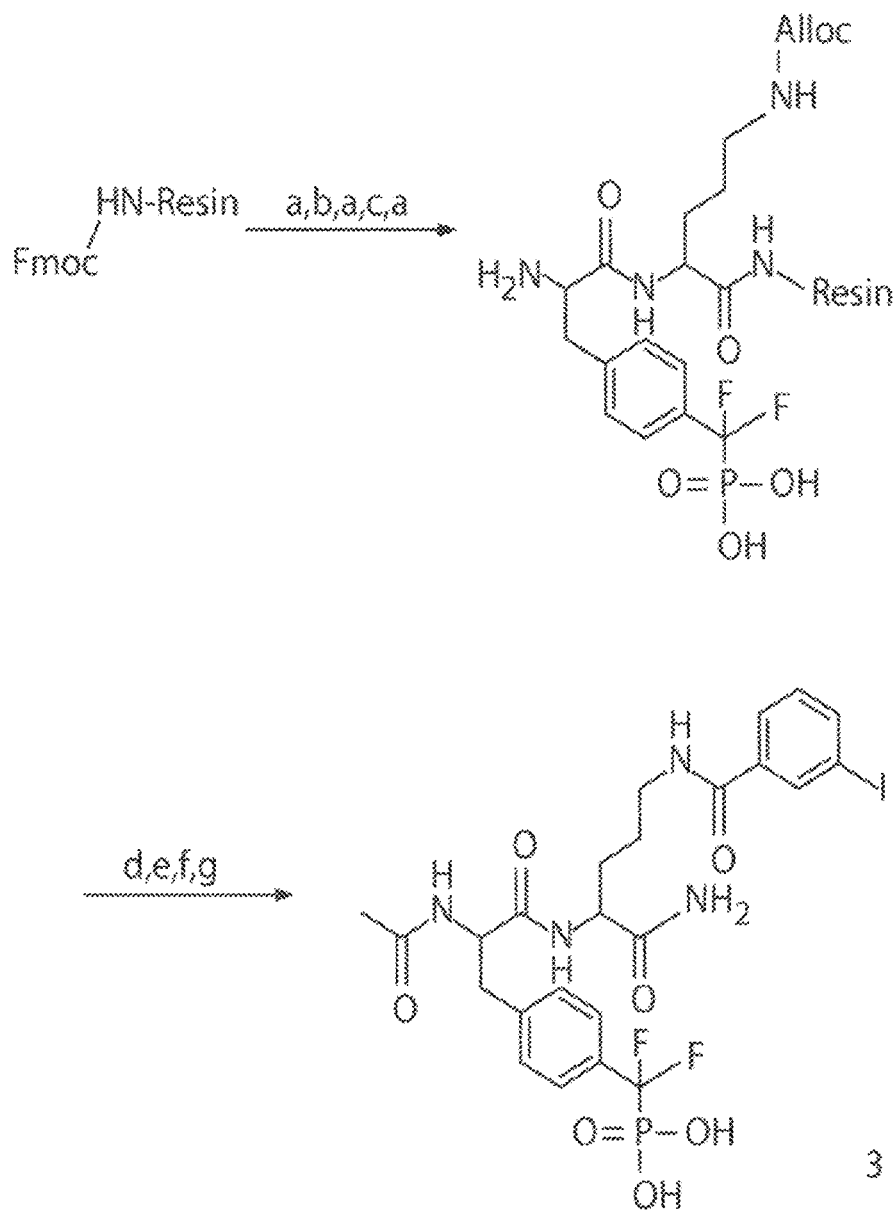
FIG. 13 depicts the synthesis of Compound 3: (a) 30% piperidine/DMF; (b) Fmoc-Orn(Alloc)-OH/HBTU/HOBt/NMM; (c) Fmoc-F₂Pmp-OH/HBTU/HOBt/NMM; (d) AcOH/HBTU/HOBt/NMM; (e) Pd(0)/NMM/AcOH; (f) 3-iodobenzoic acid/HBTU/HOBt/NMM; (g) 95% TFA/H20/TIS.

Synthesis of Compound 3. Compound 3 was synthesized using standard Fmoc chemistry on the Rink amide resin (FIG. 13). The resin (200 mg, 0.7 mmol/g loading, 0.14 mmol) was first activated by DCM (General procedure A). The Fmoc group on the resin was removed by piperidine in DMF (General procedure B). The resin was then coupled with Fmoc-Orn(Alloc)-OH (general procedure E). The Fmoc group was removed (General procedure B) and Fmoc-$F_2$Pmp-OH was attached to resin (General procedure E). The Fmoc group was again removed (general procedure B) and the amine group on the $F_2$Pmp residue was capped by AcOH (general procedure E). The resin was treated with Pd(0) for the deprotection of Alloc group (general procedure C). 3-Iodobenzoic acid (mIBA) was attached to resin (general procedure E). Compound 3 was cleaved from beads (General procedure F). Crude peptide was purified by HPLC to afford 3 (15.1 mg, 16% yield). The assignment of proton NMR utilized additional information from COSY. $^1$H NMR (500 MHz, CD3OD): δ=8.17 (s, 1 H, mIBA-ArH), 7.87 (d, J=7.9 Hz, 1 H, mIBA-ArH) 7.79 (d, J=7.9 Hz, 1 H, mIBA-ArH) 7.50 (d, J=7.9 Hz, 2 H, $F_2$Pmp-ArH), 7.33 (d, J=7.9 Hz, 2 H, $F_2$Pmp-ArH), 7.24-7.20 (m, 1 H, mIBA-ArH), 4.59-4.53 (m, 1 H, $F_2$Pmp-$C_\alpha$H), 4.37-4.32 (m, 1 H, Orn-$C_\alpha$H), 3.40-3.32 (m, 2 H, Orn-C$\delta$H$_2$), 3.07-3.02 (m, 2 H, $F_2$Pmp-$C_\beta$H$_2$), 1.94 (s, 3 H, —COCH$_3$). 1.80-1.71 (m, 1 H, Orn-$C_\beta$HH'), 1.68-1.54 (m, 3 H, Orn-$C_\beta$HH', Orn-$C_\gamma$H$_2$). $^{13}$C NMR (125 MHz, CD3OD): δ=173.32, 173.16, 141.53, 140.72, 137.78, 137.35, 131.36, 130.32, 127.59, 94.68, 56.43, 40.36, 38.63, 30.40, 26.72, 22.37. MS (ESI): calculated for [M], 680, found [M+H]$^+$ 681. HPLC purity analysis: >95% (UV, λ=254 nm).

Figure 14:
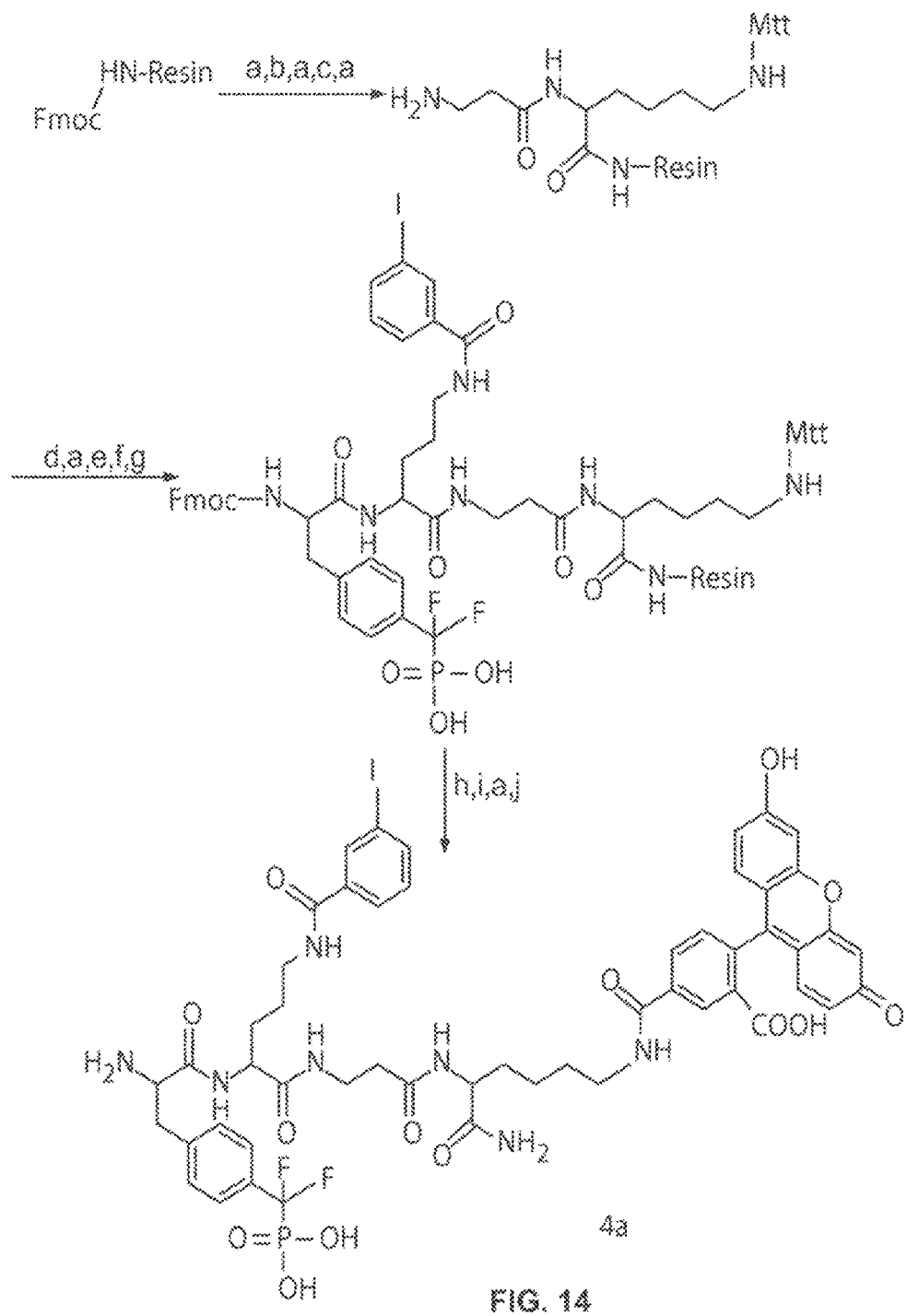
FIG. 14 depicts the synthesis of Compound 4a: (a) 30% piperidine/DMF; (b) Fmoc-Lys(Mtt)-OH/HBTU/HOBt/NMM; (c) Fmoc-β-Ala-OH/HBTU/HOBt/NMM; (d) Fmoc-Orn(Alloc)-OH/HBTU/HOBt/NMM; (e) Fmoc-F₂Pmp-OH/HBTU/HOBt/NMM; (f) Pd(0)/NMM/AcOH; (g) 3-iodobenzoic acid/HBTU/HOBt/NMM; (h) 1% TFA/TIS/DCM; (i) 5-Carboxyfluorescein/HBTU/HOBt/NMM; (j) 95% TFA/H20/TIS.

Synthesis of Compound 4a. Compound 4a was synthesized using standard Fmoc chemistry on the Rink amide resin in a disposable syringe with a frit (FIG. 14). Rink amide resin (200 mg, 0.7 mmol/g loading, 0.14 mmol) was first activated with DCM (2 mL, general procedure A). Fmoc group was removed by piperidine (20% solution in DMF, 2 mL, general procedure B). The resin was the coupled with Fmoc-Lys(Mtt)-OH (general procedure E). After the deprotection of Fmoc group (general procedure B), the resin was couple with Fmoc-β-Ala-OH (general procedure E). The resin was treated with piperidine (general procedure B) and coupled with Fmoc-Orn(Alloc)-OH (general procedure E). The Fmoc group was removed (general procedure B), and the resin was coupled with Fmoc-F$_2$Pmp-OH (general procedure E). The Alloc group was removed (general procedure C), and resin was coupled with mIBA (general procedure E). The resin was treated with 1% TFA in DCM for the removal of Mtt group (general procedure D) and coupled with 5-FAM (general procedure E). The resin was treated with piperidine to remove Fmoc group. Compound 4a was cleaved from beads (general procedure F). Crude peptide was purified by HPLC to afford 4a (10.4 mg, 6% yield). MS (ESI): calculated for [M] 1195, found [M+H]$^+$ 1196.

Synthesis of the Library 4b. The library was prepared in the same procedure as the library 2b, except that compound 4a (2 mM in DMF) was used as the library precursor.

Figure 15:
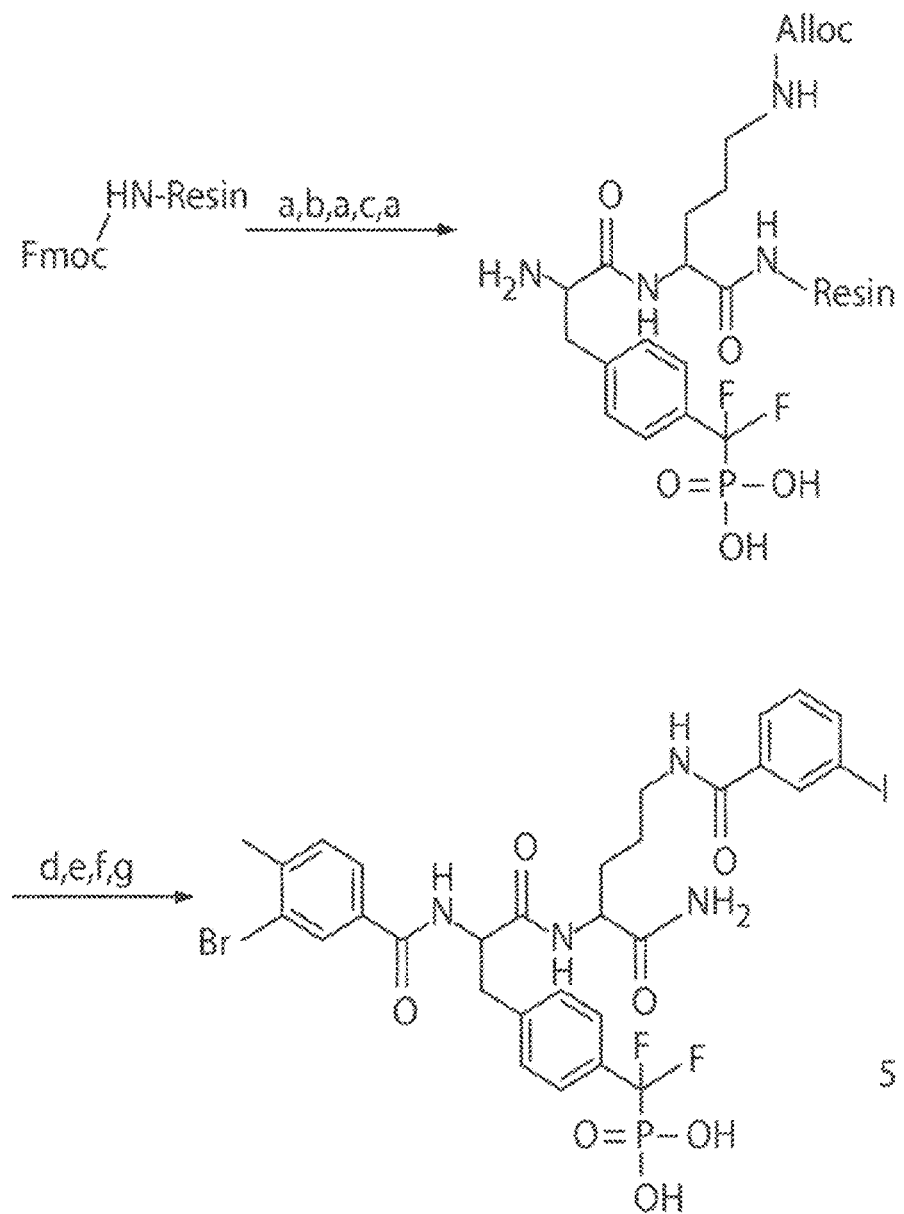
FIG. 15 depicts the synthesis of Compound 5: (a) 30% piperidine/DMF; (b) Fmoc-Orn(Alloc)-OH/HBTU/HOBt/NMM; (c) Fmoc-F2Pmp-OH/HBTU/HOBt/NMM; (d) 3-bromo-4-methylbenzoic acid/HBTU/HOBt/NMM; (e) Pd(0)/NMM/AcOH; (f) 3-iodobenzoic acid/HBTU/HOBt/NMM; (g) 95% TFA/H₂O/TIS.

Synthesis of Compound 5. Compound 5 was synthesized using standard Fmoc chemistry on the Rink amide resin (FIG. 15). The resin (200 mg, 0.7 mmol/g loading, 0.14 mmole) was first activated by DCM (General procedure A). The Fmoc group on the resin was removed by piperidine in DMF (General procedure B). The resin was then coupled with Fmoc-Orn(Alloc)-OH (general procedure E). The Fmoc group was removed (General procedure B) and Fmoc-F$_2$Pmp-OH was attached to resin (General procedure E). The Fmoc group was again removed (general procedure B) and the resin was couple with BMBA (general procedure E). The resin was treated with Pd(0) for the deprotection of Alloc group (general procedure C). 3-Iodobenzoic acid (mIBA) was attached to resin (general procedure E). Compound 5 was cleaved from beads (General procedure F). Crude peptide was purified by HPLC to afford 5 (13.6 mg, 12% yield). The assignment of proton NMR utilized additional information from COSY. $^1$H NMR (500 MHz, CD$_3$OD): δ=8.14 (s, 1 H, mIBA-ArH), 7.98 (s, 1 H, BMBA-ArH), 7.84 (d, J=7.9 Hz, 1 H, mIBA-ArH), 7.76 (d, J=7.9 Hz, 1 H, mIBA-ArH) 7.64 (d, J=8.2 Hz, 1 H, BMBA-ArH), 7.51 (d, J=7.9 Hz, 2 H, F$_2$Pmp-ArH), 7.38 (d, J=7.9 Hz, 2 H, F2 Pmp-ArH) 7.31 (d, J=8.2 Hz, 1 H, BMBA-ArH), 7.21-7.17 (m, 1 H, mIBA-ArH), 4.79-4.73 (m, 1 H, F$_2$Pmp-C$_α$H), 4.41-4.34 (m, 1 H, Orn-C$_α$H), 3.40-3.32 (m, 2 H, Orn-C$_δ$H$_2$), 3.20-3.15 (m, 2 H, F$_2$Pmp-C$_β$H$_2$), 2.41 (s, 3 H, BMBA-Ar—CH$_3$). 1.82-1.75 (m, 1 H, Orn-C$_β$HH'), 1.75-1.61 (m, 3H, Orn-C$_β$HH', Orn-C$_γ$H$_2$). $^{13}$C NMR (125 MHz, CD$_3$OD): δ=173.28, 168.65, 143.18, 141.53, 137.75, 137.39, 134.53, 132.51, 131.98, 131.36, 130.35, 127.64, 127.59, 125.70, 94.75, 57.05, 40.40, 38.44, 30.44, 26.76, 23.07. MS (ESI): calculated for [M], 834, found [M+H]+ 835. HPLC purity analysis: >95% (UV, λ=254 nm).

Figure 16:
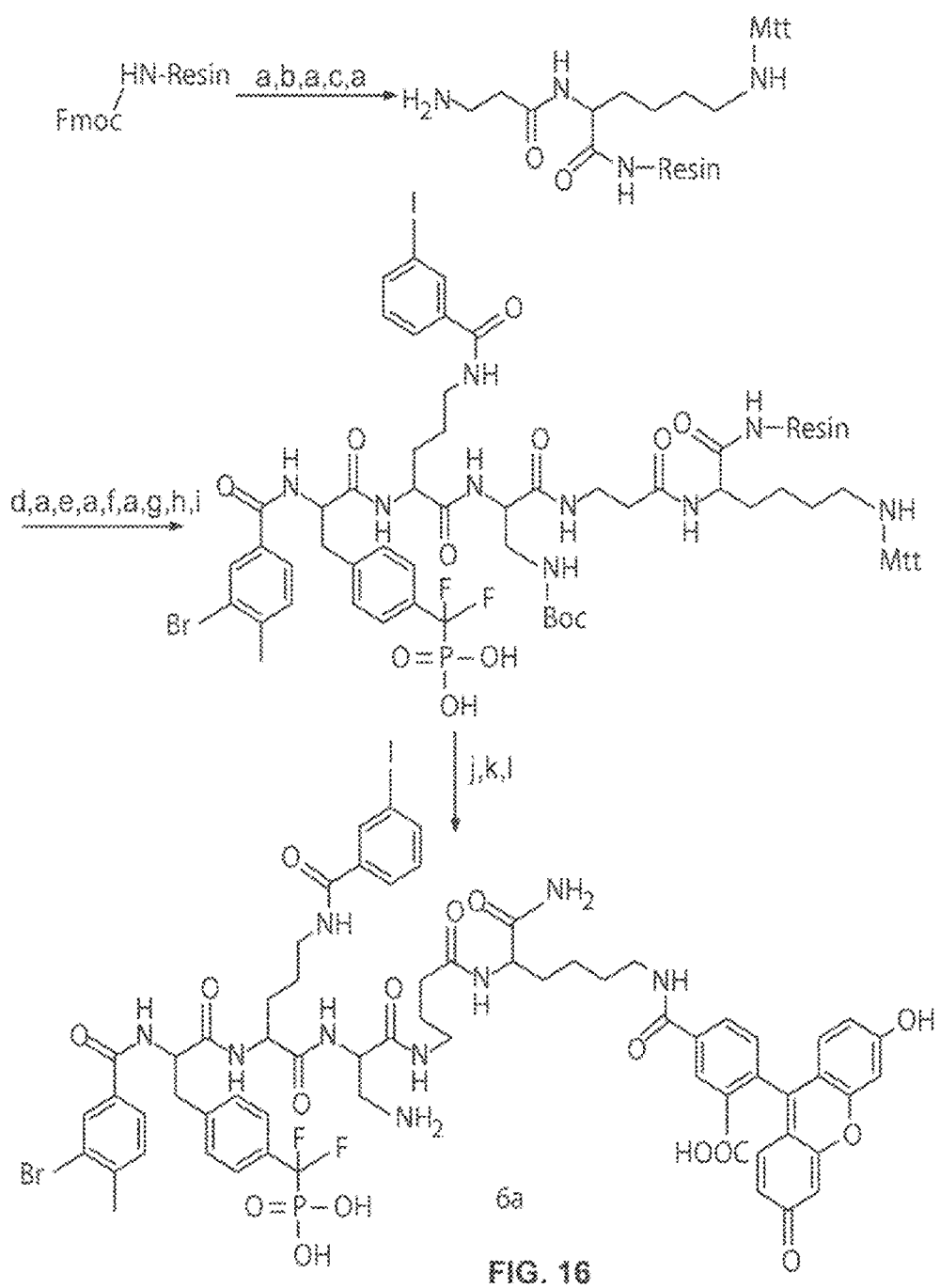
FIG. 16 depicts the synthesis of Compound 6a: (a) 30% piperidine/DMF; (b) Fmoc-Lys(Mtt)-OH/HBTU/HOBt/NMM; (c) Fmoc-β-Ala-OH/HBTU/HOBt/NMM; (d) Fmoc-Dpr(Boc)-OH/HBTU/HOBt/NMM; (e) Fmoc-Orn(Alloc)-OH/HBTU/HOBt/NMM; (f) Fmoc-F2Pmp-OH/HBTU/HOBt/NMM; (g) 3-bromo-4-methylbenzoic acid/HBTU/HOBt/NMM; (h) Pd(0)/NMM/AcOH; (i) 3-iodobenzoic acid/HBTU/HOBt/NMM; (j) 1% TFA/TIS/DCM; (k) 5-Carboxyfluorescein/HBTU/HOBt/NMM; (l) 95% TFA/H₂O/TIS.

Synthesis of Compound 6a. Compound 6a was synthesized using standard Fmoc chemistry on the Rink amide resin in a disposable syringe with a frit (FIG. 16). Rink amide resin (200 mg, 0.7 mmol/g loading, 0.14 mmol) was first activated with DCM (2 mL, general procedure A). Fmoc group was removed by piperidine (20% solution in DMF, 2 mL, general procedure B). The resin was the coupled with Fmoc-Lys (Mtt)-OH (general procedure E). After the deprotection of Fmoc group (general procedure B), the resin was couple with Fmoc-β-Ala-OH (general procedure E). The resin was treated with piperidine (general procedure B) and coupled with Fmoc-Dpr(Boc)-OH (general procedure E). The resin was treated with piperidine (general procedure B) and coupled with Fmoc-Orn(Alloc)-OH (general procedure E). The Fmoc group was removed (general procedure B), and the resin was coupled with Fmoc-F$_2$Pmp-OH (general procedure E). The resin was treated with piperidine (general procedure B) and coupled with BMBA (general procedure E). The Alloc group was removed (general procedure C), and resin was coupled with mIBA (general procedure E). The resin was treated with 1% TFA in DCM for the removal of Mtt group (general procedure D) and coupled with 5-FAM (general procedure E). Compound 6a was cleaved from beads (general procedure F). Crude peptide was purified by HPLC to afford Compound 6a (8.6 mg, 4% yield). MS (ESI): calculated for [M] 1477, found [M+H]$^+$ 1478.

Synthesis of Library 6b. The library was prepared in the same procedure as the library 2b, except that compound 6a (2 mM in DMF) was used as the library precursor.

Figure 17:
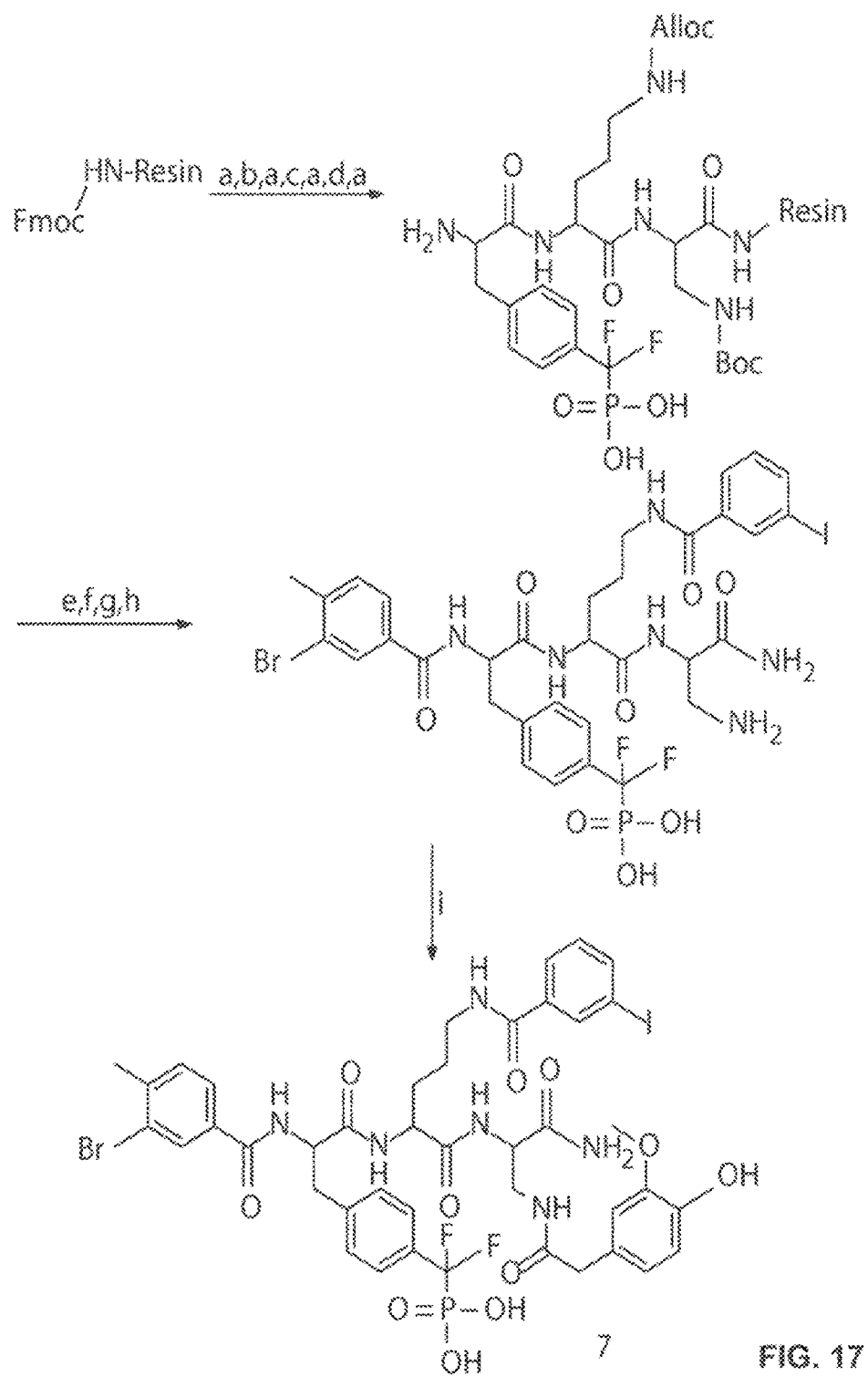
FIG. 17 depicts the synthesis of Compound 7: (a) 30% piperidine/DMF; (b) Fmoc-Dpr(Boc)-OH/HBTU/HOBt/NMM; (c) Fmoc-Orn(Alloc)-OH/HBTU/HOBt/NMM; (d) Fmoc-F2Pmp-OH/HBTU/HOBt/NMM; (e) 3-bromo-4-methylbenzoic acid/HBTU/HOBt/NMM; (f) Pd(0)/NMM/AcOH; (g) 3-iodobenzoic acid/HBTU/HOBt/NMM; (h) 95% TFA/H₂O/TIS; (i) homovanillic acid/HBTU/HOBt/NMM.

Synthesis of Compound 7. Compound 7 was synthesized using standard Fmoc chemistry on the Rink amide resin (FIG. 17). The resin (200 mg, 0.7 mmol/g loading) was first activated by DCM (General procedure A). The Fmoc group on the resin was removed by piperidine in DMF (General procedure B). The resin was then coupled with Fmoc-Dpr(Boc)-OH. The Fmoc group on the resin was removed by piperidine in DMF (General procedure B). The resin was then coupled with Fmoc-Orn(Alloc)-OH. The Fmoc group was removed (General procedure B) and Fmoc-F2Pmp-OH was attached to resin (General procedure E). The Fmoc group was again removed (general procedure B) and the amine group on the F$_2$Pmp residue was coupled with BMBA (general procedure E). The resin was treated with Pd(0) for the deprotection of Alloc group (general procedure C). 3-Iodobenzoic acid (mIBA) was attached to resin (general procedure E). The resin was treated with TFA (general procedure F) to give the crude peptide intermediate, which was treated with a mixture of HVA (0.5 M in DMF, 100 µL), HBTU (0.5 M in DMF, 100 µL), HOBt (0.5 M in DMF, 100 µL) and NMM (1.5 M in DMF, 100 µL) to give the crude product 7. The crude product was purified by HPLC to afford compound 7 (21.5 mg, 14% yield). The assignment of proton NMR utilized additional information from COSY. $^1$H NMR (500 MHz, CD$_3$OD): δ=8.16 (s, 1 H, mIBA-ArH), 7.92 (s, 1 H, BMBA-ArH), 7.86 (d, J=7.9 Hz, 1 H, mIBA-ArH), 7.78 (d, J=7.9 Hz, 1 H, mIBA-ArH) 7.64 (d, J=8.2 Hz, 1 H, BMBA-ArH), 7.58-7.52 (m, 3 H, BMBA-ArH, F$_2$Pmp-ArH), 7.39 (d, J=7.9 Hz, 2 H, F$_2$Pmp-ArH) 7.27 (d, J=8.2 Hz, 1 H, BMBA-ArH), 7.21-7.16 (m, 1 H, mIBA-ArH), 6.81-6.78 (m, 1 H, HVA-ArH), 6.71-6.63 (m, 2 H, HVA-ArH), 4.83-4.80 (m, 1 H, F$_2$Pmp-C$_α$H), 4.48-4.42 (m, 1 H, Dpr-C$_α$H), 4.30-4.24 (m, 1 H, Orn-C$_α$H), 3.77 (s, 3 H, HVA-OCH$_3$), 3.63-3.58 (m, 1 H, Dpr-C$_β$H'), 3.51-3.45 (m, 1 H, Dpr-C$_β$HH'), 3.41-3.33 (m, 5 H, Orn-C$_δ$H$_2$, F$_2$Pmp-C$_β$HH', HVA-CH$_2$—CO—), 3.16-3.09 (m, 1 H, F$_2$Pmp-C$_β$HH'), 2.39 (s, 3 H, BMBA-Ar—CH$_3$). 1.92-1.85 (m, 1 H, Orn-C$_β$HH'), 1.75-1.62 (m, 3 H, Orn-C$_β$HH', Orn-C$_γ$H$_2$). $_{13}$C NMR (125 MHz, CD3OD): δ=175.72, 174.20, 174.15, 168.85, 168.48, 148.97, 146.60, 143.20, 141.53, 141.41, 137.67, 137.41, 134.42, 132.45, 131.95, 131.35, 130.25, 127.83, 127.63, 127.60 127.53, 125.65, 122.83, 116.30, 113.84, 101.39, 94.73, 56.73, 56.43, 55.33, 43.37, 42.17, 40.39, 37.76, 29.54, 26.96, 23.03. MS (ESI): calculated for [M], 1084, found [M+H]$^+$ 1085. HPLC purity analysis: >95% (UV, λ=254 nm).

Figure 18:
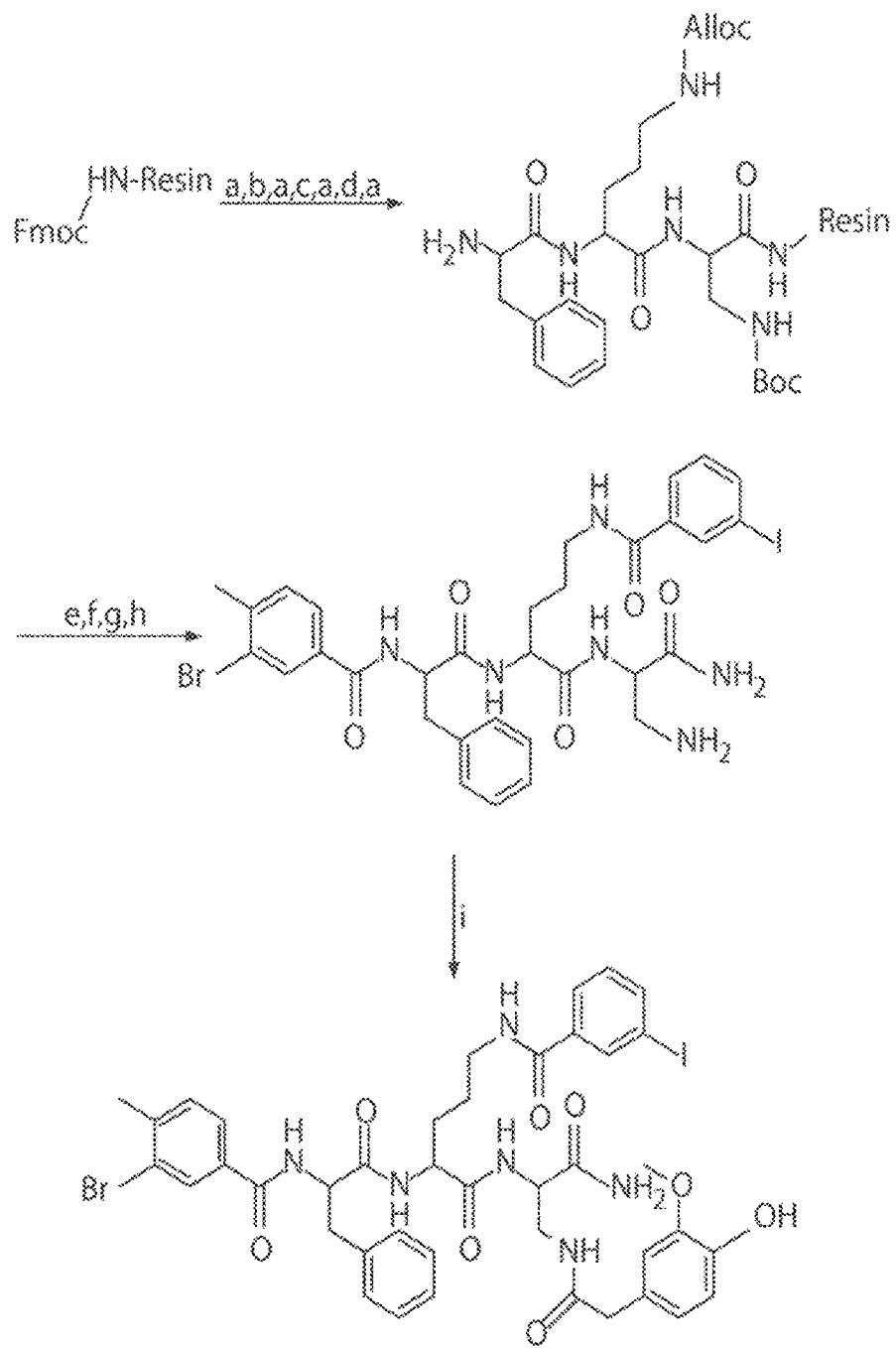
FIG. 18 depicts the synthesis of Compound 8: (a) 30% piperidine/DMF; (b) Fmoc-Dpr(Boc)-OH/HBTU/HOBt/NMM; (c) Fmoc-Orn(Alloc)-OH/HBTU/HOBt/NMM; (d) Fmoc-Phe-OH/HBTU/HOBt/NMM; (e) 3-bromo-4-methylbenzoic acid/HBTU/HOBt/NMM; (f) Pd(0)/NMM/AcOH; (g) 3-iodobenzoic acid/HBTU/HOBt/NMM; (h) 95% TFA/H₂O/TIS; (i) homovanillic acid/HBTU/HOBt/NMM.

Synthesis of Compound 8. Compound 8 was synthesized using standard Fmoc chemistry on the Rink amide resin (FIG. 18). The resin (200 mg, 0.7 mmol/g loading) was first activated by DCM (General procedure A). The Fmoc group on the resin was removed by piperidine in DMF (General procedure B). The resin was then coupled with Fmoc-Dpr(Boc)-OH. The Fmoc group on the resin was removed by piperidine in DMF (General procedure B). The resin was then coupled with Fmoc-Orn(Alloc)-OH. The Fmoc group was removed (General procedure B) and Fmoc-Phe-OH was attached to resin (General procedure E). The Fmoc group was again removed (general procedure B) and the amine group on the F$_2$Pmp residue was coupled with BMBA (general procedure E). The resin was treated with Pd(0) for the deprotection of Alloc group (general procedure C). 3-Iodobenzoic acid (mIBA) was attached to resin (general procedure E). The resin was treated with TFA (general procedure F) to give the crude peptide intermediate, which was treated with a mixture of HVA (0.5 M in DMF, 100 µL), HBTU (0.5 M in DMF, 100 µL), HOBt (0.5 M in DMF, 100 µL) and NMM (1.5 M in DMF, 100 µL) to give the crude product 8. The crude product was purified by HPLC to afford 8 (15.8 mg, 12% yield). The assignment of proton NMR utilized additional information from COSY. $^1$H NMR (500 MHz, DMSO-d$_6$): δ=8.70 (d, J=8.1 Hz, 1 H, BMBA-NH), 8.60-8.55 (m, 1 H, mIBA-NH), 8.35 (d, J=6.9 Hz, 1 H, Phe-NH), 8.19 (s, 1 H, mIBA-ArH), 8.04-7.95 (m, 2 H, Orn-NH, BMBA-ArH), 7.91-7.83 (m, 3 H, mIBA-ArH, HVA-NH), 7.67 (d, J=7.5 Hz, 1 H, BMBA-ArH), 7.40-7.15 (m, 9 H, BMBA-ArH, Phe-ArH, —CONH$_2$, mIBA-ArH), 6.77 (s, 1 H, HVA-ArH), 6.63 (d, J=7.6 Hz, 1 H, HVA-ArH), 6.58 (d, J=7.6 Hz, 1 H, HVA-ArH), 4.78-4.72 (m, 1 H, Phe-C$_\alpha$H), 4.30-4.22 (m, 2 H, Dpr-C$_\alpha^{H, Orn-C}$$_\alpha$H), 3.70 (s, 3 H, HVA-OCH$_3$), 3.40-3.35 (m, 1 H, Dpr-C$_\beta$HH'), 3.35-3.18 (m, HVA-CH$_2$-CO, Dpr-C$_\beta$HH', Orn-C$_\delta$H$_2$, Phe-C$_\beta$HH'), 3.04-2.96 (m, 1 H, Phe-C$_\beta$HH'), 2.35 (s, 3 H, BMBA-Ar—CH$_3$), 1.81-1.74 (m, 1 H, Orn-C$_\beta$HH'), 1.68-1.52 (m, 3 H, Orn-C$_\beta$HH', Orn-C$_\gamma$H$_2$). $^{13}$C NMR (125 MHz, DMSO-d$_6$): δ=171.79, 171.39, 171.25, 171.17, 164.70, 164.52, 147.13, 144.94, 140.65, 139.46, 138.30, 136.49, 135.51, 133.34, 130.75, 130.32, 129.00, 127.92, 126.62, 126.54, 126.10, 123.78, 121.26, 115.05, 113.13, 94.53, 55.37, 54.77, 53.01, 52.80, 41.74, 40.57, 36.68, 28.99, 25.46, 22.26. MS (ESI): calculated for [M], 954, found [M+H]$^+$ 955. HPLC purity analysis: >95% (UV, λ=254 nm).

Screening of Library 2b. The library screening assay was carried out on a Tecan Genesis workstation with a 96-channel tip block with fixed tips. Before screening, the library compounds were diluted from the DMSO stock solution into 3,3-dimethylglutarate buffer (50 mM 3,3-dimethylglutarate buffer, pH 7.0, containing 1 mM EDTA with an ionic strength of 0.15 M adjusted by addition of NaCl), resulting in a set of six daughter plates with an ~75 nM concentration of each compound in each well. In the first screen, PTP-MEG2 (2 µM in 50 mM 3,3-dimethylglutarate buffer, 50 µL, pH 7.0, containing 1 mM EDTA with an ionic strength of 0.15 M adjusted by addition of NaCl) was dispensed into each well of a 384-well plate, and then 2 µL of the fluorescein-tagged library compounds were transferred from four 96-well intermediate plates to the 384-well plate (final compound concentration ~3 nM). The fluorescence polarization values (A$_1$) were recorded on an Envision 2021 Multilabel Microplate Reader (Perkin-Elmer). In the second screen, 50 µL of a mixture of 2 µM PTP-MEG2 and 20 µM compound C1 (as a competitive ligand) in 3,3-dimethylglutarate buffer (50 mM 3,3-dimethylglutarate buffer, pH 7.0, containing 1 mM EDTA with an ionic strength of 0.15 M adjusted by addition of NaCl) were dispensed into each well of another 384-well plate, followed by the addition of 2 µL of the fluorescein tagged library compounds (75 nM in 3,3-dimethylglutarate buffer, pH 7.0, containing 1 mM EDTA with an ionic strength of 0.15 M adjusted by addition of NaCl). The fluorescence polarization values (A$_2$) were again measured. A displacement percentage was calculated for each library compound as (A$_1$−A$_2$)/(A$_1$−A$_0$)×100%, where A$_1$ and A$_2$ are the fluorescence anisotropy values of each sample as described, and A$_0$ is the fluorescence anisotropy of free library compounds in 3,3-dimethylglutarate buffer. To simplify the calculation, A$_0$ was set to 30. The binding affinity ranking of each compound was determined on the displacement percentage: the smaller the displacement percentage, the higher the binding affinity. The best hits were selected based on affinity and are listed in Table S1.

Screening of Library 4b. The library was screened using the same protocol as the library 2b, except that Compound 3 (final concentration as 10 µM) was used as the competitive ligand. The best hits were selected based on affinity and are listed in Table S2.

Screening of Library 6b. The library was screened using the same protocol as the library 2b, except that Compound 5 (finial concentration as 10 µM) was used as the competitive ligand. The best hits were selected based on affinity and are listed in Table S3.

Enzyme kinetic assay. PTP activity was assayed using p-nitrophenyl phosphate (pNPP) as a substrate in 3,3-dimethylglutarate buffer (50 mM 3,3-dimethylglutarate, pH 7.0, 1 mM EDTA, 150 mM NaCl, 2 mM DTT, 0.1 mg/mL BSA) at 25° C. The assays were performed in 96-well plates. Normally, to determine the IC$_{50}$ values, the reaction was initiated by the addition of enzyme (final concentration at 10 nM) to a reaction mixture (0.2 mL) containing 2 mM (K$_m$ for the substrate) pNPP with various concentrations of inhibitors. The reaction rate was measured using a SpectraMax Plus 384 Microplate Spectrophotometer (Molecular Devices). To determine the mode of inhibition, the reactions were initiated by the addition of PTP-MEG2 to the reaction mixtures (0.2 mL) containing various concentrations of pNPP with different concentrations of the inhibitor 7. Data were fitted using SigmaPlot Enzyme Kinetics Module (Systat Software, Inc.).

PTP-MEG2 Overexpression, and Purification. The expression vector containing residues 277-582 of PTP-MEG2 catalytic domain was provided by Stefan Knapp at the University of Oxford. For protein expression, transformed cells were grown at 37° C. in Luria broth (LB) containing 100 mg/mL ampicillin for 4 h to an OD600 nm @0.6, and then induced for overnight at 18° C. with 0.4 mM IPTG. Cells were harvested by centrifugation (6500 rpm for 15 min at 4° C.), and the cell pellets from 1.5 L LB medium were suspended in 30 mL of ice-cold lysis buffer consisting of 5 mM imidazole, 500 mM NaCl, 20 mM Tris-HCl (pH 7.9), 0.05 mg/mL trypsin inhibitor and 0.1 mM PMSF. The suspensions were passed twice through a French Press at 1200 psi, and the cell lysates were centrifuged at 4° C. for 30 min at 16,000 rpm. The supernatants were mixed with 2 mL Ni-NTA Agarose (His*Bind Resin) (Qiagen) at 4° C. for 1 hour, then transferred mixture to an empty column. The column was washed by 200 mL binding buffer (5 mM imidazole, 500 mM NaCl, 20 mM Tris-HCl (pH 7.9)), followed by 20 mL wash buffer (20 mM imidazole, 500 mM NaCl, 20 mM Tris-HCl (pH 7.9)), and then eluted with 20 mL elution buffer (200 mM imidazole, 500 mM NaCl, 20 mM Tris-HCl (pH 7.9), 5 mM DTT). The elution was dialyzed for 6 h at 4° C. against 1 L buffer A (50 mM NaCl, 20 mM MES (pH6.0), 1 mM EDTA), and then loaded onto a Mono S column equilibrated at 4° C. with buffer A. The column was washed with 10 ml buffer A and then eluted with a 40 mL linear gradient of 0 to 1M NaCl in buffer A. The PTP-MEG2 was eluted at 0.35 M NaCl. The column fractions were analyzed by measuring the absorbance at 280 nm and by carrying out SDS-PAGE analysis. The fractions were combined, dialyzed against 1 L buffer A and concentrated at 4° C. to 8 mg/mL using an Amicon concentrator and then stored at −80° C. The PTP-MEG2 was shown to be homogeneous by SDS-PAGE analysis.

Western blot analysis. Cells were homogenized in the lysis buffer (50 mM Hepes, pH 7.5, 150 mM NaCl, 10% Glycerol, 1% Triton X-100, 1.5 mM MgCl$_2$, 1 mM EGTA, 10 µM Sodium Pyrophosphate, 100 mM sodium fluoride and freshly added 100 μM sodium vanadate, 1 mM PMSF, 10 μg/ml Aprotinin, and 10 μg/mL Leupeptin). Protein extracts were resolved on an SDS-PAGE gel and transferred to nitrocellulose membrane. Proteins were probed using the following antibodies: IR(pY1162/63), IR (Santa Cruz Biotechnology), Akt(pS473), Aid, GSK3β(pS9), GSK3β, Foxo1(pS256), Foxo1, Erk1/2(pT202/Y204), Erk1/2 (Cell Signaling Technology). Protein signals were detected by incubation with HRP-conjugated secondary antibodies, followed by ECL detection reagent (Pierce). Western blots were scanned and quantified using the Quantity One software (Bio-Rad).

RNA isolation and real-time PCR. RNA isolation was performed as described previously (Jänne, et al. *Nat. Rev. Drug Discov.* 2009, 8, 709-723). Real-time RT-PCR was performed in two steps: first, cDNA was synthesized using a cDNA synthesis kit (Applied Biosystems Inc.); second, cDNA was analyzed by real-time PCR using SYBR Green Master Mix (Promega). Primer sequences for the specific genes are as follows: Ppia forward 5'-CACCGTGTTCTTCGACATCA-3'; Ppia reverse 5'-CAGTGCTCAGAGCTCGAAAGT-3'; G6pc forward 5'-TCGGAGACTGGTTCAACCTC-3'; G6pc reverse 5'-TCACAGGTGACAGGGAACTG-3'; Pdk4 forward GATTGACATCCTGCCTGACC; Pdk4 reverse CATG-GAACTCCACCAAATCC; Igfbp1 forward CTGC-CAAACTGCAACAAGAA; Igfbp1 reverse ACACCAGCAGAGTCCAGCTT.

Crystallization of PTP-MEG2 and X-ray Data Collection. PTP-MEG2 crystals were grown by vapor diffusion in hanging drops at 20° C. Drops containing 1:1 volumes of protein in stock buffer and reservoir solutions were equilibrated against the reservoir solution A (25% PEG 3350, 0.2 M Potassium thiocyanate, 10% Ethylene glycol, 0.1 M Bis-Tris propane pH 6.6). The crystal was transferred into a reservoir solution B (9 μL solution A mixed with 1 μL 20 mM stock of compound in DMSO), soaked for 12 hours, and flash-cooled in liquid nitrogen. X-ray data were collected at 100 K at SBC-CAT beamline 19-ID at the Advanced Photon Source (Argonne, Ill.) equipped with a mosaic CCD detector. The crystals belong to space group P1 with the following unit cell parameters: a=40.14 Å, b=57.77 Å, c=66.70 Å, α77.22°, β=78.03°, and γ=80.01°. There are two protein monomers in the asymmetric unit. The calculated crystal specific volume, VM, is 2.0 Å³/Da, corresponding to a solvent content of 39%. All data were processed with HKL3000 (Minor et al., 2006), and the statistics are provided in Table 2.

Structural Determination and Refinement. The structures of PTPMEG2•3 was solved by molecular replacement using the program AMoRe (Navaza, *Acta. Crystallogr. A* 1994, 50, 157-163). The structure of PTP-MEG2 catalytic domain (PDB entry code 2PA5) (Barr et al., *Cell* 2009, 136, 352-363), without the solvent and other small molecules, was used as a search model. The resulting difference Fourier map indicated some alternative tracing, which was incorporated into the model. The map revealed the density for the bound Compound 3 in the active site of PTP-MEG2. The structure was refined to 1.8 Å resolution with the program CNS 1.1 (Brünger et al., *Acta. Crystallogr. D. Biol. Crystallogr.* 1998, 54, 905-921), first using simulated annealing at 2,500 K, and then alternating positional and individual temperature factor refinement cycles. The progress of the refinement was evaluated by the improvement in the quality of the electron density maps, and the reduced values of the conventional R factor ($R=\Sigma_h||F_o|-|F_c||/\Sigma_h||F_o|$), and the free R factor (3.6% of the reflections omitted from the refinement) (Brünger, *Nature* 1992, 355, 472-475). Electron density maps were inspected and the model was modified on an interactive graphics workstation with the program O (Jones et al., *Acta. Crystallogr. A* 1991, 47, 110-119). Finally, water molecules were added gradually as the refinement progressed. They were assigned in the $|F_o|-|F_c|$ difference Fourier maps with a 3δ cutoff level for inclusion in the model. Using the same strategy, the structures of PTP-MEG2•5 and PTP-MEG2•7 were solved and refined to 2.0 Å and 1.4 Å, respectively. The statistics of refinements were also provided in Table 2.

Pharmacokinetic parameters for Compound 7. Compound 7 was quantified in mouse plasma using protein precipitation, internal standardization, and HPLC-MS/MS. Acetone was used to precipitate proteins and Compound 8 was the internal standard. Compound 7 and Compound 8 were separated using a C8 50×4.6 mm 5 um (Restek Ultra) HPLC column and a gradient mobile phase (acetonitrile:5 mM ammonium acetate). Compounds were detected using ESI in positive mode (Thermo Quantum Ultra; Thermo Fisher). The Q1/Q3 for Compound 7 and Compound 8 were 1087/300 and 957/231, respectively. The lower limit of quantification was 100 ng/mL using 20 μL of mouse plasma.

Pharmacokinetic parameters were estimated for Compound 7 after 5 mg/kg intravenous and 20 mg/kg intraperitoneal dosage, respectively. These parameters including area under the curve (AUC), area under the first moment curve (AUMC) and the elimination rate constant, $k_{el}$, were estimated using noncompartmental methods with add-ins on Excel®. The maximum plasma concentration ($C_{max}$) was obtained from the data. For the intravenous injection, the $C_{max}$ was estimated by extrapolating the data to zero time. The terminal half-life, $t_{1/2}$, was estimated with $0.693/k_{el}$. The AUC from the last concentration, $C_{last}$, to infinity was estimated by $C_{last}/k_{el}$. The systemic clearance (Cl or Cl/F) was calculated with dose/$AUC_{0-\infty}$ and the volume of distribution at steady state ($Vd_{ss}$ or $Vd_{ss}/F$) was calculated using the Cl and the mean residence time (MRT; MRT=(Dose/AUC)×(AUMC/AUC)). The bioavailability (F) was estimated by comparing the Cl of intravenous and intraperitoneal injections.

Pharmacokinetic parameters for Compound 7. The $t_{1/2}$, Cl, and $Vd_{ss}$ after 5 mg/Kg intravenous injection were 0.8 hrs, 0.014 L/hr, and 0.007 L, respectively. The $t_{1/2}$, Cl/F, and $Vd_{ss}/F$ after 20 mg/Kg intraperitoneal injection were 1.8 hrs, 0.047 L/hr, and 0.080 L, respectively. The $C_{max}$ after intraperitoneal injection was 4.5 μM and $C_{max}$ after intravenous injection was 25.7 μM. Bioavailability (F) was 0.30.

In view of the above, it will be seen that the several advantages of the disclosure are achieved and other advantageous results attained. As various changes could be made in the above devices and methods without departing from the scope of the disclosure, it is intended that all matter contained in the above description and shown in the accompanying drawings shall be interpreted as illustrative and not in a limiting sense.

What is claimed is:

1. A compound of Formula A:

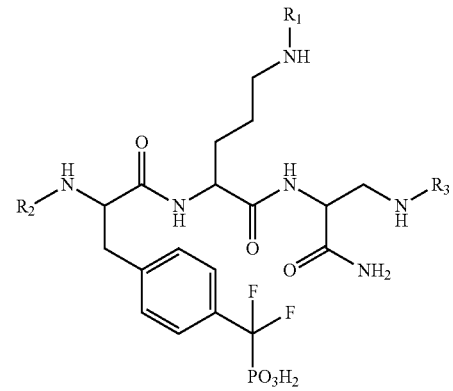

Formula A or a therapeutically suitable prodrug thereof or a therapeutically suitable salt thereof, wherein $R^1$, $R^2$, and $R^3$ are the same or different and each individually is an acyl group of a carboxylic acid.

2. The compound according to claim 1, wherein $R^1$ and $R^2$ are the same or different and each individually is an acyl group of a benzoic acid, the benzoic acid being optionally substituted with one or more moieties selected from the group consisting of halogen, hydroxyl, $C_1$-$C_5$ alkyl, and $C_1$-$C_5$ alkoxy, and wherein $R^3$ is an acyl group of a phenylacetic acid, the phenylacetic acid being optionally substituted with one or more moieties selected from the group consisting of halogen, hydroxyl, $C_1$-$C_5$ alkyl, and $C_1$-$C_5$ alkoxy.

3. The compound according to claim 1, having the structure of Compound 7:

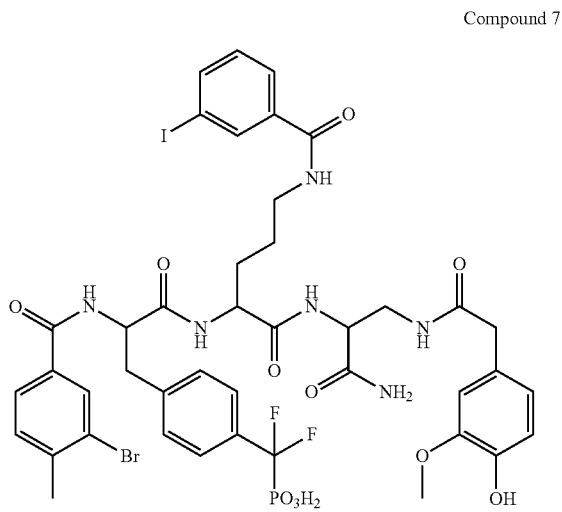

Compound 7 or a therapeutically suitable prodrug thereof or a therapeutically suitable salt thereof.

4. A pharmaceutical composition comprising a compound of claim 1 and a pharmaceutically acceptable carrier.

5. The pharmaceutical composition of claim 4, wherein the compound is Compound 7, a therapeutically suitable prodrug thereof, or a therapeutically suitable salt thereof.

6. The pharmaceutical composition of claim 5, wherein the composition is a formulation selected from the group consisting of capsule, cachet, tablet, lozenge, powder, granule, solution, suspension, emulsion, bolus, electuary, and paste.

7. The pharmaceutical composition of claim 5, wherein the composition further comprises an agent selected from the group consisting of antioxidant, buffer, bacteriostat, suspending agent, and thickening agent.

8. A method for treating a disease, disorder, or condition associated with inappropriate activity of a protein tyrosine phosphatase in an individual, the method comprising administering to the individual the compound of claim 1.

9. The method according to claim 8, wherein the compound is Compound 7, a therapeutically suitable prodrug thereof, or a therapeutically suitable salt thereof.

10. The method according to claim 9, wherein the disease, disorder, or condition is type 2 diabetes.

11. A method of manufacturing a medicament for the treatment of a disease, disorder, or condition associated with inappropriate activity of a protein tyrosine phosphatase, the method comprising mixing the compound of claim 1 with a pharmaceutically acceptable carrier.

12. The method according to claim 11, wherein the compound is Compound 7, a therapeutically suitable prodrug thereof, or a therapeutically suitable salt thereof.

13. The method according to claim 12, wherein the disease, disorder, or condition is type 2 diabetes.

14. A method for inhibiting a protein tyrosine phosphatase enzyme in an individual, the method comprising administering the compound of claim 1 to the individual.

15. The method according to claim 14, wherein $R^1$, $R^2$, and $R^3$ are the same or different and each individually is an acyl group of a benzoic acid, wherein the benzoic acid may be substituted with one or more moieties selected from the group consisting of halogen, hydroxyl, $C_1$-$C_5$ alkyl, and $C_1$-$C_5$ alkoxy.

16. The method according to claim 14, wherein the compound is Compound 7, a therapeutically suitable prodrug thereof, or a therapeutically suitable salt thereof.

17. The method according to claim 14, wherein the protein tyrosine phosphatase enzyme is protein tyrosine phosphatase, non-receptor type 9 (PTP-MEG2).

18. The method according to claim 14, wherein the protein tyrosine phosphatase enzyme is located in a human cell or an animal cell.

* * * * *